US007029606B2

(12) United States Patent
Dalton et al.

(10) Patent No.: US 7,029,606 B2
(45) Date of Patent: Apr. 18, 2006

(54) HYPERPOLARIZABLE ORGANIC CHROMOPHORES

(75) Inventors: Larry R. Dalton, Silverdale, WA (US);
Kwan-Yue Jen, Kenmore, WA (US);
Timothy Londergan, Seattle, WA (US);
William Brenden Carlson, Seattle, WA (US); Gregory Phelan, Seattle, WA (US); Diyun Huang, Seattle, WA (US);
Daniel Casmier, Seattle, WA (US);
Todd Ewy, Fort Walton Beach, FL (US); Nicholas Buker, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/912,444

(22) Filed: Jul. 24, 2001

(65) Prior Publication Data

US 2002/0084446 A1    Jul. 4, 2002

Related U.S. Application Data

(60) Provisional application No. 60/220,321, filed on Jul. 24, 2000.

(51) Int. Cl.
*G02F 1/061*    (2006.01)
*C07D 409/02*   (2006.01)
*C07D 307/00*   (2006.01)
*C07D 409/14*   (2006.01)
*C07D 495/02*   (2006.01)

(52) U.S. Cl. .................. 252/582; 252/583; 549/60; 549/29; 549/58; 549/59; 549/474; 549/475; 549/476; 546/94

(58) Field of Classification Search ................ 252/582, 252/583; 549/29, 58, 60, 474, 475, 476; 546/94
See application file for complete search history.

(56) References Cited

U.S. PATENT DOCUMENTS 5,156,774 A * 10/1992 Leising et al. ............. 252/582
5,432,286 A    7/1995 Cabrera et al. ............ 546/270

(Continued)

FOREIGN PATENT DOCUMENTS

WO    WO 00/009613 A2    2/2000

(Continued)

OTHER PUBLICATIONS

Lee, S.-S., et al., "Optical Intensity Modulator Based on a Novel Electrooptic Polymer Incorporating a High $\mu\beta$ Chromophore," *IEEE Journal of Quantum Electronics* 36(5): 527-532, May 2000.

(Continued)

*Primary Examiner*—Daniel S. Metzmaier
(74) *Attorney, Agent, or Firm*—Christensen O'Connor Johnson Kindness PLLC

(57) ABSTRACT

A dihydrofuran-containing nonlinear optical chromophore having a $\pi$-electron donor group conjugated to the dihydrofuran group through a $\pi$-electron conjugated bridge group. The nonlinear optical chromophore is a hyperpolarizable chromophore that can be used as an electro-optic modulator in electro-optic devices.

13 Claims, 45 Drawing Sheets

U.S. PATENT DOCUMENTS

| | | | |
|---|---|---|---|
| 5,514,799 A | 5/1996 | Varanasi et al. | 544/300 |
| 5,676,884 A | 10/1997 | Tiers et al. | 252/582 |
| 5,679,763 A | 10/1997 | Jen et al. | 252/582 |
| 5,693,734 A | 12/1997 | Herzig et al. | 528/27 |
| 5,718,845 A | 2/1998 | Drost et al. | 252/582 |
| 5,738,806 A | 4/1998 | Beckmann et al. | 252/582 |
| 5,804,101 A | 9/1998 | Marder et al. | 252/582 |
| 5,808,100 A | 9/1998 | Momoda et al. | 252/586 |
| 6,067,186 A | 5/2000 | Dalton et al. | 359/321 |
| 6,184,540 B1 | 2/2001 | Chmii et al. | 257/40 |
| 6,211,374 B1 | 4/2001 | Ippoliti | 546/153 |
| 6,281,366 B1 | 8/2001 | Frigoli et al. | 524/59 |
| 6,348,992 B1 | 2/2002 | Zhang et al. | 359/321 |
| 6,361,717 B1 | 3/2002 | Dalton et al. | 252/582 |
| 6,716,995 B1 * | 4/2004 | Huang et al. | 549/62 |

FOREIGN PATENT DOCUMENTS

WO    WO 01/53746 A1    7/2001

OTHER PUBLICATIONS

Robinson, B.H., et al., "The Molecular and Supramolecular Engineering of Polymeric Electro-Optic Materials," *Chemical Physics* 245:35-50, 1999, month unknown.

Shi, Y., et al., "Low (Sub-1-Volt) Halfwave Voltage Polymeric Electro-Optic Modulators Achieved by Controlling Chromophore Shape," *Science* 288:119-122, May 7, 2000.

* cited by examiner

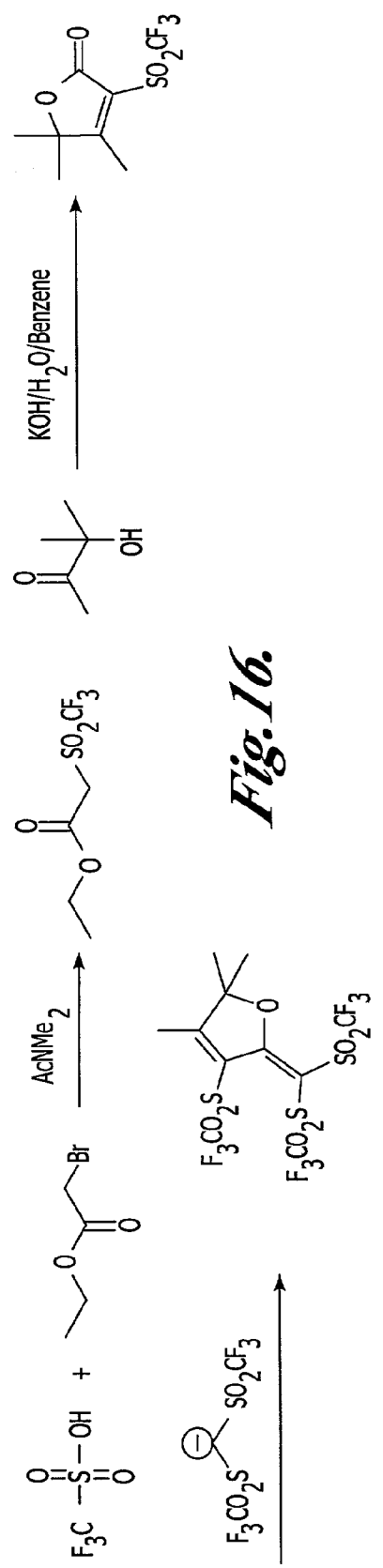
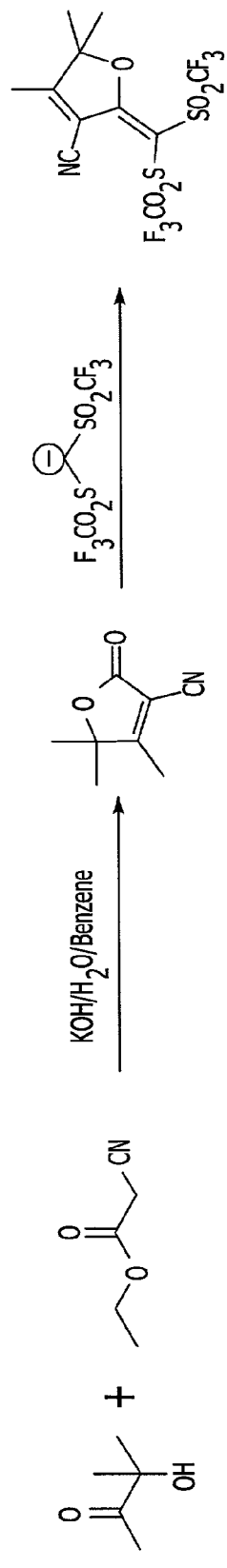
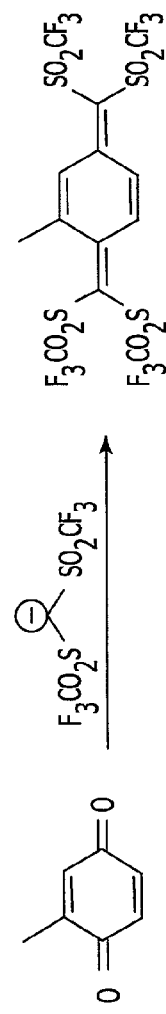
Fig. 16.
Fig. 19.
Fig. 20.

MACH ZEHNDER MODULATOR

BIREFRINGENT MODULATOR

DIRECTIONAL COUPLER $V(t) = V_0 \sin(\omega t) + V_B$

STRIP - LINE TOP ELECTRODE $I_{DC}(in)$ $I_1$ $I_{AC}(out)$ $I_2$

L $I_{AC}(out) = I_1 + I_2 + 2(I_1 I_2)^{1/2} \sin(\rho V_0 \sin(\omega t))$ $\rho = 2\pi r_{33} n^3 L V_0 / T\lambda$

COMPARISON OF KEY FEATURES OF SIMPLE DEVICES

|  | MACH ZEHNDER INTERFEROMETER | BIREFRINGENT MODULATOR | DIRECTIONAL COUPLER |
|---|---|---|---|
| $r_{eff}$ | $r_{33}$ | $r_{33}-r_{13}$ | $r_{33}$ |
| $V_\pi$ | $V_{\pi MZ}$ | $1.5\, V_{\pi MZ}$ | $1.73\, V_{\pi MZ}$ |
| Mod. Power | $P_{MZ}$ | $2.75\, P_{MZ}$ | $3\, P_{MZ}$ |

US 7,029,606 B2

HYPERPOLARIZABLE ORGANIC CHROMOPHORES

CROSS-REFERENCE TO RELATED APPLICATION

This application claims the benefit of U.S. patent application Ser. No. 60/220,321, filed Jul. 24, 2000.

FIELD OF THE INVENTION

The present invention relates in general to nonlinear optically active molecules and, more particularly to hyperpolarizable organic chromophores having useful electro-optical coefficients.

REFERENCES

Each reference cited in the application, including citations to literature and patent documents, is expressly incorporated herein by reference in its entirety.

BACKGROUND OF THE INVENTION

Electrical signals can be encoded onto fiber-optic transmissions by electro-optic modulators. These modulators include electro-optic materials having highly polarizable electrons. When these materials are subject to an electric field, their polarization changes dramatically resulting in an increase in the index of refraction of the material and an accompanying decrease in the velocity of light travelling through the material. This electric field-dependent index of refraction can be used to encode electric signals onto optical signals. Uses include, for example, switching optical signals and steering light beams.

A variety of electro-optic materials have been utilized for use in electro-optic devices. Among these materials are inorganic materials such as lithium niobate, semiconductor materials such as gallium arsenide, organic crystalline materials, and electrically-poled polymer films that include organic chromophores. A review of nonlinear optical materials is provided in L. Dalton, "Nonlinear Optical Materials", Kirk-Othmer Encyclopedia of Chemical Technology, 4$^{th}$ Edition, Volume 17 (John Wiley & Sons, New York, 1995), pp. 288–302.

In contrast to inorganic materials in which polar optical lattice vibrations diminish their effectiveness, the optical properties of organic nonlinear optical materials depend primarily on the hyperpolarizability of their electrons without a significant adverse contribution from the lattice polarizability Thus, organic nonlinear optical materials offer advantages for ultrafast electro-optic modulation and switching.

Lithium niobate, a common material currently utilized in electro-optic devices, has an electro-optic coefficient of about 35 pm/V resulting in a typical drive voltage of about 5 volts. Drive voltage ($V_\pi$) refers to the voltage required to produce a $\pi$ phase shift of light. Lithium niobate has a high dielectric constant ($\epsilon$=28), which results in a mismatch of electrical and optical waves propagating in the material. The mismatch necessitates a short interaction length, which makes drive voltage reduction through increasing device length unfeasible, thereby limiting the device's bandwidth. Recent lithium niobate modulators have been demonstrated to operate at a bandwidth of over 70 GHz.

Electro-optic poled polymers have also been utilized as modulating materials. Their advantages include their applicability to thin-film waveguiding structures, which are relatively easily fabricated and compatible with existing microelectronic processing. These polymers incorporate organic nonlinear optically active molecules to effect modulation. Because organic materials have low dielectric constants and satisfy the condition that $n^2=\epsilon$, where n is the index of refraction and $\epsilon$ is the dielectric constant, organic electro-optic will have wide bandwidths. The dielectric constant of these materials ($\epsilon$=2.5–4) relatively closely matches the propagating electrical and optical waves, which provides for a drive voltage in the range of about 1–2 volts and a bandwidth greater than 100 GHz.

Advantages of organic nonlinear optical materials include a bandwidth in excess of 100 GHz/cm device and ease of integration with semiconductor devices. See, L. Dalton et al., "Synthesis and Processing of Improved Organic Second-Order Nonlinear Optical Materials for Applications in Photonics", *Chemistry of Materials*, Vol. 7, No. 6, pp. 1060–1081 (1995). In contrast to inorganic materials, these organic materials can be systematically modified to improve electro-optic activity by the design and development of new organic materials and by the development of improved processing methods. See, L. Dalton et al., "The Role of London Forces in Defining Noncentrosymmetric Order of High Dipole Moment-High Hyperpolarizability Chromophores in Electrically Poled Polymeric Films", *Proceedings of the National Academy of Sciences USA*, Vol. 94, pp. 4842–4847 (1997).

For an organic nonlinear optical material to be suitable for electro-optic applications, the material should have a large molecular optical nonlinearity, referred to as hyperpolarizability ($\beta$), and a large dipole moment ($\mu$). A common figure of merit used to compare materials is the value $\mu\beta$. See Dalton et al. (1997). Organic materials having $\mu\beta$ values greater than about 15,000×10$^{-48}$ esu that also satisfy the requirements of thermal and chemical stability and low optical loss at operating wavelengths have only recently been prepared. See Dalton et al., "New Class of High Hyperpolarizability Organic Chromophores and Process for Synthesizing the Same", WO 00/09613. However, materials characterized as having such large $\mu\beta$ values suffer from large intermolecular electrostatic interactions that lead to intermolecular aggregation resulting in light scattering and unacceptably high values of optical loss. See Dalton et al. (1997).

Thus, the effectiveness of organic nonlinear optical materials having high hyperpolarizability and large dipole moments is limited by the tendency of these materials to aggregate when processed into electro-optic devices. The result is a loss of optical nonlinearity. Accordingly, there exist a need for improved nonlinear optically active materials having large hyperpolarizabilities and large dipole moments and that, when employed in electro-optic devices, exhibit large electro-optic coefficients. The present invention seeks to fulfill these needs and provides further related advantages.

SUMMARY OF THE INVENTION

In one aspect, the present invention provides a hyperpolarizable organic chromophore. The chromophore is a nonlinear optically active compound that includes a $\pi$-donor conjugated to a $\pi$-acceptor through a $\pi$-electron conjugated bridge. In other aspects of the invention, donor structures, bridge structures, and acceptor structures are provided.

In another aspect of the invention, a chromophore-containing polymer is provided. In one embodiment, the chromophore is physically incorporated into the polymer to provide a composite, in another embodiment, the chromophore is covalently bonded to the polymer.

In a further aspect, the invention provides a chromophore-containing macromolecular structure. In one embodiment, the macromolecular structure is incorporated into a polymer host. In another embodiment, the macrostructure is crosslinkable and can be crosslinked to provide a lattice. The lattice can include a polymer host or, alternatively, be formed from the crosslinked dendrimer alone. The macromolecular structure can include a single chromophore or can include multiple chromophores. The macromolecular structure can be a chromophore-containing dendrimer (also referred to herein as "dendrimer functionalized chromophore"). In one embodiment, the chromophore-containing dendrimer is a Tomalia-type dendrimer. In another embodiment, the chromophore-containing dendrimer is convergently synthesized.

In yet another aspect of the invention, an electro-optic device is provided. In some embodiments, the devices incorporate a hyperpolarizable chromophore of the invention. In certain embodiments, the devices include a chromophore-containing polymer. In other embodiments, the devices include a chromophore-containing dendrimer.

In other aspects, the present invention also provides a method for making the chromophore, a method for making the chromophore-containing polymer, a method for making the chromophore-containing dendrimer, and methods for using the chromophore and chromophore-containing polymer and dendrimer.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 16 is a synthetic scheme for the preparation of a trifluoromethylsulfonyl substituted acceptor useful in the preparation of the chromophores of the invention;

FIG. 19 is a synthetic scheme for the preparation of a trifluoromethylsulfonyl substituted acceptor useful in the preparation of the chromophores of the invention;

FIG. 20 is a synthetic scheme for the preparation of a trifluoromethylsulfonyl substituted acceptor useful in the preparation of the chromophores of the invention;

DETAILED DESCRIPTION OF THE PREFERRED EMBODIMENT

Figure 1A:
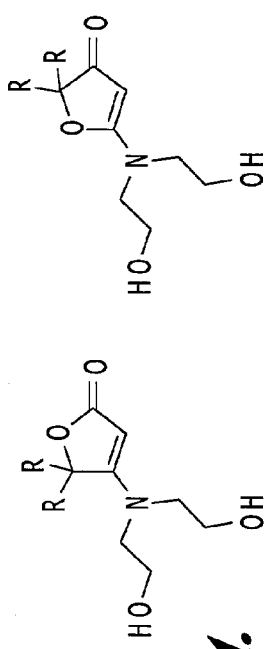
FIG. 1A illustrates the structures of two representative donor groups useful in the chromophores of the invention.
Figure 1B:
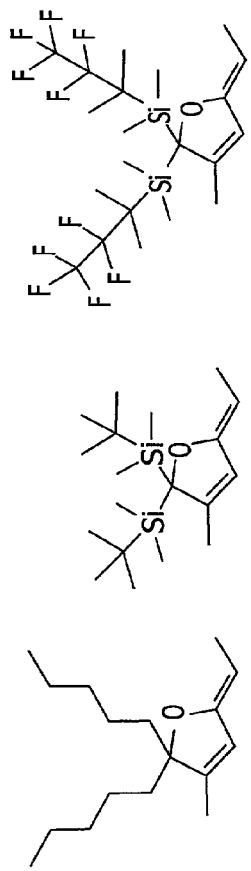
FIG. 1B illustrates the structures of three representative bridge groups useful in the chromophores of the invention.
Figure 1C:
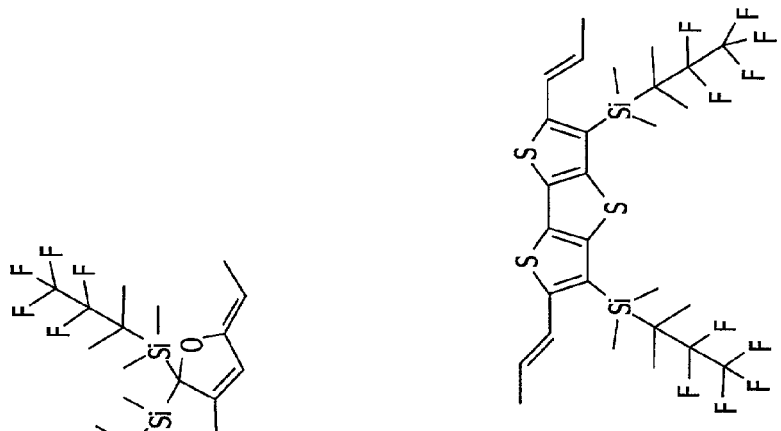
FIG. 1C illustrates the structures of three representative bridge groups useful in the chromophores of the invention.
Figure 1C:
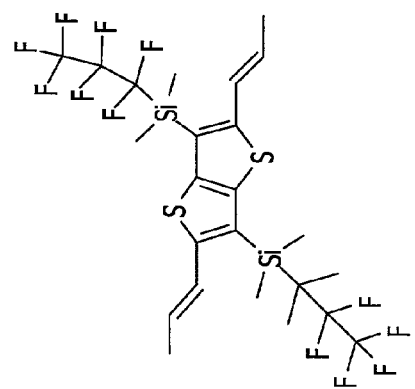
Figure 1C:
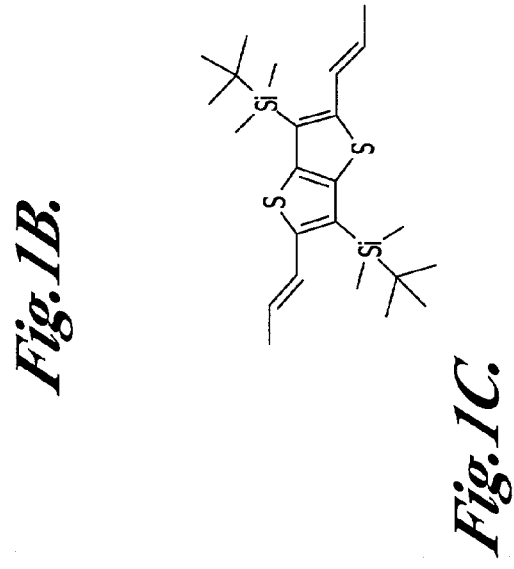
Figure 1D:
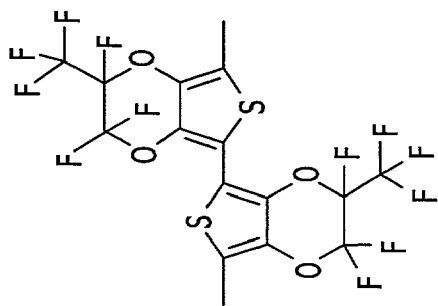
FIG. 1D illustrates the structure of three representative bridge groups useful in the chromophores of the invention.
Figure 1D:
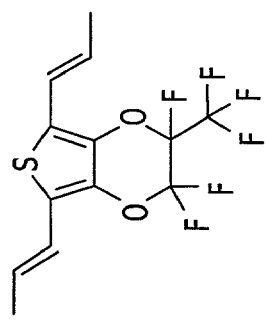
Figure 1D:
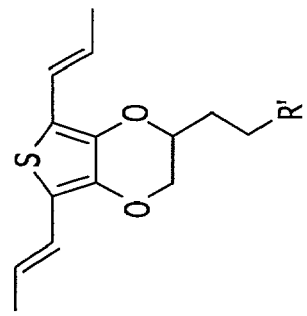
Figure 1E:
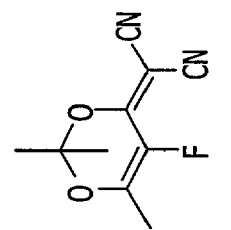
FIG. 1E illustrates the structures of five representative acceptor groups useful in the chromophores of the invention.
Figure 1E:
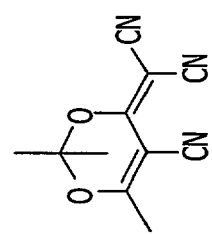
Figure 1E:
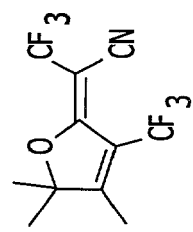
Figure 1E:
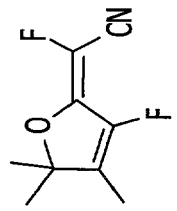

In one aspect, the present invention provides a hyperpolarizable organic chromophore. The chromophore is a nonlinear optically active compound that includes a π-donor conjugated to a π-acceptor through a π-electron conjugated bridge.

The chromophores of the invention are characterized as having high electro-optic coefficients; large hyperpolarizability; large dipole moments; chemical, thermal, electrochemical, and photochemical stability; low absorption at operating wavelengths (e.g., 1.3 and 1.55 μm); suitable solubility in spin casting solvents; compatibility with polymer hosts; and low volatility.

Optical Hyperpolarizability ($\mu\beta$). Nonlinear optical effects of organic materials depend mainly on the compound's hyperpolarizability ($\beta$). A measure of organic chromophore nonlinearity is $\mu\beta$, where $\mu$ is the chromophore dipole moment. A chromophore's optical nonlinearity ($\mu\beta$) can be measured as described in Dalton et al., "Importance of Intermolecular Interactions in the Nonlinear Optical Properties of Poled Polymers", *Applied Physics Letters*, Vol. 76, No. 11, pp. 1368–1370 (2000).

The chromophores of the invention are characterized as having high optical nonlinearities. In certain embodiments, the invention provides chromophores having optical nonlinearities with $\mu\beta$ greater than about $10,000 \times 10^{-48}$ esu. In other embodiments, chromophores are provided having optical nonlinearities with $\mu\beta$ up to at least about $5,000 \times 10^{-69}$ Cm$^5$/V measured at 1907 nm. Representative chromphores having high optical nonlinearity include those described in Example 4.

Electro-Optic Coefficient ($r_{33}$). A chromophore's electro-optic coefficient ($r_{33}$) can be measured in a polymer matrix using attenuated total reflection (ATR) technique at telecommunication wavelengths of 1.3 or 1.55 μm. A representative method for measuring the electro-optic coefficient is described in Dalton et al., "Importance of Intermolecular Interactions in the Nonlinear Optical Properties of Poled Polymers", *Applied Physics Letters*, Vol. 76, No. 11, pp. 1368–1370 (2000).

The chromophores of the invention are characterized as having an electro-optic coefficient ($r_{33}$) of at least about 50 pm/V measured at 1.3 or 1.55 μm in polymethylmethacrylate with a compound loading of about 25% by weight based on the total weight of polymethylmethacrylate. Representative chromphores having high electro-optic coefficients include those described in Example 4.

Chromophore Aggregation. Intermolecular attractive forces can cause chromophore aggregation diminishing hyperpolarizability and electro-optic coefficient. Chromophore design can reduce/eliminate aggregation increasing chromophore hyperpolarizability and electro-optic coefficient.

Many molecules can be prepared having high hyperpolarizability values, however their utility in electro-optic devices is often diminished by the inability to incorporate these molecules into a host material with sufficient noncentrosymmetric molecular alignment to provide a device with acceptable electro-optic activity. Molecules with high hyperpolarizability typically exhibit strong dipole-dipole interactions in solution or other host material that makes it difficult, if not impossible to achieve a high degree of noncentrosymmetric order unless undesirable spatially anisotropic intermolecular electrostatic interactions are minimized.

Chromophore performance is dependent on chromophore shape. See Dalton et al., "Low (Sub-1-Volt) Halfwave Voltage Polymeric Electro-optic Modulators Achieved by Controlling Chromophore Shape", *Science*, Vol. 288, pp. 119–122 (2000). In certain embodiments, the chromophores of the invention have shapes that reduce the disadvantageous intermolecular interactions. The chromophores include substituents that sterically inhibit such interactions. In one embodiment, the chromophore includes one or more substituents on donor group portion of the chromophore. In another embodiment, the chromophore includes one or more substituents on bridge portion of the chromophore. In a further embodiment, the chromophore includes one or more substituents on the acceptor portion of the of the chromophore. The chromophores of the invention can include combinations of donors, bridges, and acceptors, one or more of which can include substituents to provide site isolation. Thus, in certain embodiments, the invention provides chromophores having one or more substituents effective to reduce intermolecular chromophore association. In certain embodiments, the invention provides spherical, and nearly spherical, chromophores. In these embodiments, the chromophore is embedded within the molecular structure which effectively insulates the chromophore dipole from interaction with other such dipoles.

Donor, bridge, and acceptor substituents suitable to promote site isolation are described below and illustrated in the drawings.

Through the use of substitution and control of chromophore shape, the chromophores of the invention provide high electro-optic coefficients when incorporated into electro-optic devices.

Chromophore Stability. Chemical, thermal, and photochemical stabilities are imparted to the chromophores through their chemical structure and substituent choice. For example, in certain embodiments, the chromophore's active hydrogens are substituted with groups (e.g., alkyl, fluorine) to impart increased stability to the chromophore. Suitable substituted donors, bridges, acceptors, and chromophores are described below and illustrated in the drawings.

Representative Chromophore Components and Structures. In addition to providing chromophores, the present invention provides donors, bridges, and acceptor components useful in the construction chromophores for electro-optic device adaptation. As noted above, the chromophores of the invention include: (1) a π-donor conjugated to (2) a π-acceptor through (3) a π-electron conjugated bridge.

Donors. Representative donor structures are illustrated in, for example, FIGS. 1A, 2A, 3, 8, 15, 27, 36, 37, and 48 and described below. The donor can be an amino donor that includes an amino group.

In one embodiment, the donor includes an amino group conjugated to the π-electron conjugated through an α,β-unsaturated cyclic ester equivalent having the structure:

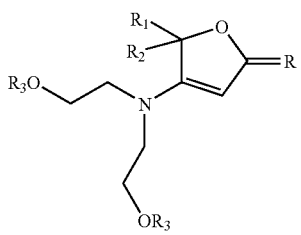

wherein $R_1$ and $R_2$ are alkyl groups (e.g., methyl, ethyl, propyl, butyl, pentyl, and hexyl groups), $R_3$ is a bulky substituent (e.g., TBDMS, t-butyldimethylsilyl group), and R represents an oxygen atom, or when the donor is incorporated into a chromophore, R represents the rest of the chromophore. A synthetic scheme for the preparation of this class of donor is presented in FIG. 3.

In another embodiment, the donor includes an amino group conjugated to the π-electron conjugated through an α,β-unsaturated cyclic ether equivalent having the structure:

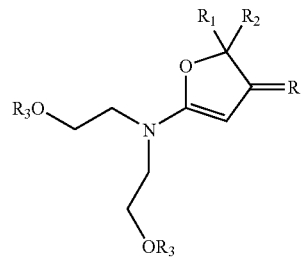

wherein $R_1$ and $R_2$ are alkyl groups (e.g., methyl, ethyl, propyl, butyl, pentyl, and hexyl groups), $R_3$ is a bulky substituent (e.g., TBDMS, t-butyldimethylsilyl group), and R represents an oxygen atom, or when the donor is incorporated into a chromophore, R represents the rest of the chromophore.

Other donor groups include phenyl amino groups, including triphenyl amino groups.

In certain embodiments, the donor includes a bulky substituent to inhibit chromophore aggregation. The donor can include functional groups for coupling to a dendron to ultimately provide a dendrimer functionalized chromophore. In other embodiments, the donor includes a functional group (e.g., trifluorovinyl ether) suitable for crosslinking to either a polymer matrix or other suitably functionalized chromophores.

Acceptors. Representative acceptor structures are illustrated in FIGS. 1E, 2A, 2B, 11, 15–17, 19, 20, 22, and 28–32 and described below. In certain embodiments, the acceptor includes a cyanofuran group.

In one embodiment, the acceptor includes a furan group having the structure:

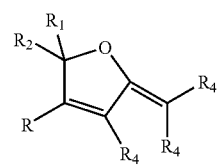

wherein $R_1$ and $R_2$ are alkyl groups, $R_4$ is either a F, CN, $CF_3$, or $SO_2CF_3$ substituent, and R represents a functional group capable of forming a covalent bond with the bridge portion of the chromophore, or when the donor is incorporated into a chromophore, R represents the rest of the chromophore.

Representative acceptors include acceptors having the above structure in which $R_1$ and $R_2$ are methyl groups and $R_4$ is a F substituent; and in which $R_1$ and $R_2$ are methyl groups and $R_4$ is a $CF_3$ substituent. A synthetic scheme for the preparation of a representative embodiment of this acceptor is provided in Example 1.

In another embodiment, the acceptor includes a group having the structure:

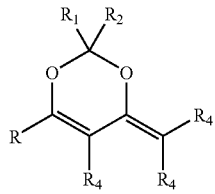

wherein $R_1$ and $R_2$ are alkyl groups, $R_4$ is either a F, CN, $CF_3$, or $SO_2CF_3$ substituent, and R represents a functional group capable of forming a covalent bond with the bridge portion of the chromophore, or when the donor is incorporated into a chromophore, R represents the rest of the chromophore.

Representative acceptors include acceptors having the above structure in which $R_1$ and $R_2$ are methyl groups and $R_4$ is a F substituent; $R_1$ and $R_2$ are methyl groups and $R_4$ is a CN substituent; and $R_1$ and $R_2$ are methyl groups and $R_4$ is a $CF_3$ substituent.

Bridges. Representative bridge structures are illustrated in FIGS. 1B, 1C, 1D, 2A, 2B, 2C, 2D, 2E, 2F, 2G, 2H, and 21, 4–7, 10, 13, 15, 17, 22, 26, and 28–32 described below. The bridge structure is a π-electron conjugated bridge. The bridge can include a variety of groups including, for example, a dihydrofuran group, a fused dithiophene group, a fused trithiophene group, a dithiophene group, and a substituted versions of these groups. As with the donor and acceptor groups noted above, substituted bridges can include functionalized substituents for coupling to dendron or for crosslinking.

In certain embodiments, the π-electron conjugated bridge includes a bulky substituent to inhibit chromophore aggregation. Included among these substituents are alkyl substituents.

Figure 2A:
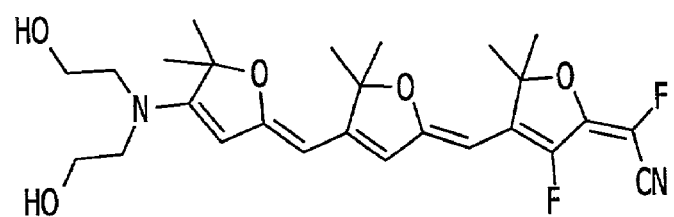
FIG. 2A illustrates the structure of a representative chromophore of the invention.
Figure 2B:
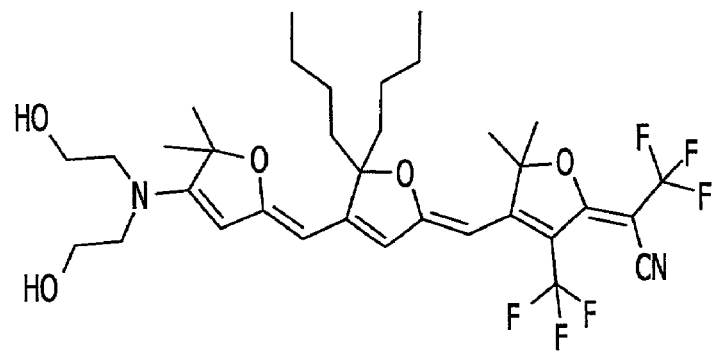
FIG. 2B illustrates the structure of a representative chromophore of the invention.
Figure 2C:
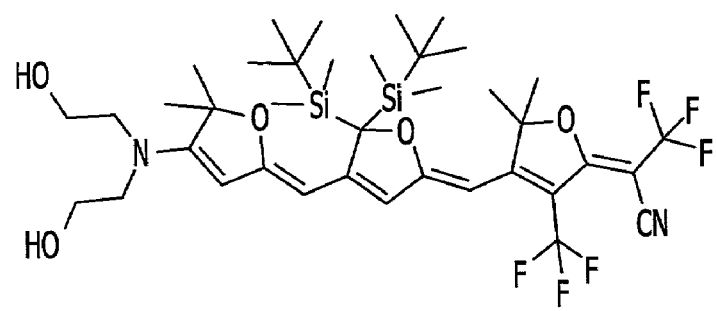
FIG. 2C illustrates the structure of a representative chromophore of the invention.
Figure 2D:
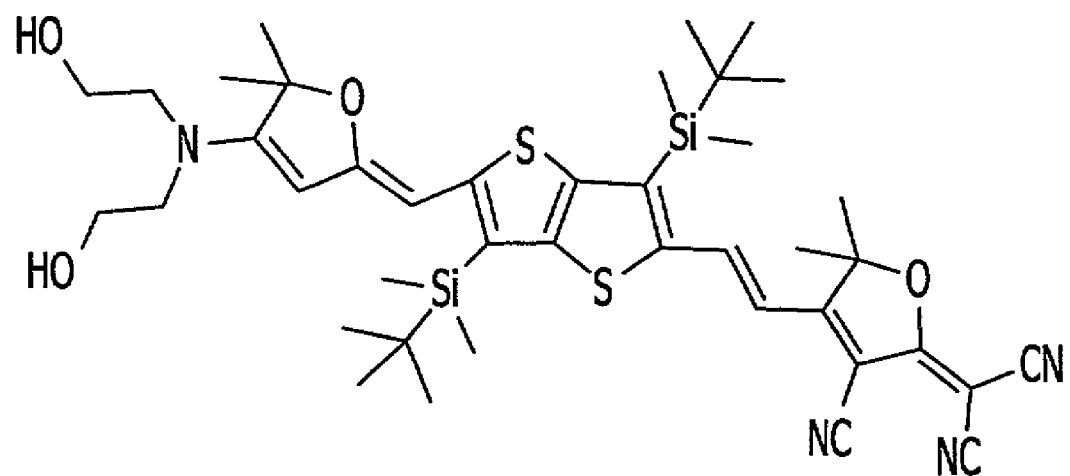
FIG. 2D illustrates the structure of a representative chromophore of the invention.
Figure 2E:
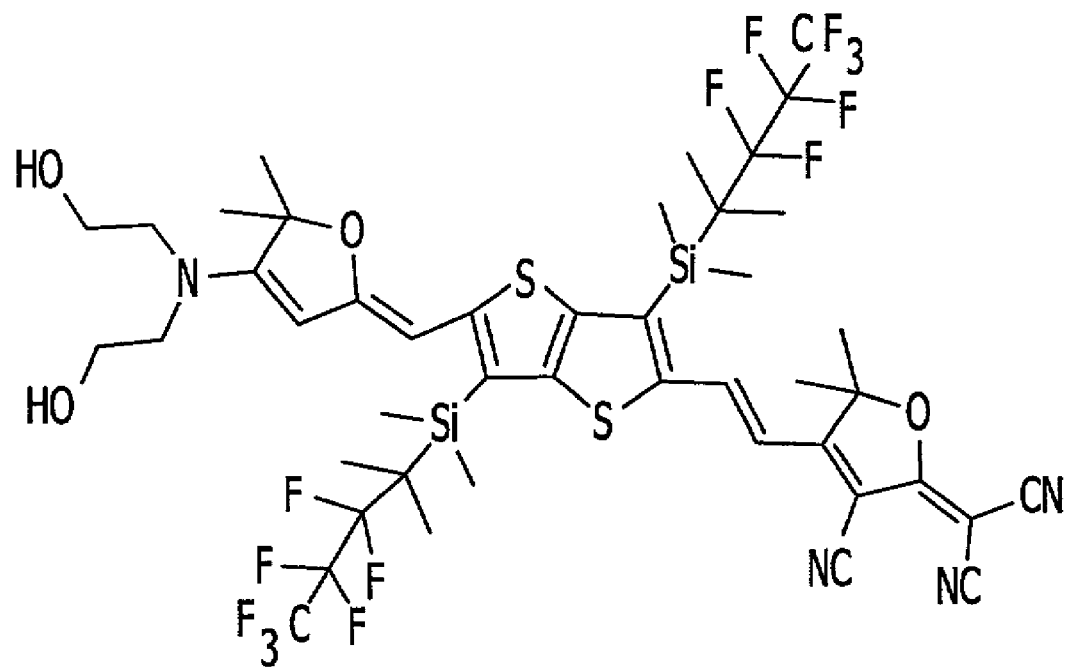
FIG. 2E illustrates the structure of a representative chromophore of the invention.

In one embodiment, the π-electron conjugated bridge includes a dihydrofuran group having the structure:

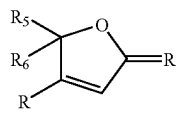

wherein $R_5$ and $R_6$ are selected from alkyl and silyl groups, for example, t-butyldimethyl silyl and perfluoropropyldimethyl silyl groups, and R represents a functional group capable of forming a covalent bond with the donor and acceptor portions of the chromophore, or when the donor is incorporated into a chromophore, R represents the rest of the chromophore. Chromophores that include the bridge are illustrated in FIGS. 2A, 2B, and 2C.

In another embodiment, the π-electron conjugated bridge includes a fused dithiophene group having the structure:

wherein $R_5$ and $R_6$ are, for example, alkyl or silyl groups, such as t-butyldimethyl silyl

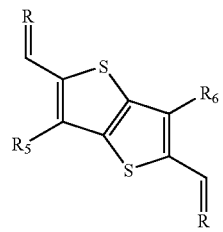

and perfluoropropyldimethyl silyl groups, and R represents a functional group capable of forming a covalent bond with the donor and acceptor portions of the chromophore, or when the donor is incorporated into a chromophore, R represents the rest of the chromophore. A synthetic scheme for the preparation of this class of bridge is presented in FIG. 4. A synthetic scheme for the preparation of a representative embodiment of this bridge is provided in Example 1. Chromophores that include the bridge are illustrated in FIGS. 2D, 2E, 12, 14, 21, and 26.

Figure 2F:
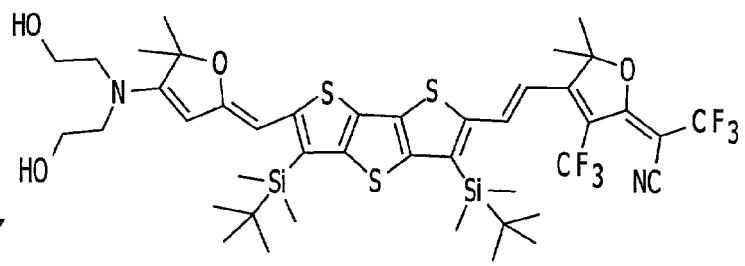
FIG. 2F illustrates the structure of a representative chromophore of the invention.
Figure 2G:
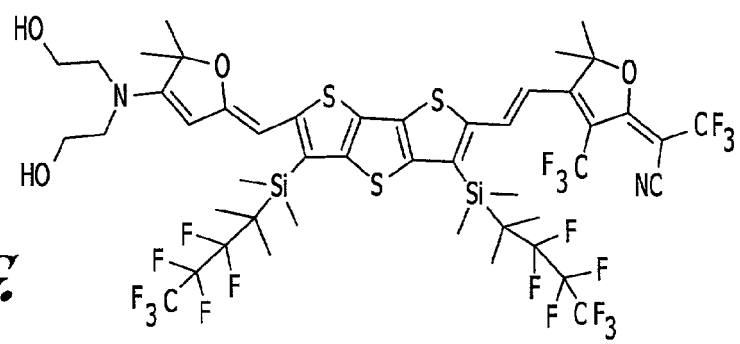
FIG. 2G illustrates the structure of a representative chromophore of the invention.

In a further embodiment, the π-electron conjugated bridge includes a fused trithiophene group having the structure:

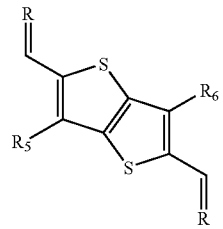

wherein $R_5$ and $R_6$ are, for example, alkyl or silyl groups selected from t-butyldimethyl silyl and perfluoropropyldimethyl silyl groups, and R represents a functional group capable of forming a covalent bond with the donor and acceptor portions of the chromophore, or when the donor is incorporated into a chromophore, R represents the rest of the chromophore. A synthetic scheme for the preparation of this class of bridge is presented in FIG. 5. Chromophores that include the bridge are illustrated in FIGS. 2F AND 2G.

Figure 8:
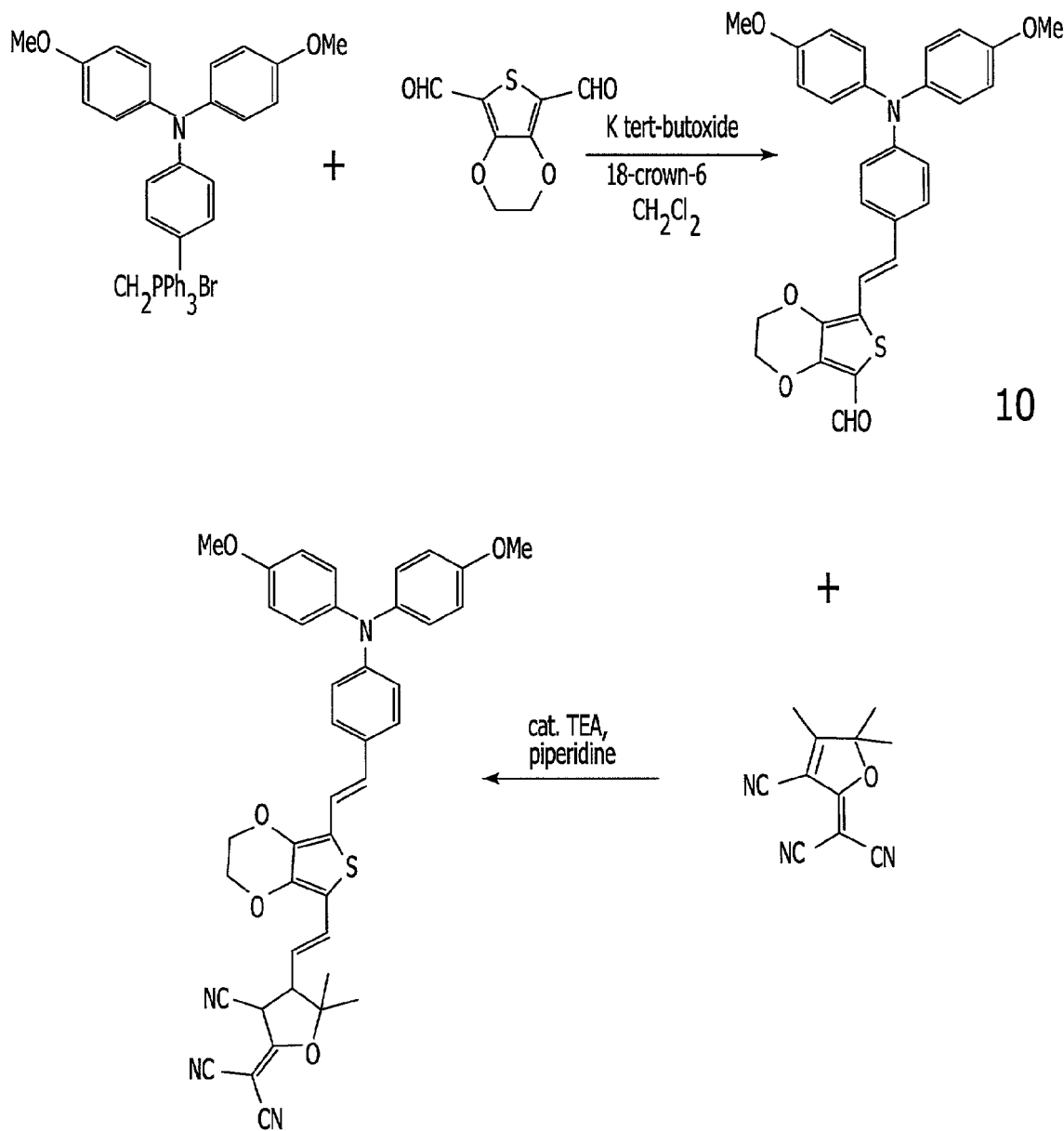
FIG. 8 is a synthetic scheme for the preparation of a representative thiophene-bridged chromophore of the invention.
Figure 14:
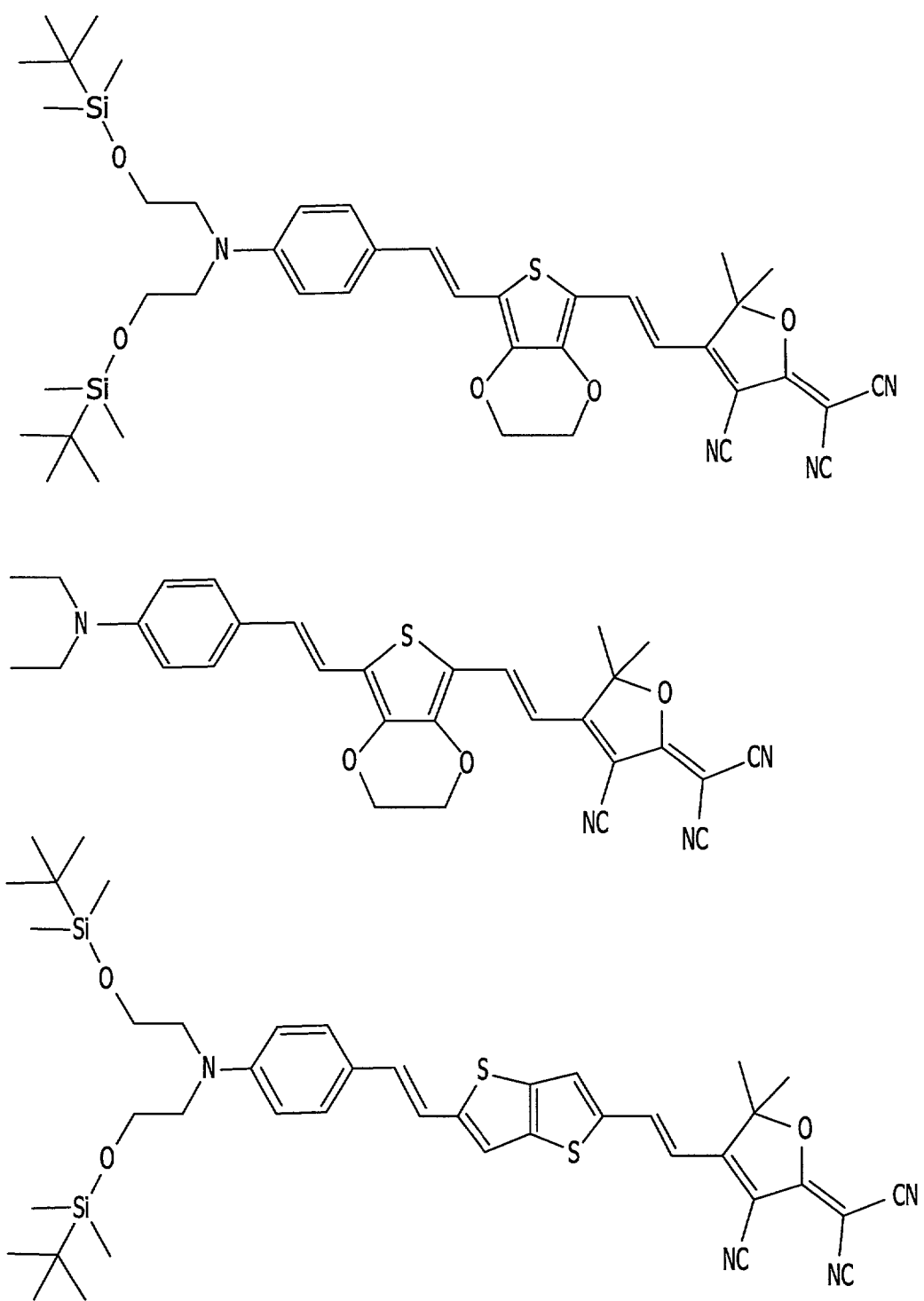
FIG. 14 is an illustration of representative thiophene-bridged chromophores of the invention.

In still another embodiment, the π-electron conjugated bridge includes a substituted thiophene group having the structure:

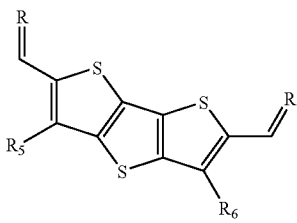

wherein $R_7$, $R_8$, $R_9$, and $R_{10}$ are hydrogen or alkyl groups, or wherein $R_7$, $R_8$, $R_9$, and $R_{10}$ are fluorine, or wherein $R_7$, $R_8$, and $R_9$ are fluorine and $R_{10}$ is a trifluoromethyl group; and R represents a functional group capable of forming a covalent bond with the donor and acceptor portions of the chromophore, or when the donor is incorporated into a chromophore, R represents the rest of the chromophore. A synthetic scheme for the preparation of this class of bridge is presented in FIG. 6. A synthetic scheme for the preparation of a representative embodiment of this bridge is provided in Example 2. Chromophores that include the bridge are illustrated in FIGS. 8 and 14.

In yet another embodiment, the π-electron conjugated bridge includes a dithiophene group having the structure:

wherein $R_7$, $R_8$, $R_9$, and $R_{10}$ are hydrogen or alkyl groups, or wherein $R_7$, $R_8$, $R_9$, and

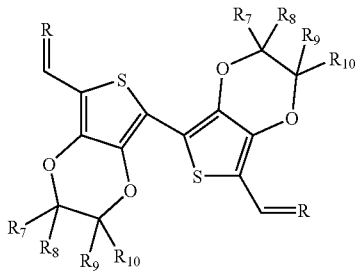

Figure 2H:
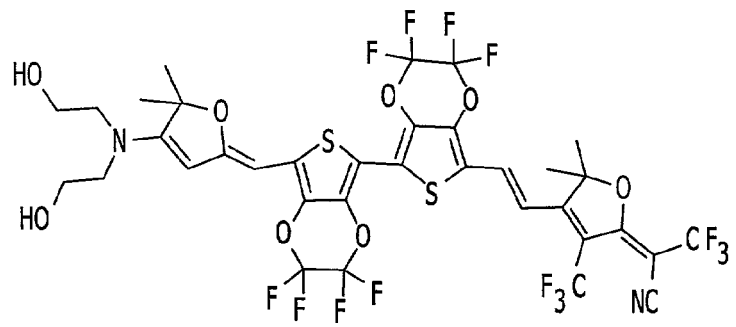
FIG. 2H illustrates the structure of a representative chromophore of the invention.
Figure 2I:
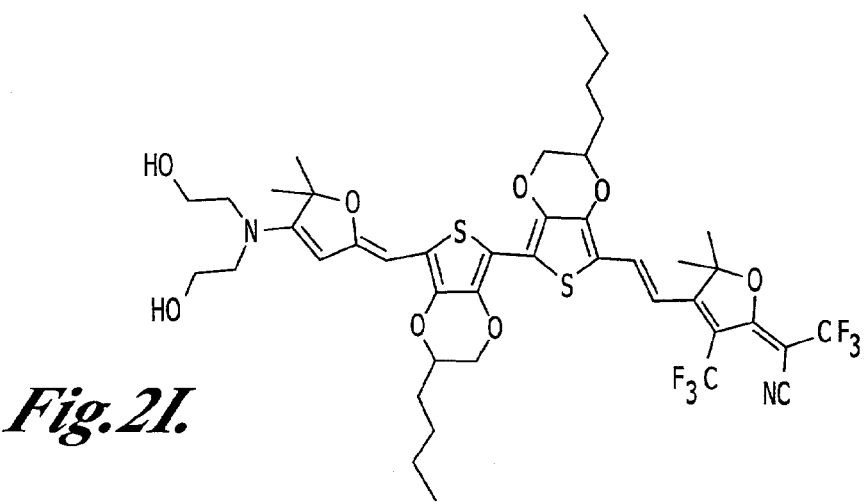
FIG. 2I illustrates the structure of a representative chromophore of the invention.
Figure 3:
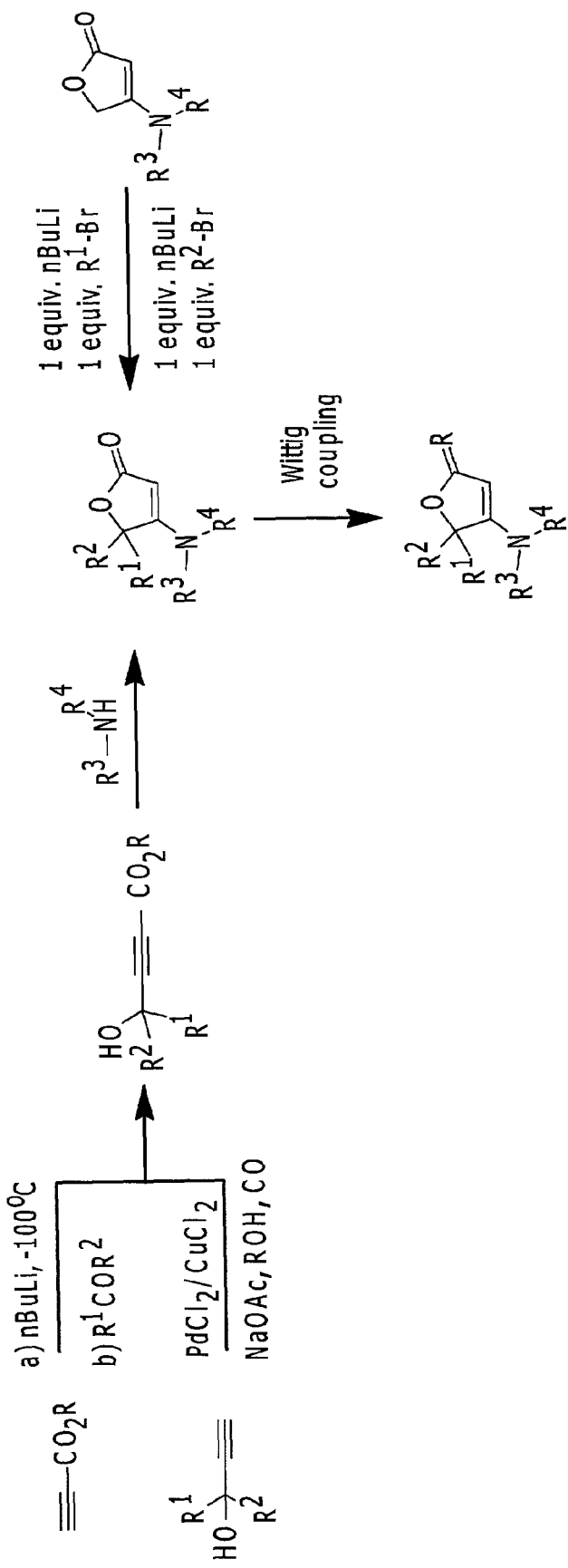
FIG. 3 is a synthetic scheme for the preparation of representative amine donors of the invention.
Figure 4:
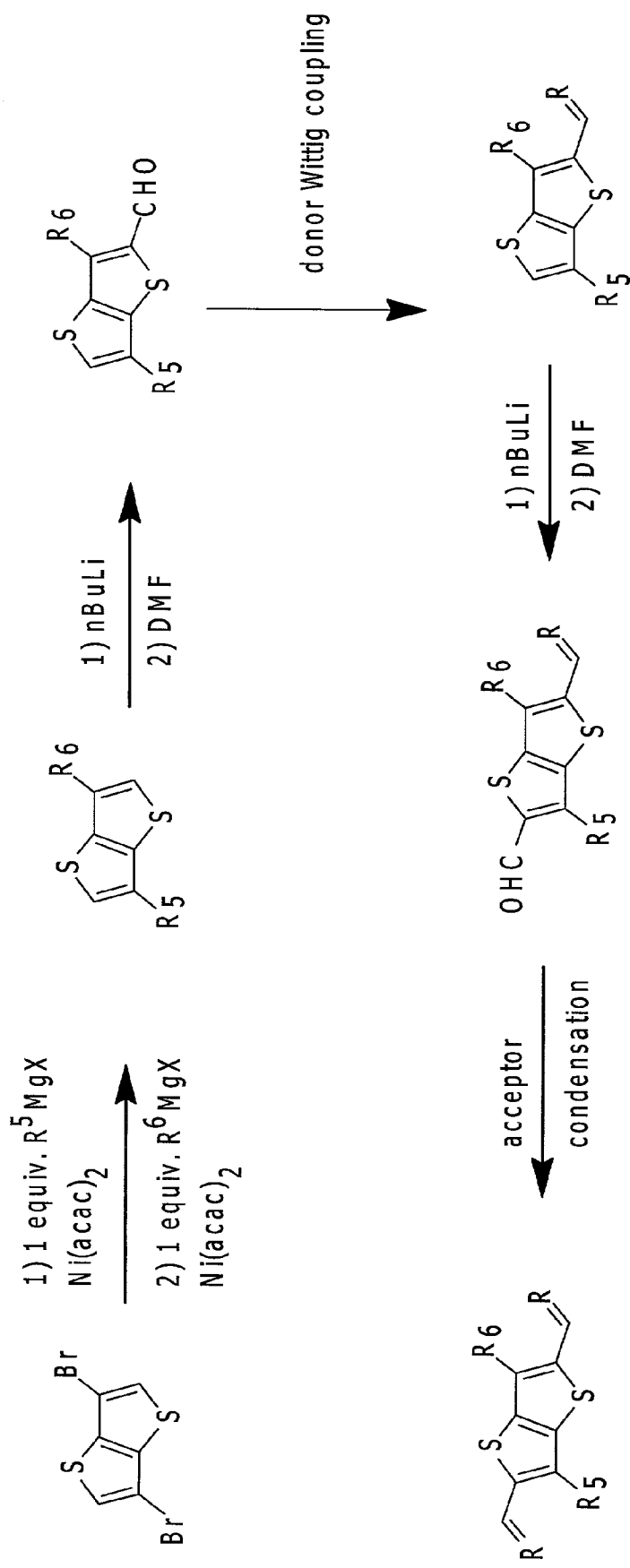
FIG. 4 is a synthetic scheme for the preparation of representative fused dithiophene bridges of the invention.
Figure 5:
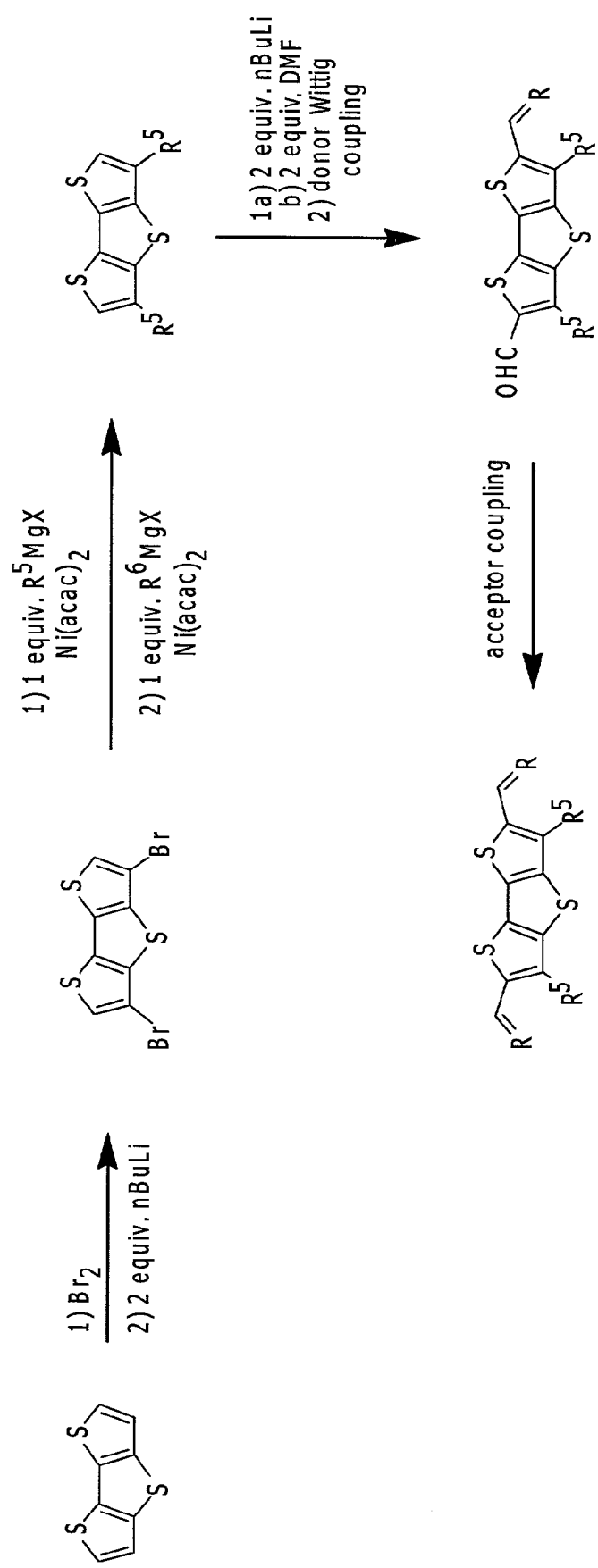
FIG. 5 is a synthetic scheme for the preparation of representative fused trithiophene bridges of the invention.
Figure 6:
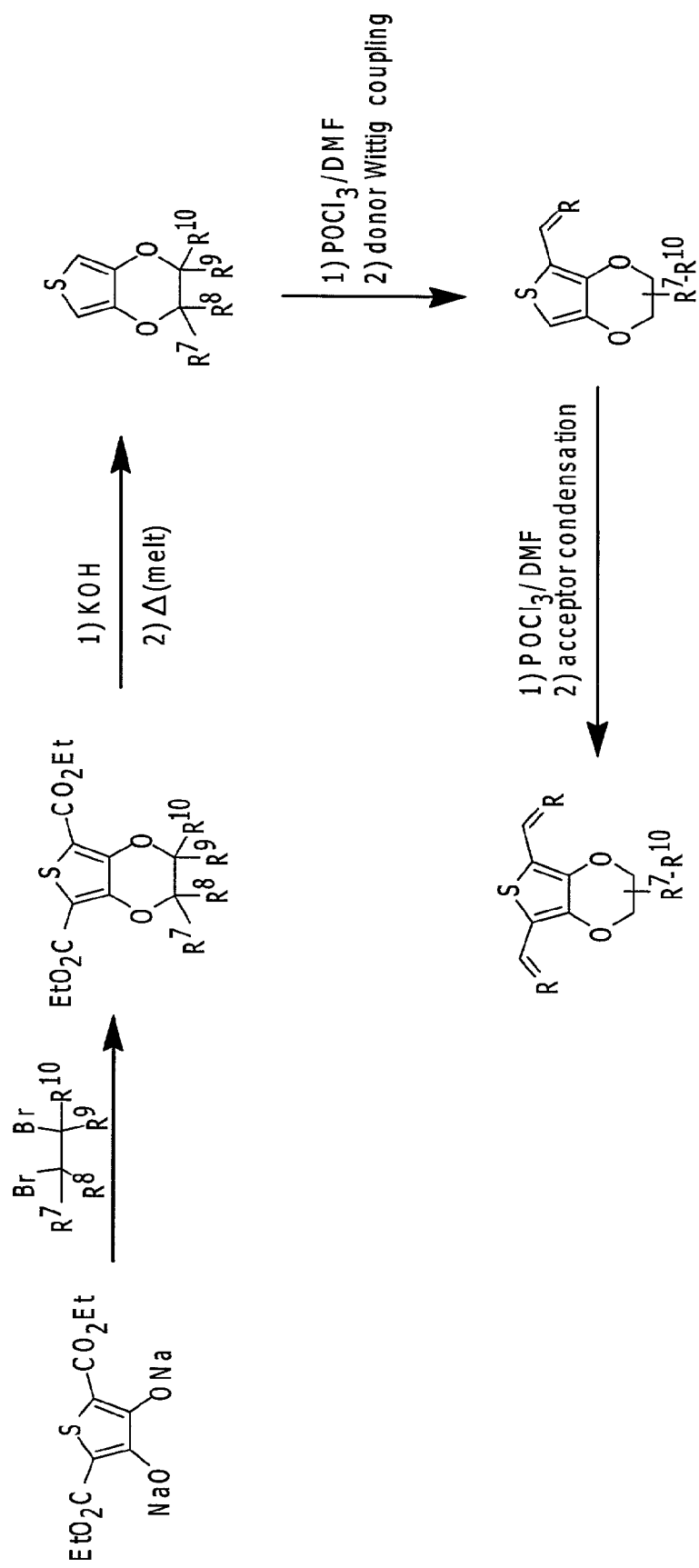
FIG. 6 is a synthetic scheme for the preparation of representative thiophene substituted bridges of the invention.
Figure 7:
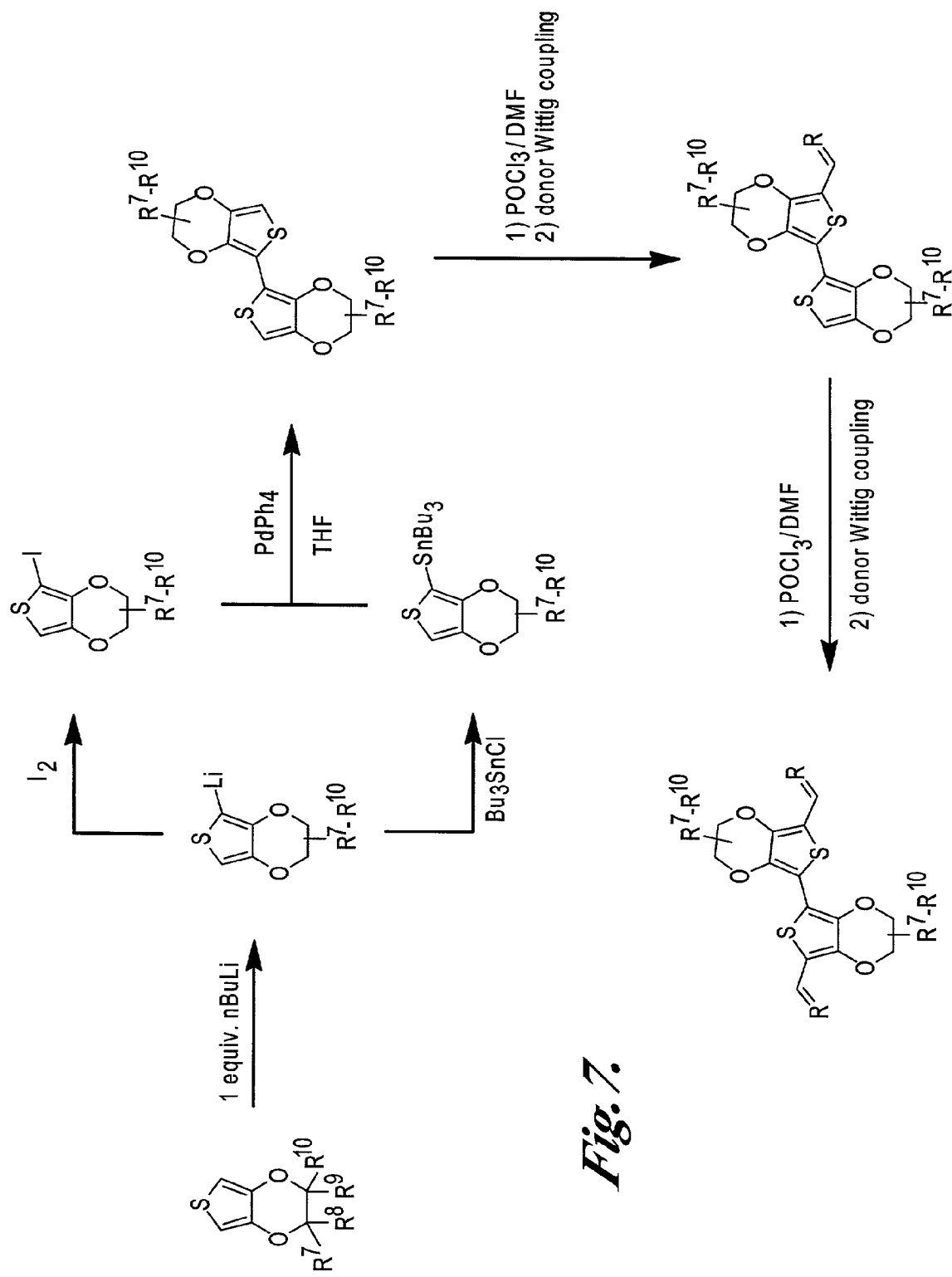
FIG. 7 is a synthetic scheme for the preparation of representative dithiophene substituted bridges of the invention.

$R_{10}$ are fluorine, or wherein $R_7$, $R_8$, and $R_9$ are fluorine and $R_{10}$ is a trifluoromethyl group; and R represents a functional group capable of forming a covalent bond with the donor and acceptor portions of the chromophore, or when the donor is incorporated into a chromophore, R represents the rest of the chromophore. A synthetic scheme for the preparation of this class of bridge is presented in FIG. 7. Chromophores that include the bridge are illustrated in FIGS. 2H and 2I.

It will be appreciated that chromophores of the invention can include any combination of donors, bridges, donors, substituted donors, substituted bridges, and substituted acceptors, described herein.

As used herein, the term "alkyl group" refers to branched or straight chain alkyl groups. Alkyl groups can include from one to ten or more carbon atoms that are unsubstituted or substituted. The alkyl groups can include substituents for coupling to a dendron, substituents for coupling to a crosslinking group, or crosslinking substituents. Representative alkyl groups include, for example, methyl, ethyl, n-propyl, isopropyl, n-butyl, s-butyl, isobutyl, t-butyl, n-pentyl, and n-hexyl groups, fluorinated alkyl groups, among others. Representative substituents include alkyl groups, hydroxyl groups, and silyl groups, among others.

Chromophores. Representative chromophore structures include the donors, bridges, and acceptors noted above, illustrated in the figures, and described below.

In one embodiment, the chromophore has the structure:

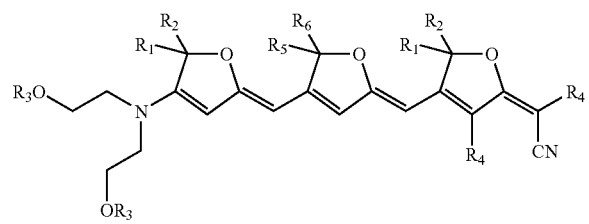

wherein $R_1$ and $R_2$ are alkyl groups, $R_3$ is a bulky substituent, $R_4$ is independently selected from F, CN, and $CF_3$, and $R_5$ and $R_6$ are selected from alkyl and silyl groups, such as t-butyldimethyl silyl and perfluoropropyldimethyl silyl group.

A representative chromophore having the above structure includes:

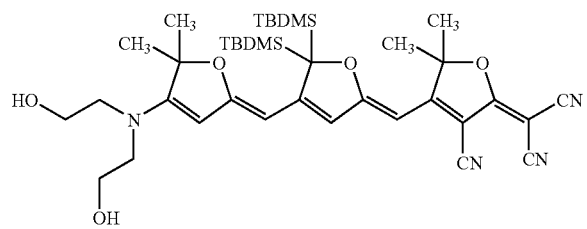

wherein TBDMS is a t-butyldimethylsilyl group.

In certain embodiments, the chromophore is crosslinkable and, in other embodiments, the chromophore is double-ended-crosslinkable. The term "double-ended-crosslinkable" refers to a chromophore in which each end or two or more portions of the chromophore includes a crosslinking group. Crosslinkable chromophores of the invention are illustrated in FIGS. 28–32.

Chromophore-Containing Macromolecular Structures. In another aspect, the present invention provides a macromolecular structure that includes a hyperpolarizable chromophore. The macromolecular structure enhances chemical and photochemical stability and maximizes the electro-optic coefficient by preventing intermolecular close approach. For these macromolecular structures, electro-optic coefficient v. chromophore number density curves show steeper slopes than for simple chromophores and with linearity maintained compared to other prior art chromophores. The macromolecular structures can include single or multiple chromophores. The macromolecular structures can be crosslinked.

Representative macromolecular structures include dendrimers and dendritic polymers that incorporate hyperpolarizable chromophores. These dendrimers and dendritic polymers can be based on any of the chromophores described above. Representative dendrimer-containing chromphores (dendrimer functionalized chromophores) of the invention are illustrated in FIGS. 26 and 28–32 The dendrimer and dendritic polymers can include one or more chromophores.

In one embodiment, the chromophore-containing dendrimer is a Tomalia dendrimer. In another embodiment, the chromophore-containing dendrimer is a convergently synthesized dendrimer. Such an embodiment can include multiple chromophores.

Chromophore-containing dendrimers of the invention can be prepared by a variety of synthetic methods. Suitable synthetic methods include those as generally described in U.S. Pat. No. 4,558,120, entitled "Dense Star Polymer"; U.S. Pat. No. 5,527,524, entitled "Dense Star Polymer Conjugate"; and U.S. Pat. No. 5,837,865, entitled "Phosphorescent Dendritic Macromolecular Compounds for Imaging Tissue Oxygen".

Chromophore-containing dendrimers can be incorporated into polymers, as discussed below, and used in electro-optic devices. In one embodiment, the dendrimer is incorporated into a polymer host to provide a composite. In another embodiment, the dendrimer is covalently coupled to the polymer host by, for example, crosslinking.

Alternatively, chromophore-containing dendrimers can be used in electro-optic devices directly without a host polymer. In such an embodiment, the dendrimer is crosslinked to form a lattice. Thus, in another embodiment, the invention provides a crosslinkable dendrimer. In this embodiment, the dendrimer is crosslinked to other dendrimers to provide a lattice that does not include a polymer host. Accordingly, in another aspect of the invention, a lattice is provided that is derived from crosslinkable dendrimers. The lattice is a polymer-like lattice and can be a hardened lattice.

Chromophore-Containing Polymers. In another aspect of the invention, chromophore-containing polymers are provided. These polymers can include any one of the chromophores described above, including the chromophore-containing macromolecular structures. In one embodiment, the chromophore is physically incorporated into a polymer to provide a composite. In another embodiment, the chromophore is covalently incorporated into the polymer by, for example, crosslinking. In one embodiment, the chromophore is crosslinked to the polymer in more than one position, for example, a double-ended crosslinked chromophore.

Generally, once a chromophore of appropriate optical nonlinearity ($\mu\beta$), optical absorption, and stability has been identified, the material is processed into a polymeric material that contains acentrically-aligned chromophores. The process polymeric material can then be translated by, for example, reactive ion etching or photolithography into a waveguide structure that can be integrated with appropriate drive electronics and silica fiber transmission lines. See Dalton et al., "Synthesis and Processing of Improved Organic Second-Order Nonlinear Optical Materials for Applications in Photonics", *Chemistry of Materials*, Vol. 7, No. 6, pp. 1060–1081 (1995).

To withstand processing conditions and operational conditions (optical power levels at 1.3 and 1.55 microns), chromophore-containing polymers are hardened subsequent to electric field poling to withstand temperatures of 90° C. or greater. As noted above, in certain embodiments, the chromophores include reactive functional groups (e.g., hydroxyl groups) that permit processing into hardened polymer matrices. See Dalton et al. (1995). When thermosetting chemical reactions are employed to lock-in electric field poling-induced acentric order, a stepped poling procedure can be used in which temperature and electric field strength is increased in successive steps to optimize material electro-optic activity. See Kalluri et al., "Improved Poling and Thermal Stability of Sol-Gel Nonlinear Optical Polymers", *Applied Physics Letters*, Vol. 65, pp. 2651–2653 (1994). Low loss optical waveguides can be fabricated in polymeric waveguides containing acentrically ordered chromophores. A variety of other techniques can be utilized to fabricate waveguides including, for example, laser ablation, multi-color photolithography, and spatially selective poling.

The chromophores can be incorporated into a variety of host materials including, for example, poly(methylmethacrylate) (PMMA); polyimide; polyamic acid; polystyrene; poly(urethane) (PU); and poly[bisphenol A carbonate-co-4,4'-(3,3,5-trimethylcyclohexylidene)diphenol], amorphous polycarbonate (APC); among others.

In summary, suitable methods for incorporating a chromophore into a polymer include the steps of combining the chromophore with the polymer; electric field poling of the chromophore/polymer mixture to acentrically align chromophores; followed by crosslinking, curing, and hardening the chromophore-containing polymer.

Electro-optic Modulator Devices. In a further aspect, the present invention provides electro-optic modulator devices and electro-optic modulator devices that include the chromophores of the invention. The chromophores of the invention can be readily fabricated into electro-optic modulator devices using methods and procedures previously developed for other chromophores. The chromophores of the invention are acceptable for all processing steps necessary for the fabrication of devices. For example, the modulator can be fabricated by spinning the organic chromophore and host polymer onto any substrate.

In one embodiment, the invention provides an electro-optic polymer based polarization controller for optical connections. Waveguide devices based on electro-optic polymers can be utilized in optical signal processing and communication. High speed modulators have excellent velocity matching between microwave and optical signals. In the lightwave signal transmission, the polarization state of light is not maintained when a standard single-modefiber is used. Thus, polarization independent electro-optic devices are preferred to reduce system complexity caused by adaptive polarization controlling unit. In one embodiment, the present invention provides a TE-TM mode converter in a polymer waveguide. Previous TE-TM mode converters have been fabricated in lithium niobate and compound semiconductor waveguides. The use of electro-optic polymers containing, for example, the chromophores of the invention, in waveguides provides devices with tens of GHz modulation bandwidth. A representative device uses an active TE-TM mode converter by introducing a birefringent electro-optic polymer with a high electro-optic coefficient as the waveguide as the waveguide core material whose poling induced optic axis has a rotation angle of 45 degrees to the waveguide substrate plane. In a representative device, the chromophore is incorporated into a polycarbonate based host-guest system having an electro-optic coefficient greater than 50 pm/V, good thermal stability, and low optical loss at 1300 and 1550 nm. The high electro-optic coefficient facilitates the operation of the mode converter at sub-volt levels. The mode converter can be used for optical signal processing and communication systems either as a stand-alone device or can be integrated with other devices.

Polymeric waveguide electro-optic modulators can be integrated with semiconductor very large scale integration (VLSI) circuitry to provide advantages related to the chromophores of the invention. See Kalluri et al., "Integration of Polymer Electrooptic Devices on Non-Planar Silicon Integrated Circuits", *Proceedings of the SPIE*, Vol. 2527, pp. 375–383 (1995). Low loss coupling schemes for coupling polymeric modulator waveguides to silica fiber transmission lines can also be used. The large operational bandwidth of polymeric modulators has been demonstrated. See, e.g., Dalton et al., "Low (Sub-1-Volt) Halfwave Voltage Polymeric Electro-optic Modulators Achieved by Controlling Chromophore Shape", *Science*, Vol. 288, pp. 119–122 (2000).

The chromophores of the invention can be employed in conventional electro-optic modulator devices as well as other modulator devices. Representative electro-optic modulator devices include waveguides, switches, beam steerers, power splitters. See Dalton et al. (2000). Simple device configurations of the invention include Mach Zehnder modulators, birefringement modulators, and directional couplers. Other electro-optic modulators of the invention include three-dimensional integrated optics. Representative three-dimensional integrated optics using hyperpolarizable chromophores are described in Dalton et al., "Three-Dimensional Integrated Optics Using Polymers", *IEEE Journal of Quantum Electronics*, Vol. 35, No. 8, (1999).

Figure 41:
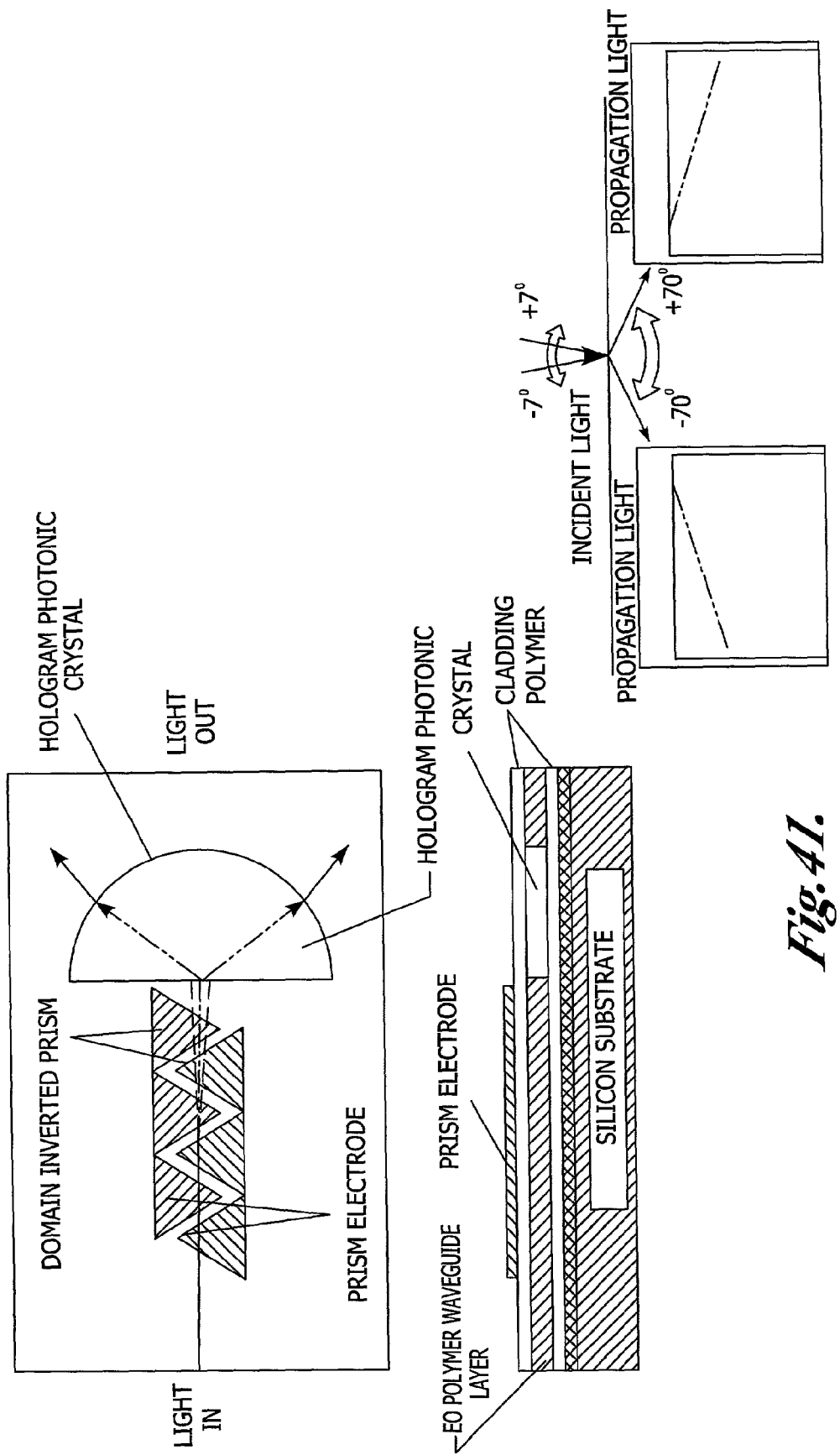
FIG. 41 is an illustration of a representative device formed in accordance with the present invention, a large angle laser beam scanner.
Figure 42:
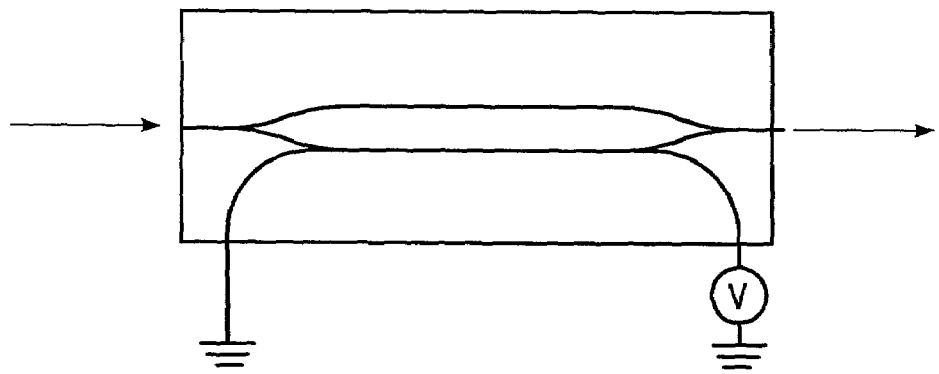
FIG. 42 is an illustration of representative devices formed in accordance with the present invention, a Mach Zehnder modulator, a birefringent modulator, and a directional coupler.
Figure 42:
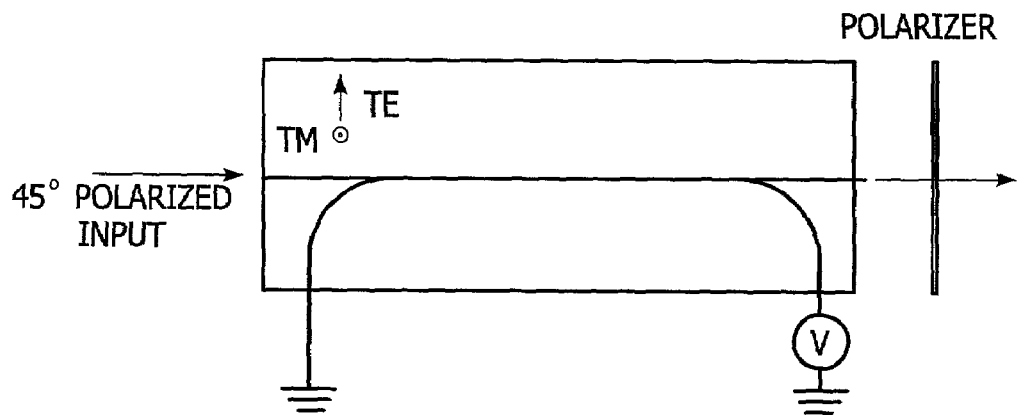
Figure 42:
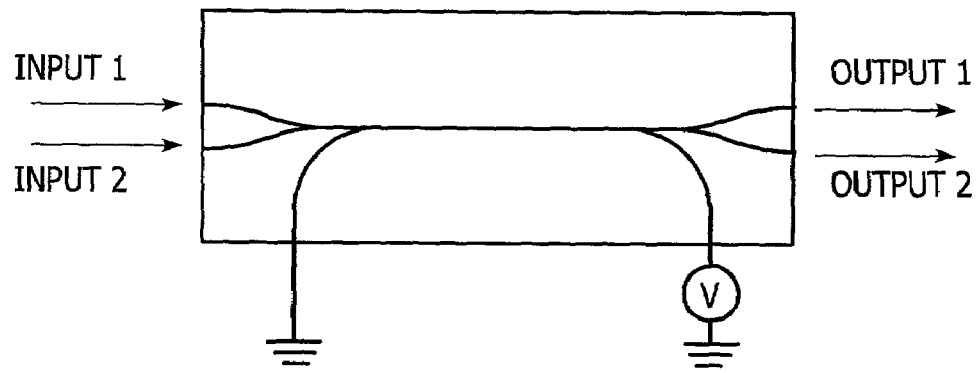
Figure 43:
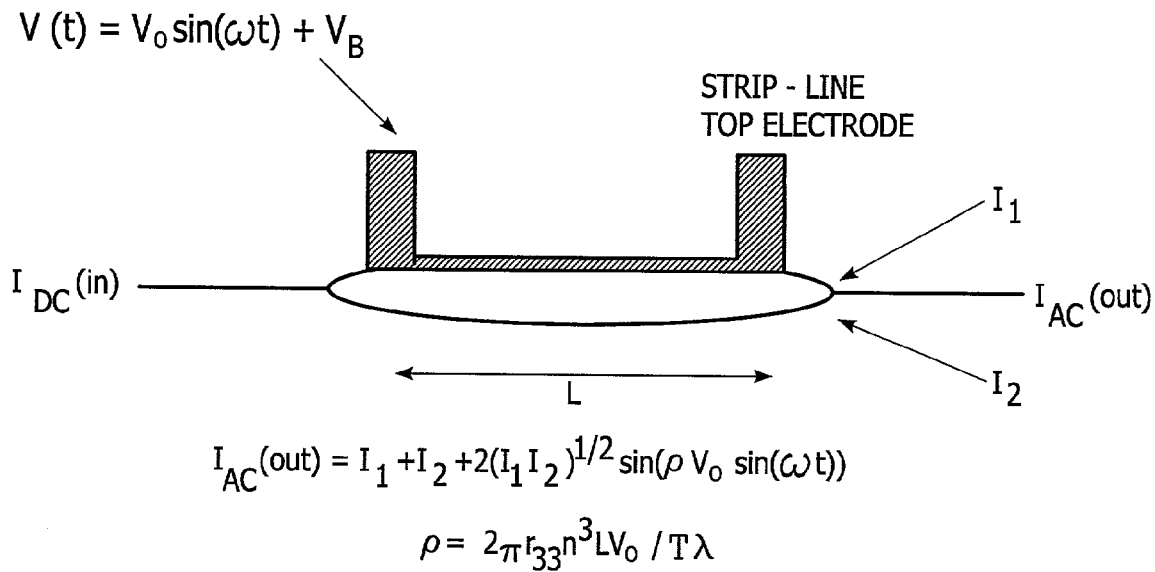
FIG. 43 is an illustration comparing the features of the devices illustrated in FIG. 42.
Figure 44:
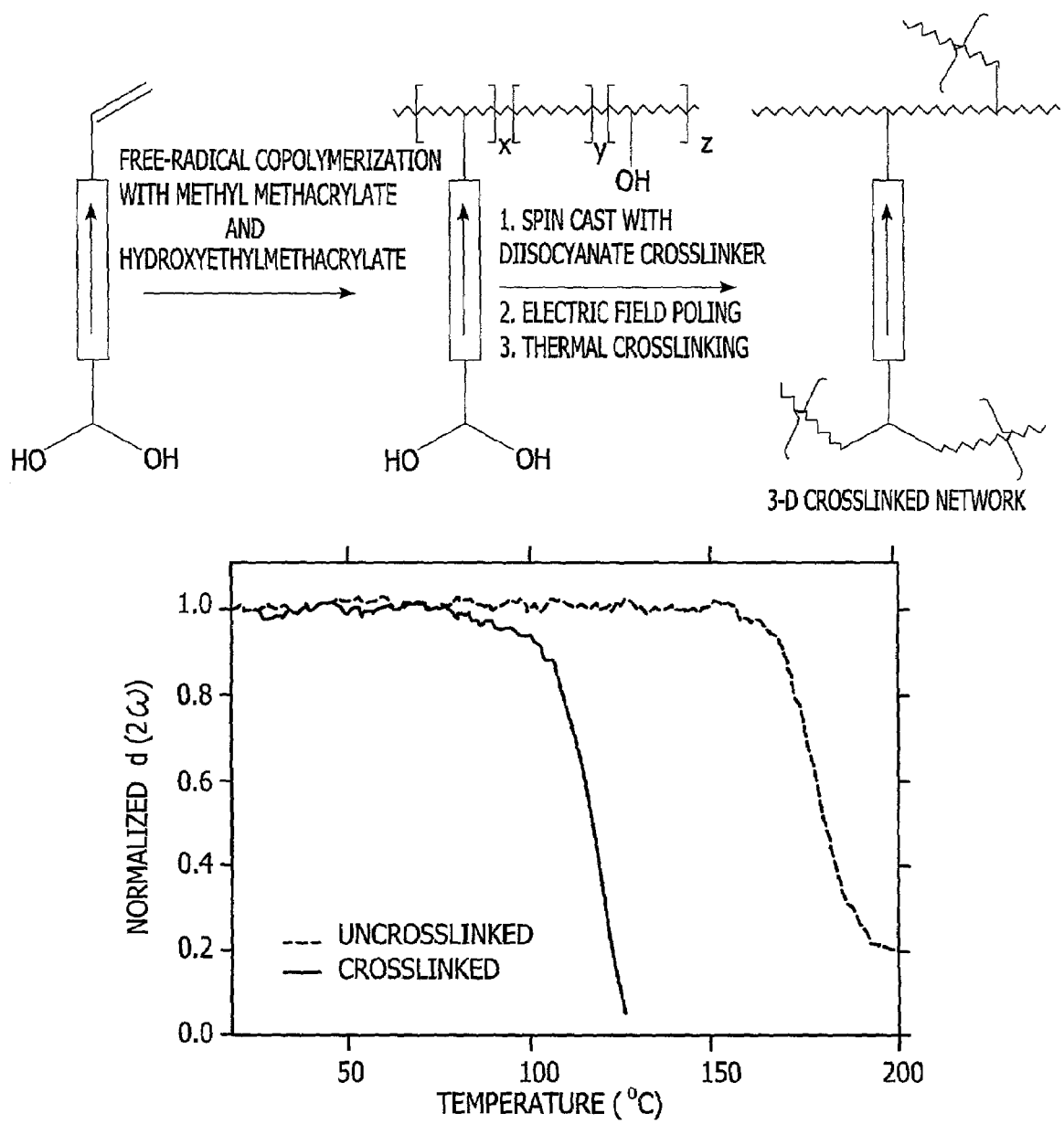
FIG. 44 is an illustration of a lattice hardening scheme.

In another embodiment, the invention provides device structures that amplify the performance of polymeric materials. These devices can include photonic bandgap structures and resonated and cascaded prism structures. These devices can include the chromophore of the invention. A representative device, a large angle laser beam scanner, is illustrated in FIG. 41. In the device, an electro-optic waveguide prism introduces a small deflection beam angle to initialize the beam scanning. The half-circle two-dimensional photonic crystal region is imbedded into the waveguide such that the deflection angle is amplified as the light passes through the crystal region. When the structure has a three-dimensional structure, three-dimensional scanning is provided. As illustrated in FIG. 41, the representative large angle beam steering device, including a chromophore-containing electro-optic polymer together with a cascaded prism, achieves large beam steering (−70° to +70°) with very fast speed and with modest drive voltages.

When processed into electro-optic polymers and/or incorporated into electro-optic devices, the chromophores of the invention provide improved electro-optic device performance. Improved electro-optic device performance includes bandwidths greater than about 100 GHz, drive voltages less than about 2 volts, preferably less than about 1 volt, and optical loss of less than about 1.5 dB/cm, preferably less than about 1.0 dB/cm, at 1.3 micron.

The modulators can be configured to operate at high frequencies and in arrays for applications in communications and network connections. The modulators can be implemented in series and parallel combinations. The modulators can be used in a multitude of ways including in phased array radar; signal processing; optical network switching; beam steering; optical computing; sensor technology, including fiber-optic medical sensor applications; telecommunications, including satellite communications; and cable television capacity.

The materials and methods of the present invention can be useful in a variety of electrooptic (EO) applications. In addition, these materials and methods may be applied to polymer transistors or other active or passive electronic devices, as well as OLED (organic light emitting diode) or LCD (liquid crystal display) applications The use of organic polymers in integrated optics and optical communication systems containing optical fibers and routers has been previously described. The compounds, molecular components, polymers, compositions, etc. of the present invention (hereinafter, "materials") may be used in place of currently used materials such as lithium niobate in most type of integrated optics devices, optical computing applications, and optical communication systems. For instance, the materials of the invention may be fabricated into switches, modulators, waveguides, or other electrooptical devices.

For example, in optical communication systems devices fabricated from the materials of the invention may be incorporated into routers for optical communication systems or waveguides for optical communication systems or for optical switching or computing applications. Because the materials are generally less demanding than currently used materials, devices made from such polymers may be more highly integrated, as described in U.S. Pat. No. 6,049,641, which is incorporated herein by reference. Additionally, such materials may be used in periodically poled applications as well as certain displays, as described in U.S. Pat. No. 5,911,018, which is incorporated herein by reference.

Techniques to prepare components of optical communication systems from optically transmissive materials have been previously described, and may be utilized to prepare such components from materials provided by the present invention. Many articles and patents describe suitable techniques, and reference other articles and patents that describe suitable techniques, where the following articles and patents are exemplary:

Eldada, L. and Shacklette, L. "Advances in Polymer Integrated Optics" *IEEE Journal of Selected Topics in Quantum Electronics*, Vol. 6, No. 1, January/February 2000, pp. 54–68; Wooten, E. L. et al. "A Review of Lithium Niobate Modulators for Fiber-Optic Communication Systems" *IEEE Journal of Selected Topics in Quantum Electronics*, Vol. 6, No. 1, January/February 2000, pp. 69–82; Heismann, F. et al. "Lithium niobate integrated optics: Selected contemporary devices and system applications" *Optical Fiber Telecommunications* III B, Kaminow and Koch, Eds. New York: Academic, 1997, pp. 377–462; Murphy, E. "Photonic switching" *Optical Fiber Telecommunications* III B, Kaminow and Koch, Eds. New York: Academic, 1997, pp. 463–501; Murphy, E. *Integrated Optical Circuits and Components: Design and Applications*. New York: Marcel Dekker, August 1999; Dalton, L. et al. "Polymeric Electro-optic Modulators: From Chromophore Design to Integration with Semiconductor Very Large Scale Integration Electronics and Silica Fiber Optics" *Ind. Eng. Chem. Res.* 1999, 38, 8–33; Dalton, L., et al. "From molecules to opto-chips: organic electro-optic materials" *J. Mater. Chem.*, 1999, 9, 1905–1920; Liakatas, I. et al. "Importance of intermolecular interactions in the nonlinear optical properties of poled polymers" *Applied Physics Letters* Vol. 76, No. 11 13 March 2000 pp. 1368–1370; Cai, C. et al. "Donor-Acceptor-Substituted Phenylethenyl Bithiophenes: Highly Efficient and Stable Nonlinear Optical Chromophores" *Organic Letters* 1999, Vol. 1, No. 11 pp. 1847–1849; Razna J. et al. "NLO properties of polymeric Langmuir-Blodgett films of sulfonamide-substituted azobenzenes" *J. of Materials Chemistry*, 1999, 9, 1693–1698; Van den Broeck, K. et al. "Synthesis and nonlinear optical properties of high glass transition polyimides" *Macromol. Chem. Phys.* Vol. 200, pp. 2629–2635, 1999; Jiang, H. and Kakkar, A. K. "Functionalized Siloxane-Linked Polymers for Second-Order Nonlinear Optics" *Macromolecules* 1998, Vol. 31, pp. 2501–2508; Jen. A. K-Y. "High-Performance Polyquinolines with Pendent High-Temperature Chromophores for Second-Order Nonlinear Optics" *Chem. Mater.* 1998, Vol. 10, pp. 471–473; "Nonlinear Optics of Organic Molecules and Polymers" Edited by Hari Singh Nalwa and Seizo Miyata, CRC Press, 1997; Cheng Zhang, Ph.D. Dissertation, University of Southern California, 1999; Galina Todorova, Ph.D. Dissertation, University of Southern California, 2000; U.S. Pat. Nos. 5,272,218; 5,276,745; 5,286,872; 5,288,816; 5,290,485; 5,290,630; 5,290,824; 5,291,574; 5,298,588; 5,310,918; 5,312,565; 5,322,986; 5,326,661; 5,334,333; 5,338,481; 5,352,566; 5,354,511; 5,359,072; 5,360,582; 5,371,173; 5,371,817; 5,374,734; 5,381,507; 5,383,050; 5,384,378; 5,384,883; 5,387,629; 5,395,556; 5,397,508; 5,397,642; 5,399,664; 5,403,936; 5,405,926; 5,406,406; 5,408,009; 5,410,630; 5,414,791; 5,418,871; 5,420,172; 5,443,895; 5,434,699; 5,442,089; 5,443,758; 5,445,854; 5,447,662; 5,460,907; 5,465,310; 5,466,397; 5,467,421; 5,483,005; 5,484,550; 5,484,821; 5,500,156; 5,501,821; 5,507,974; 5,514,799; 5,514,807; 5,517,350; 5,520,968; 5,521,277; 5,526,450; 5,532,320; 5,534,201; 5,534,613; 5,535,048; 5,536,866; 5,547,705; 5,547,763; 5,557,699; 5,561,733; 5,578,251; 5,588,083; 5,594,075; 5,604,038; 5,604,292; 5,605,726; 5,612,387; 5,622,654; 5,633,337; 5,637,717; 5,649,045; 5,663,308; 5,670,090; 5,670,091;

5,670,603; 5,676,884; 5,679,763; 5,688,906; 5,693,744; 5,707,544; 5,714,304; 5,718,845; 5,726,317; 5,729,641; 5,736,592; 5,738,806; 5,741,442; 5,745,613; 5,746,949; 5,759,447; 5,764,820; 5,770,121; 5,76,374; 5,776,375; 5,777,089; 5,783,306; 5,783,649; 5,800,733; 5,804,101; 5,807,974; 5,811,507; 5,830,988; 5,831,259; 5,834,100; 5,834,575; 5,837,783; 5,844,052; 5,847,032; 5,851,424; 5,851,427; 5,856,384; 5,861,976; 5,862,276; 5,872,882; 5,881,083; 5,882,785; 5,883,259; 5,889,131; 5,892,857; 5,901,259; 5,903,330; 5,908,916; 5,930,017; 5,930,412; 5,935,491; 5,937,115; 5,937,341; 5,940,417; 5,943,154; 5,943,464; 5,948,322; 5,948,915; 5,949,943; 5,953,469; 5,959,159; 5,959,756; 5,962,658; 5,963,683; 5,966,233; 5,970,185; 5,970,186; 5,982,958; 5,982,961; 5,985,084; 5,987,202; 5,993,700; 6,001,958; 6,005,058; 6,005,707; 6,013,748; 6,017,470; 6,020,457; 6,022,671; 6,025,453; 6,026,205; 6,033,773; 6,033,774; 6,037,105; 6,041,157; 6,045,888; 6,047,095; 6,048,928; 6,051,722; 6,061,481; 6,061,487; 6,067,186; 6,072,920; 6,081,632; 6,081,634; 6,081,794; 6,086,794; 6,090,322; and 6,091,879.

Thus, the foregoing references provide instruction and guidance to fabricate waveguides from materials of the present invention using, e.g., direct photolithography, reactive ion etching, excimer laser ablation, molding, conventional mask photolithography, ablative laser writing, or embossing (e.g., soft embossing). The foregoing references also disclose electron acceptors, electron donors, and electron bridges that may be incorporated into chromophores of the present invention that also incorporate an electron acceptor and/or electron donor and/or electron bridge of the present invention.

Components of optical communication systems that may be fabricated, in whole or part, with materials of the present invention include, without limitation, straight waveguides, bends, single-mode splitters, couplers (including directional couplers, MMI couplers, star couplers), routers, filters (including wavelength filters), switches, modulators (optical and electrooptical, e.g., birefringent modulator, the Mach-Zender interferometer, and directional and evanescent coupler), arrays (including long, high-density waveguide arrays), optical interconnects, optochips, single-mode DWDM components, and gratings. The materials of the present invention may be used with, for example, wafer-level processing, as applied in, for example, vertical cavity surface emitting laser (VCSEL) and CMOS technologies.

In many applications, the materials of the present invention may be used in lieu of lithium niobate, gallium arsenide and other inorganic materials that currently find use as light-transmissive materials in optical communication systems.

The materials of the present invention may be used in telecommunication, data communication, signal processing, information processing, and radar system devices and thus may be used in communication methods relying, at least in part, on the optical transmission of information. Thus, the present invention provides a method of communication comprising transmitting information by light, the light transmitted at least in part through a material of the present invention.

In various embodiments, the present invention provides:

An EO device comprising at least one of a chromophore, a composition, or a composition prepared by a process according to the present invention;

A waveguide comprising at least one of a chromophore, a composition, or a composition prepared by a process, according to the present invention;

An optical switch comprising at least one of a chromophore, a composition, or a composition prepared by a process, according to the present invention;

An optical modulator comprising at least one of a chromophore, a composition, or a composition prepared by a process, according to the present invention;

An optical coupler comprising at least one of a chromophore, a composition, or a composition prepared by a process, according to the present invention;

An optical router comprising at least one of a chromophore, a composition, or a composition prepared by a process, according to the present invention;

A communications system comprising at least one of a chromophore, a composition, or a composition prepared by a process, according to the present invention;

A method of data transmission comprising transmitting light through at least one of a chromophore, a composition, or a composition prepared by a process, according to the present invention;

A method of telecommunication comprising transmitting light through at least one of a chromophore, a composition, or a composition prepared by a process, according to the present invention;

A method of transmitting light comprising directing light through or via at least one of a chromophore, a composition, or a composition prepared by a process, according to the present invention;

A method of routing light through an optical system comprising transmitting light through or via at least one of a chromophore, a composition, or a composition prepared by a process, according to the present invention;

An interferometric optical modulator or switch, comprising: 1) an input waveguide; 2) an output waveguide; 3) a first leg having a first end and a second end, the first leg being coupled to the input waveguide at the first end and to the output waveguide at the second end; and 4) and a second leg having a first end and a second end, the second leg being coupled to the input waveguide at the first end and to the output waveguide at the second end, wherein at least one of the first and second legs includes a composition of matter according to the present invention;

An optical modulator or switch, comprising: 1) an input; 2) an output; 3) a first waveguide extending between the input and output; and 4) a second waveguide aligned to the first waveguide and positioned for evanescent coupling to the first waveguide; wherein at least one of the first and second legs includes a composition of matter according to the present invention. The modulator or switch may further including an electrode positioned to produce an electric field across the first or second waveguide;

An optical router comprising a plurality of switches, wherein each switch includes: 1) an input; 2) an output; 3) a first waveguide extending between the input and output; and 4) a second waveguide aligned to the first waveguide and positioned for evanescent coupling to the first waveguide; wherein at least one of the first and second legs includes a composition of matter according to the present invention. The plurality of switches may optionally be arranged in an array of rows and columns.

The following examples are provide for the purpose of illustrating, not limiting, the invention.

EXAMPLES

General Materials and Methods. In the following examples, the solvents and chemicals used were purchased from Aldrich, Acros and other chemical companies. They were analytical reagent grade unless otherwise noted. All starting materials were obtained from commerical sources and were deemed sufficiently pure to use without further purification unless otherwise noted. Fresh dry THF was obtained from standard drying procedures and equipment. All $^1$H NMR spectra were conducted on a Bruker 200 FT NMR. The chemical shifts are referenced to tetramethylsilane (TMS) internal standard. All reactions involving organolithium reagents were carried out under dry, oxygen-free, nitrogen or argon atmosphere. Air-sensitive reagents were transferred via cannula needle. Column chromatography was performed on Natland 200–400 mesh silica gel or on 70–230 mesh Lancaster silica gel 60. All TLC was performed on Whitman 250 μm layer plates. Melting points were determined on a Mel-Temp® melting point apparatus and were not corrected. All mass spectroscopy data was performed by the technical personnel in the Department of Medicinal Chemistry Mass Spectroscopy Facility at the University of Washington.

Example 1

The Preparation of a Representative Chromophore: Amine Donor, Cyanofuran Acceptor, Thiophene-Containing Bridge In this example, the preparation of a representative chromophore of the invention is described. The chromophore includes a triphenyl amine donor, a 2-dicyanomethylen-3-cyano-4,5,5-trimethyl-2,5-dihydrofuran acceptor, and a thiophene-containing bridge. The overall synthetic scheme is illustrated in FIG. 8. Referring to FIG. 8, the triphenylamine Wittig salt is reacted with the thiophene aldehyde to provide an intermediate donor-bridge component that is further reacted with the cyanofuran to provide the chromophore.

Synthesis of Bis-(4-methoxyphenyl){4-[(Triphenylphosphonium bromide)methyl]phenyl)amine (1)

Figure 9:
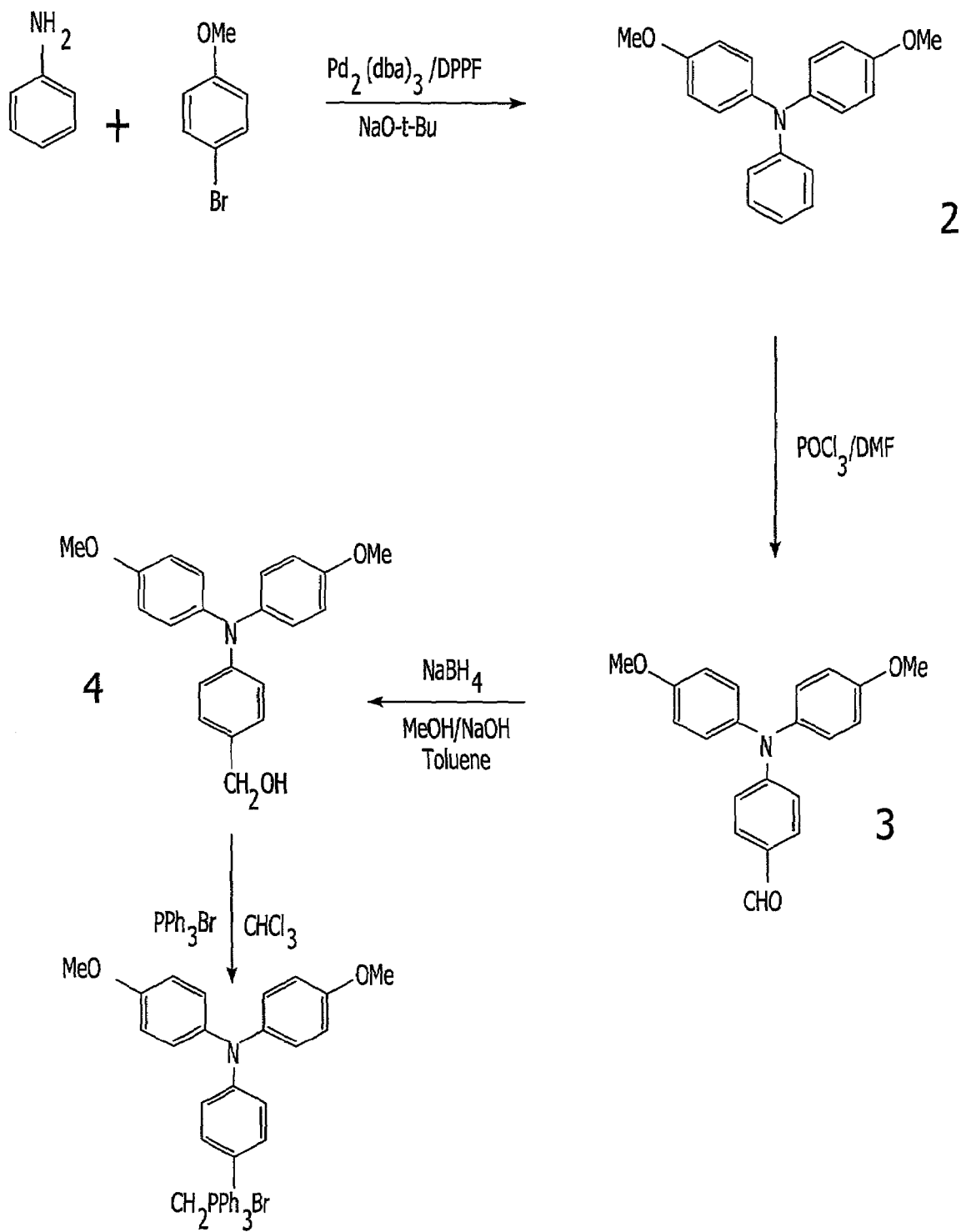
FIG. 9 is a synthetic scheme for the preparation of a triphenylamine Wittig salt useful in the preparation of the chromophores of the invention.

Bis(4-methoxyphenyl)phenylamine (2). The synthesis of the triphenylamine donor Wittig salt follows the schematic in FIG. 9. To a solution of 4.975 g (5.43 mmol) of tris (dibenzylideneacetone)-dipalladium(0) and 4.519 g (8.15 mmol) of 1,1'-bis(diphenylphosphine)-ferrocene in 680 mL toluene under nitrogen was added 68.46 mL (0.245 mol) of 4-bromoanisole and was allowed to stir for 25 minutes. Then, sodium tert-butoxide (59.36 g, 0.618 mol) and aniline (22.5 mL, 0.236 mol) were added to the solution and stirred at 90° C. for approximately 2 weeks. Thin layer chromatography was used to monitor the complete formation of the decoupled product. The reaction solution was then worked up with brine washings (3×), extracted with ether, and dried over MgSO$_4$. A flash column of 5% ethyl acetate/95% hexanes gave a light brown solid. The still crude product was purified on a column with 1% ethyl acetate/99% hexanes mobile phase to give 21.19 g of white solid. $^1$H NMR (CDCl$_3$): δ3.87 (s, 6H), δ6.87–7.08 (m, 11H), δ7.26 (d, 2H).

4-[bis(4-methoxyphenyl)amino]benaldehyde (3). In an addition funnel, 0.34 mL (3.64 mmol) of POCl$_3$ was added dropwise to a stirred cooled solution at 0° C. containing 0.76 mL (9.84 mmol) of DMF in a three-neck flask and allowed to stir for one hour. The mixture was then allowed to warm to room temperature. A solution of 2 (1.0 g, 3.28 mmol) in 1,2 dichloroethane was then added dropwise. After complete addition, the additional funnel was replaced with a condenser and the solution was heated to 90–95° C. for ~3 hours. After slight cooling, the solution was added dropwise to a solution of NaHCO$_3$. The crude product was extracted with methylene chloride, washed 3× with NaHCO$_3$, and dried over Na$_2$SO$_4$. The crude product was purified with column chromatography with 20% ethyl acetate/80% hexanes as the mobile phase to reveal 1.04 g of viscous bright yellow oil. $^1$H NMR (CDCl$_3$): δ3.99 (s, 6H), δ6.90 (d, 4H), δ7.20 (d, 4H), δ7.61 (d, 2H), δ9.79 (s, 1H).

{4-[bis(4-methoxyphenyl)amino]phenyl}methan-1-ol (4). To a solution of methanol, 14.9 g (45 mmol) of 3 was added and stirred. To a prepared solution of 0.75 g of NaOH in 2.5 mL H$_2$O was added NaBH$_4$ (0.85 g, 22.5 mmol) and 25 mL of methanol. The prepared solution was added to the stirred solution of 3 at 0° C. via an addition funnel. The solution was allowed to stir at room temperature overnight. The solution was then worked up with brine washings (3×), extracted with ether, and dried over MgSO$_4$. Removal of solvent revealed 14.84 g of dark orange oil. The product was used without further purification. $^1$H NMR (CDCl$_3$): δ3.95 (s, 6H), δ4.73(s, 2H), δ6.94 (d, 4H), δ7.07 (d, 4H), δ7.20 (d, 2H), δ7.31 (d, 2H).

Bis-(4-methoxyphenyl){4-[(triphenylphosphonium bromide)methyl]phenyl)amine (1). A solution of 4 (14.84 g, 0.044 mmol) and triphenylphosphonium hydrobromide (13.7 g, 0.040 mmol) in 100 mL of chloroform was placed on an azeotrope distillation apparatus and refluxed to remove water for 2–3 hours. Once cooled to room temperature, the chloroform solution was concentrated via rotary evaporation. The product was precipitated using ether and 27.8 g were isolated by filtration. $^1$H NMR (CDCl$_3$): δ3.80 (s, 6H), δ5.22 (d, 2H), δ6.62 (d, 4H), δ6.79 (d, 4H), δ6.98 (d, 2H), δ7.60–7.81 (m, 15H).

Chromphore Synthesis

Figure 10:
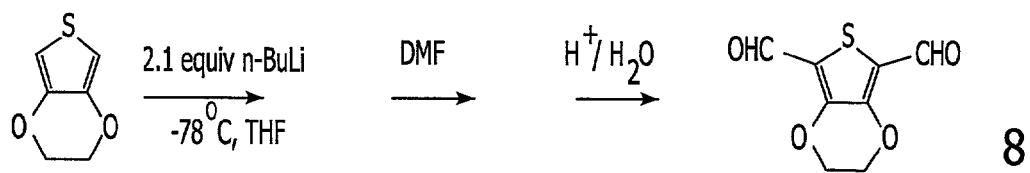
FIG. 10 is a synthetic scheme for the preparation of a substituted thiophene useful in the preparation of the chromophores of the invention.

Donor-Bridge Component 10: The synthesis of the chromophore follows the schematic in FIG. 8. In a 1 L round bottom flask, 6.67 g (10.09 mmol) of 1 and 2.26 g (20.14 mmol) of potassium t-butoxide were added to about 300 mL of methylene chloride. The solution was stirred vigorously for about two minutes at room temperature. Next, 83.70 mg (0.32 mmol) of 18-crown-6 were added to 2 g of 8 and stirred at room temperature for 2–3 hours. Compound 8 (2,3-thiopheno[3,4-e]1,4-dioxane-5,7-dicarbaldehyde) was prepared from the corresponding thiophenodioxane by reaction with two equivalents of n-butyl lithium in THF at −78° C. followed by reaction with dimethylformamide and aqueous acidic work-up as shown in FIG. 10. The solution was filtered over Celite and roto-evaporated. Column chromatography using 5% ethyl acetate in hexane gave 1.1 g of product. $^1$H NMR (CDCl$_3$): δ3.91 (s, 6H), δ4.42–4.59 (m, 2H), δ6.91 (d, 4H), δ7.09 (d, 4H), δ6.99 (d, 2H), δ7.37 (d, 2H), δ7.41 (d, 1H), δ7.12 (d, 1H), δ10.18 (s, 1H), δ4.64 (q, 2H).

Figure 11:
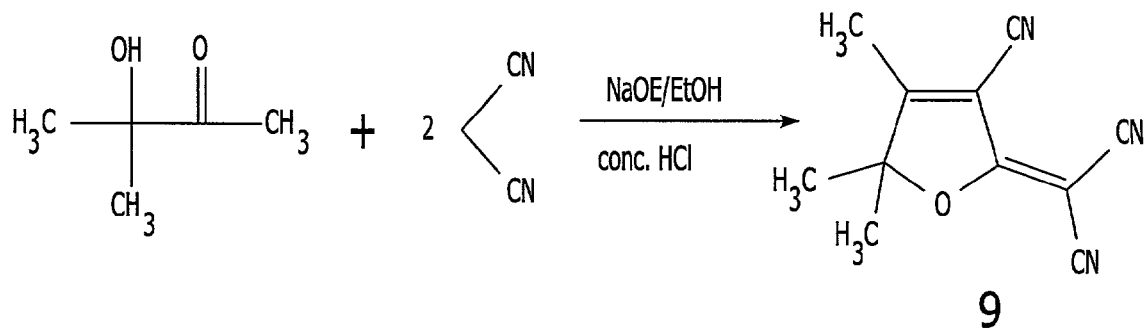
FIG. 11 is a synthetic scheme for the preparation of a substituted cyanofuran useful in the preparation of the chromophores of the invention.

Chromophore 5. To Compound 10 just enough chloroform to dissolve the product was added to a small vial with nearly 1 g of 2-dicyanomethylen-3-cyano-4,5,5-trimethyl-2, 5-dihydrofuran (9). The cyanofuran was prepared by reacting two equivalents of dicyanomethane and sodium ethoxide in ethanol with 3-methyl-3-hydroxybutanone followed by aqueous acidic work-up as shown in FIG. 11. The mixture was stirred and allowed to reflux. Then about 2–3 drops of triethylamine were added, and the solution continued to stir for about 30–45 minutes. It was quenched with ammonium chloride (2×) and washed with chloroform. It was then recrystallized in methanol and purified by column chromatography using 3% ethyl acetate in hexanes to afford 0.6 g of product. $^1$H NMR (CDCl$_3$): δ1.51 (s, 3H), δ1.62 (s, 3H), δ3.83 (s, 6H), δ4.42–4.53 (m, 4H), δ6.85 (d, 1H), δ6.90 (d, 4H), δ7.46 (d, 1H), δ7.13 (d, 1H).

Additional representative thiophene-bridged chromophores of the invention are illustrated in FIG. 14. These chromophores were prepared by synthetic procedures similar to that described above.

Example 2

Figure 12:
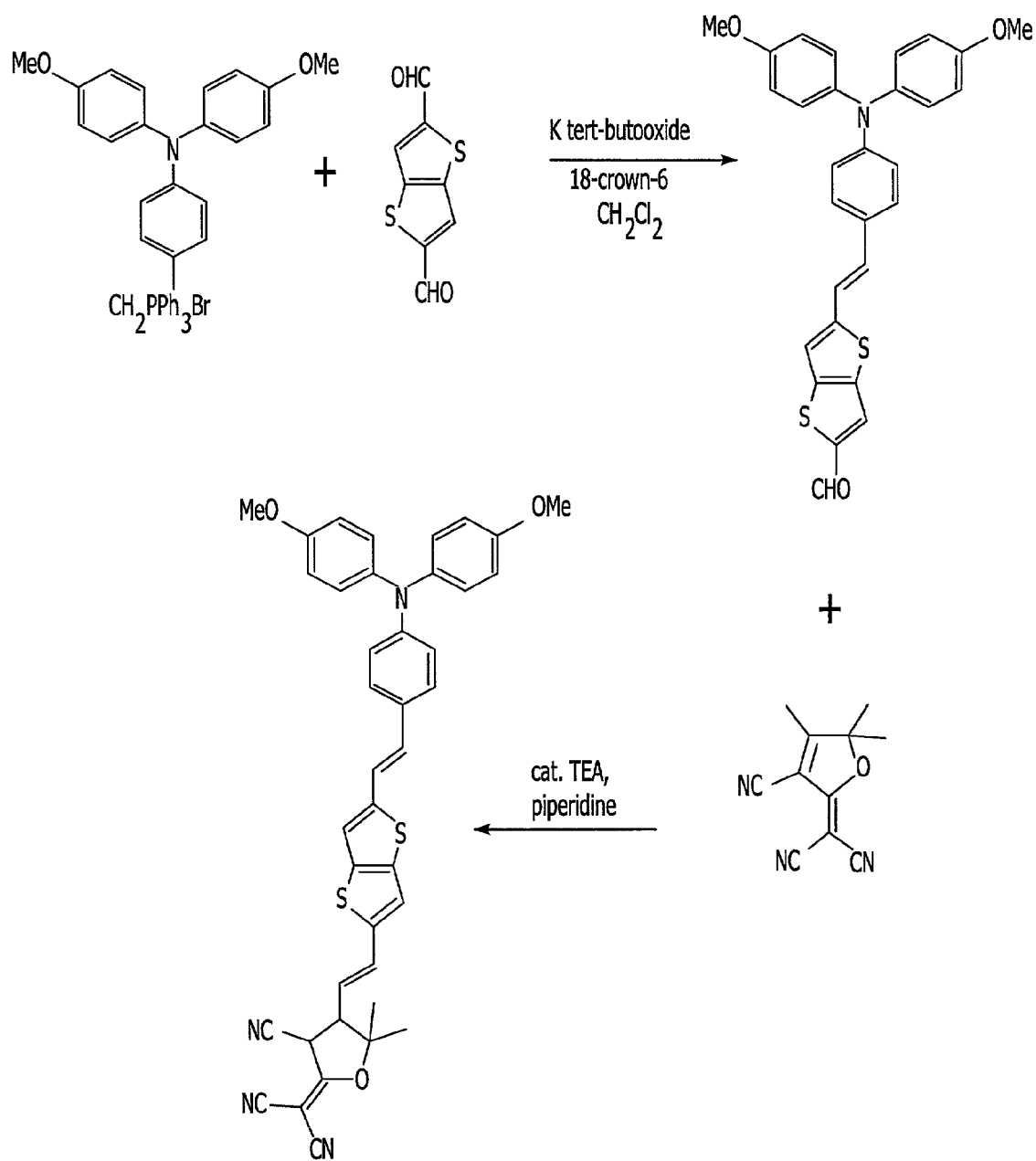
FIG. 12 is a synthetic scheme for the preparation of a representative fused dithiophene-bridged chromophore of the invention.

The Preparation of a Representative Chromophore: Amine Donor, Cyanofuran Acceptor, Fused Dithiophene-Containing Bridge In this example, the preparation of a representative chromophore of the invention is described. The chromophore includes a triphenyl amine donor, a 2-dicyanomethylen-3-cyano-4,5,5-trimethyl-2,5-dihydrofuran acceptor, and a fused dithiophene-containing bridge. The overall synthetic scheme is illustrated in FIG. 12. Referring to FIG. 12, the triphenylamine Wittig salt is reacted with the fused dithiophene aldehyde to provide an intermediate donor-bridge component that is further reacted with the cyanofuran to provide the chromophore.

Figure 13:
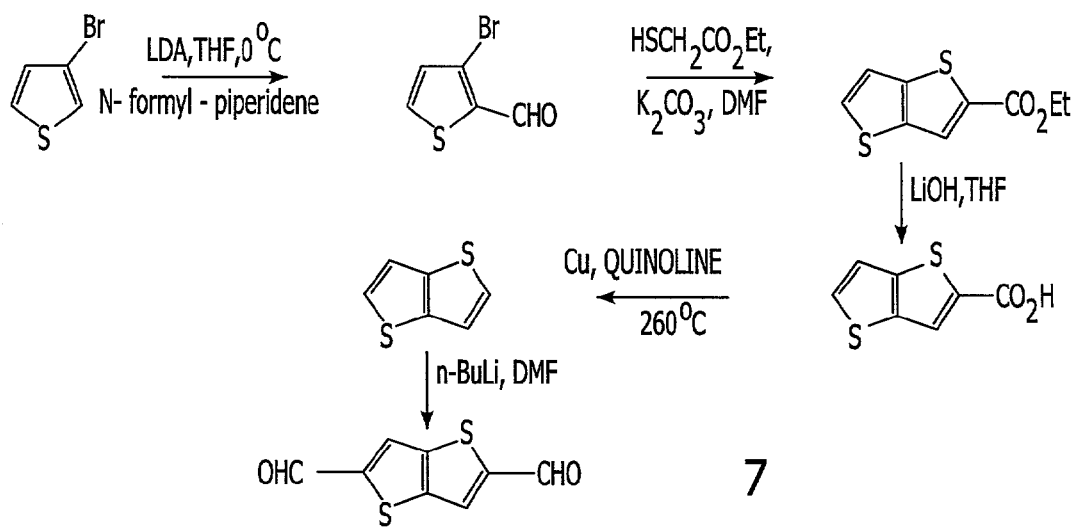
FIG. 13 is a synthetic scheme for the preparation of a fused dithiophene useful in the preparation of the chromophores of the invention.

Donor-Bridge Component 11. In a 1 L round bottom flask, 5.478 (8.28 mmol) of Compound 1 (prepared as described in Example 1) and 1.86 g (16.56 mmol) of potassium tert-butoxide were added to about 300 mL of methylene chloride. The solution was stirred vigorously for about five minutes at room temperature. Next, 82.89 mg (0.31 mmol) of 18-crown-6 were added to 2.5 g of 7 (prepared as shown in FIG. 13) and stirred at room temperature for 2–3 hours. The solution was filtered over Celite and roto-evaperated. Column chromatography using methylene chloride gave 0.9 g of product. $^1$H NMR (CDCl$_3$): δ3.84 (s, 6H), δ6.86 (d, 4H), δ6.83 (d, 4H), δ7.02 (d, 2H), δ7.31 (d, 1H), δ7.46 (d, 2H), δ8.02 (d, 1H), δ9.98 (s, 1H).

Chromophore 6. To Compound 11 just enough chloroform to dissolve the product was added to a small vial with 0.86 g of 2-dicyanomethylen-3-cyano-4,5,5-trimethyl-2,5-dihydrofuran. The mixture was stirred and allowed to reflux. Then about 2–3 drops of triethylamine were added, and the solution continued to stir for about 30–45 minutes. It was quenched with ammonium chloride (2×) and washed with chloroform. It was then recrystallized in methanol and purified by column chromatography using methylene chloride to afford 0.558 g of product. $^1$H NMR (CDCl$_3$): δ1.56 (s, 3H), δ1.69 (s, 3H), δ3.92 (s, 6H), δ6.96 (d, 4H), δ6.95 (d, 4H), δ6.90 (d, 2H), δ8.24 (d, 1H), δ7.93 (d, 1H).

An additional representative fused dithiophene-bridged chromophore of the invention is illustrated in FIG. 14. This chromophore was prepared by a synthetic procedure similar to that described above.

Example 3

Figure 15:
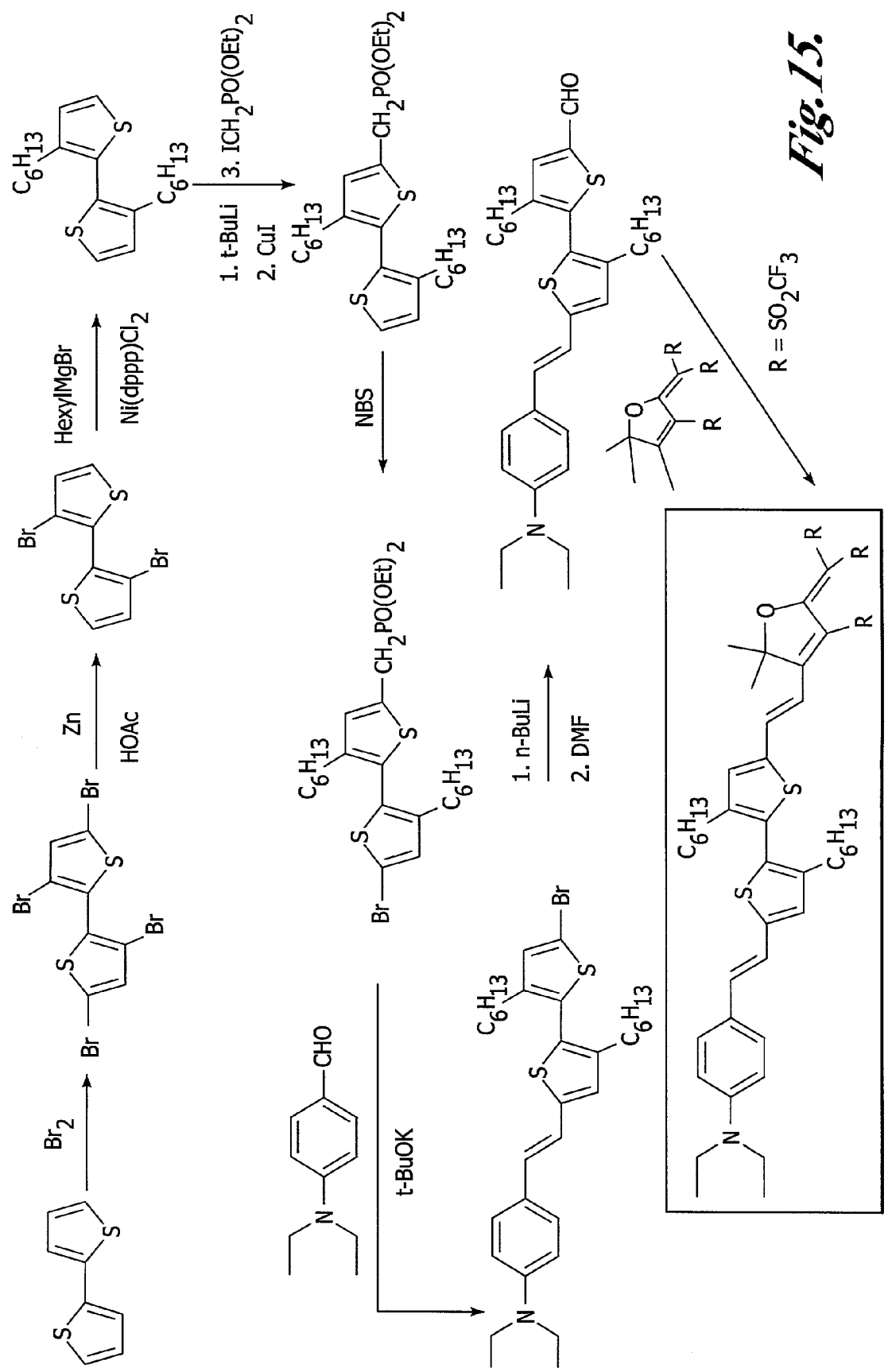
FIG. 15 is a synthetic scheme for the preparation of representative dithiophene-bridged chromophores of the invention.

The Preparation of a Representative Chromophore: Amine Donor, Dithiophene-Containing Bridge, Furan Acceptor In this example, the preparation of a representative chromophore of the invention is described. The chromophore includes a phenyl amine donor, a substituted dithiophene-containing bridge, and a furan acceptor. The overall synthetic scheme is illustrated in FIG. 15. In FIG. 15, R is —SO$_2$CF$_3$. Referring to FIG. 15, n-hexyl substituents are incorporated into the dithiophene to provide an intermediate that is then modified for condensation with the aminophenyl aldehyde. The resulting donor-bridge component is then further functionalized for reaction with an appropriate furan to provide the chromophore. The synthetic procedures follow.

3,3',5,5'-Tetrabromo-2,2'-bithiophene. Bromine (41.2 g, 257.8 mmol) was added dropwise to a solution of 2,2'-bithiophene (10 g, 60.2 mmol) in 250 ml of chloroform at 0–5° C. A light-yellow solid was formed gradually during the addition. The mixture was stirred at room temperature overnight and then refluxed for 2 h. After cooling to room temperature, 100 ml of 10% KOH aqueous solution was added. The resulting mixture was extracted with chloroform to give the crude product. Recrystallization from ethanol/CHCl$_3$ (1:1) afforded a light-yellow crystal in the yield of 87% (25.1 g). $^1$H-NMR (CDCl$_3$, ppm): δ7.05 (s, 2H).

3,3'-Dibromo-2,2'-bithiophene. A mixture of 3,3',5,5'-tetrabromo-2,2'-bithiophene (25 g, 52.3 mmol), ethanol (50 ml), water (50 ml) and glacial acetic acid (100 ml) was heated to reflux. Then the heating oil bath was removed, and zinc powder (13.1 g, 200 mmol) was added in portions at such a rate that the mixture continued to reflux. After the addition was complete, heating was continued, the mixture was refluxed for another 5 h and cooled down to room temperature. The unreacted zinc powder was filtered off and the filtrate was collected, diluted with diethyl ether and then washed twice with water. The ether solution was dried with anhydrous MgSO$_4$ and the solvent was evaporated under reduced pressure. The crude product was recrystallized from hexane to afford a greenish crystal in the yield of 91% (15.3 g). $^1$H-NMR (CDCl$_3$, ppm): δ7.40 (d, 2H, J=5 Hz), 7.11 (d, 2H, J=5 Hz).

3,3'-Dihexyl-2,2'-bithiophene. Hexylmagnesium bromide (100 ml, 2 M solution in diethyl ether, 200 mol) was added dropwise to a solution of 3,3'-dibromo-2,2'-bithiophene (15 g, 46.6 mmol) and Ni(dppp)Cl$_2$ (0.5 g, 0.1 mmol) in 100 ml of diethyl ether at 0C. The reaction was slightly exotherm and a red brown coloration was observed. After stirred and heated for 24 h, the reaction mixture was cautiously poured into a mixture of crushed ice and diluted HCl solution and extracted with ether. The combined extracts were dried over anhydrous MgSO$_4$ and filtered. After removal of the solvent, the residue was vacuum-distilled to give a clear viscous oil (15.6 g, 81%). $^1$H-NMR (CDCl$_3$, ppm): δ7.25 (d, 2H, J=5 Hz), δ6.96 (d, 2H, J=5 Hz), 2.50 (t, 4H), 1.54 (m, 4H), 1.23 (m, 12H), 0.85 (t, 6H).

5-(3,3'-Dihexyl-2,2'-bithienyl)methylphosphonate. A solution of 3,3'-dihexyl-2,2'-bithiophene (8 g, 24 mmol) in 80 ml of anhydrous THF was added over 45 min under argon at −78° C. to a stirred solution of n-butyl lithium (9.6 ml, 2.5 M in hexanes, 24 mmol) in 150 ml of THF. The solution was stirred for 45 min at −78° C., and then transferred, via cannula, into a flask cooled to −20° C. in a dry ice/CCl$_4$ bath, containing CuI (4.6 g, 24 mmol). After 2 h, diethyl iodomethylphosphonate (6.7 g, 24 mmol) was added in one portion, and the solution was reacted at room temperature overnight. The dark reaction mixture was poured into 300 ml of ether and 200 ml of water, and the organic layer washed successively with 3×200 ml water, 1×200 ml 5% aqueous NaHCO$_3$, 2×200 ml water, and 2×200 ml saturated brine solution. The organic layer was dried (MgSO$_4$), and evaporated. The resulting residue was purified by column chromatography packed with silica gel (1:1 hexanes:ethyl acetate), affording a clear yellow viscous oil (7.2 g, 62%). $^1$H-NMR (CDCl$_3$, ppm): δ 7.26 (d, 1H, J=5 Hz), 6.96 (d, 1H, J=5 Hz), 6.88 (d, 1H, J=3.2 Hz), 4.12 (m, 4H), 3.34 (d, 2H, J=20.5 Hz), 2.47 (m, 4H), 1.52 (m, 4H), 1.31 (t, 6H), 1.24 (m, 12H), 0.86 (t, 6H).

5-(5'-Bromo-3,3'-dihexyl-2,2'-bithienyl)methylphosphonate. A solution of 5-(3,3'-dihexyl-2,2'-bithienyl)methylphosphonate (7 g, 14.5 mmol) and NBS (2.8 g, 15.7 mmol) in 150 ml of dichloromethane was stirred at 0° C. for 1 h and at room temperature for 2 h. Then the mixture was washed with 100 ml of 10% KOH aqueous solution and then with water until the solution was neutral. The organic layer was concentrated to give the crude product (7.8 g, 96%). $^1$H-NMR (CDCl$_3$, ppm): δ6.90 (s, 1H), 6.84 (d, 1H, J=5 Hz), 4.10 (m, 4H), 3.30 (d, 2H, J=20.5 Hz), 2.43 (m, 4H), 1.50 (m, 4H), 1.29 (t, 6H), 1.22 (m, 12H), 0.85 (t, 6H).

5-[E-4-(N,N-Diethylamino)phenylene]-5'-bromo-3,3'-dihexyl-2,2'-bithiophene. To a solution of 5-(5'-bromo-3,3'-dihexyl-2,2'-bithienyl)methylphosphonate (7.5 g, 13.3 mmol) and potassium t-butoxide (1.7 g, 14.6 mmol) in 100 ml of THF was added 4-(diethylamino)benzaldehyde (2.4 g, 13.3 mmol) in 20 ml of THF at 0° C. during 30 min. This is stirred for 4 h and normal workup gave a yellow viscous oil (7.0 g, 90%). $^1$H-NMR (CDCl$_3$, ppm): δ7.32 (d, 2H, J=5 Hz), 6.90 (d, 1H, J=7.5 Hz), 6.85 (s, 1H), 6.80 (s, 1H), 6.78 (d, 1H, J=7.5 Hz), 6.67 (d, 2H, J=5 Hz), 3.41 (q, 4H), 2.50 (t, 2H), 2.41 (t, 2H), 1.50 (m, 4H), 1.21 (m, 12H), 1.17 (t, 6H), 0.87 (t, 6H).

5-[E-4-(N,N-Diethylamino)phenylene]-5'-formyl-3,3'-dihexyl-2,2'-bithiophene. n-Butyllithium (12 ml, 2.5 M in hexanes, 30 mmol) was added dropwise to a solution of 5-[E-4-(N,N-diethylamino)phenylene]-5'-bromo-3,3'-dihexyl-2,2'-bithiophene (7 g, 12 mmol) in 80 ml of THF over 15 min at −78° C. Then the reaction mixture was allowed to gradually rise to −20° C. and 5 ml of anhydrous DMF was added. After the mixture was stirred for 3 h, 50 ml of 1N HCl was added dropwise to terminate the reaction. The normal workup was then carried out and the crude product was purified by column chromatography over silica gel, eluting with ethyl actate/hexane (1:5) to afford a yellow viscous oil (5.7 g, 89%). $^1$H-NMR (CDCl$_3$, ppm): δ 9.85 (s, 1H), 7.64 (s, 1H), 7.31 (d, 2H, J=5 Hz), 6.96 (d, 1H, J=7.5 Hz), 6.90 (s, 1H), 6.79 (d, 1H, J=7.5 Hz), 6.50 (d, 2H, J=5 Hz), 3.36 (q, 4H), 2.61 (t, 2H), 2.50 (t, 2H), 1.55 (m, 4H), 1.26 (m, 12H), 1.17 (t, 6H), 0.85 (t, 6H).

The chromophore was then prepared by reaction with the furan. The furan can be prepared by the synthetic scheme illustrated in FIG. 16.

Example 4

Figure 17:
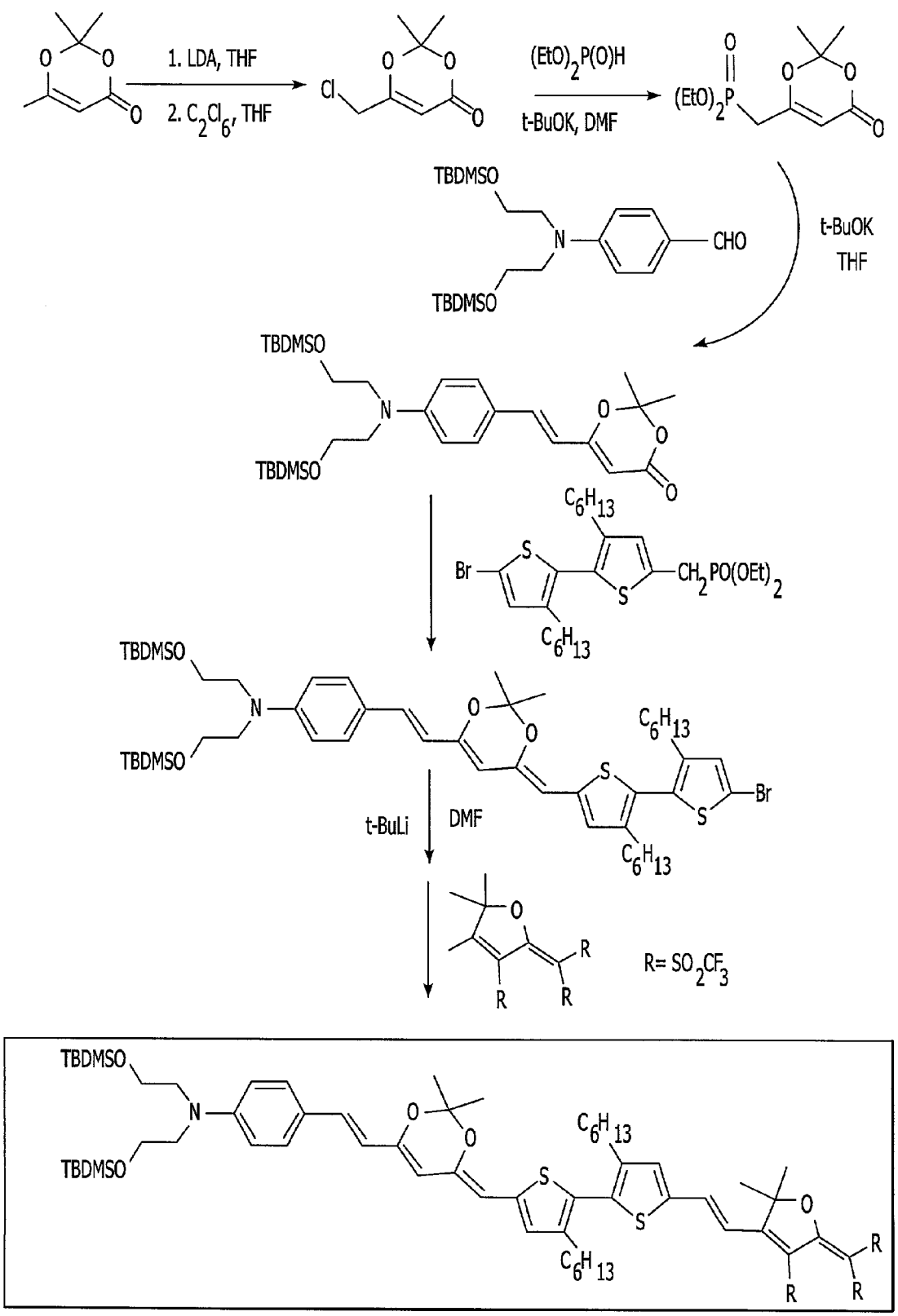
FIG. 17 is a synthetic scheme for the preparation of representative dithiophene-bridged chromophores of the invention.

The Preparation and Properties of a Representative Chromophore: Amine Donor, Dithiophene/Dioxene-Containing Bridge, Furan Acceptor In this example, the preparation and properties of a representative chromophore of the invention are described. The chromophore includes a phenyl amine donor, a bridge that includes a substituted dithiophene and dioxene, and a furan acceptor. The overall synthetic scheme is illustrated in FIG. 17. Referring to FIG. 17, n-hexyl substituents are incorporated into the dithiophene to provide an intermediate that is then modified for condensation with the donor-dioxene bridge component. The resulting donor-dithiophene/dioxene bridge component is reacted with an appropriate furan to provide the chromophore. In FIG. 17, R is indicated to be —SO$_2$CF$_3$. Suitable R groups also include F, CN, and CF$_3$. Other acceptors can also be coupled to the donor-bridge component. The synthetic procedures follow.

6-Chloromethyl-2,2-dimethyl-1,3-dioxen-4-one. A solution of 2,2,6-trimethyl-1,3-dioxen-4-one (16.0 g, 0.11 mol) in THF (50 ml) was added dropwise over 20 min to a solution of lithium diisopropylamide (75 ml, 2.0 M solution in heptane/THF/ethylbenzene, 0.15 mol) at the temperature of −78° C. During the addition, a fine yellow suspension formed. Subsequently, the enolate solution was stirred at −78° C. for another 1 h and then cannulated to a solution of hexachloroethane (39 g, 0.16 mol) in THF (200 ml) at −50° C. over 30 min. The resulting reaction mixture was then allowed to warm slowly to −25° C., and poured into ice-cold aqueous 10% hydrochloric acid (200 ml). The organic layer extracted with ether was washed with brine, dried over sodium sulfate and concentrated under reduced pressure to afford 15.9 g of yellow oil. The product was used without further purification. $^1$H NMR (CDCl$_3$, ppm): δ5.57 (s, 1H), 4.00 (s, 2H), 1.96 (s, 6H).

6-Diethylphosphonomethyl-2,2-dimethyl-1,3-dioxen-4-one. A mixture of 6-chloromethyl-2,2-dimethyl-1,3-dioxen-4-one (11 g, 0.062 mol) and potassium t-butoxide (21 g, 0.187 mol) in dimethylformamide (200 ml) was stirred in the ice-bath. During the process, the resulting solution turned to purple after approximately 1 hour. After another 3 hours, the reaction mixture was treated cautiously with concentrated hydrochloric acid until the purple color disappeared. The resulting mixture was filtered, and the collected solids were washed with THF. The combined organic portions were purified by column chromatography to afford 12.6 g (73%) of 6-diethylphosphonomethyl-2,2-dimethyl-1,3-dioxen-4-one. $^1$H NMR (CDCl$_3$, ppm): δ 5.40 (d, 1H), 4.20 (m, 4H), 2.87 (d, 2H), 1.72(s, 6H), 1.43 (t, 6H).

6-[E-(N,N-di(t-butyldimethylsilyloxyethyl-amino)phenylene]-2,2-dimethyl-1,3-dioxen-4-one. Prepared by the same method as described above for 5-[E-4-(N,N-diethylamino)phenylene]-5'-bromo-3,3'-dihexyl-2,2'-bithiophene. The product was obtained with a yield of 83% as yellow oil. $^1$H NMR (CDCl$_3$, ppm): δ7.35 (d, 2H), 6.90 (d, 1H), 6.73 (d, 1H), 6.65 (d, 2H), 6.00 (s, 1H), 3.79 (t, 4H), 3.56 (t, 4H), 1.75(s, 6H), 0.91 (s, 18H), 0.03 (s, 12H).

5-{6-[E-(N,N-di(t-butyldimethylsilyloxyethyl-amino)phenylene]-2,2-dimethyl-1,3-dioxen-4-vinyl}-5'-bromo-3,3'-dihexyl-2,2'-biothiophene. Yield: 15%. $^1$H NMR (CDCl$_3$, ppm): δ 7.35 (d, 2H), 6.92 (d, 1H), 6.87 (s, 1H), 6.81 (s, 1H), 6.77 (d, 1H), 6.63 (d, 2H), 6.27 (s, 1H), 6.03 (s, 1H), 3.79 (t, 4H), 3.53 (t, 4H), 2.51 (t, 2H), 2.47 (t, 2H), 1.74 (s, 6H), 1.56 (m, 4H), 1.24 (m, 12H), 0.94 (s, 18H), 0.87 (t, 6H), 0.03 (s, 12H).

5-{6-[E-(N,N-di(t-butyldimethylsilyloxyethyl-amino)phenylene]-2,2-dimethyl-1,3-dioxen-4-vinyl}-5'-formyl-3,3'-dihexyl-2,2'-biothiophene. Prepared by the same method as described above for 5-[E-4-(N,N-diethylamino)phenylene]-5'-formyl-3,3'-dihexyl-2,2'-bithiophene afforded a dark-red viscous oil (81%). $^1$H NMR (CDCl$_3$, ppm): δ 9.91 (s, 1H), 7.67 (s, 1H), 7.33 (d, 2H), 6.96 (d, 1H), 6.93 (s, 1H), 6.84 (d, 1H), 6.69 (d, 2H), 6.15 (s, 1H), 6.04 (s, 1H), 3.84 (t, 4H), 3.50 (t, 4H), 2.61 (t, 2H), 2.50 (t, 2H), 1.76(s, 6H), 1.58 (m, 4H), 1.24 (m, 12H), 0.91 (s, 18h), 0.87 (t, 6H), 0.01 (s, 12H).

The chromophore was then prepared by reaction with the furan. The furan can be prepared by the synthetic scheme illustrated in FIG. 16.

Figure 18:
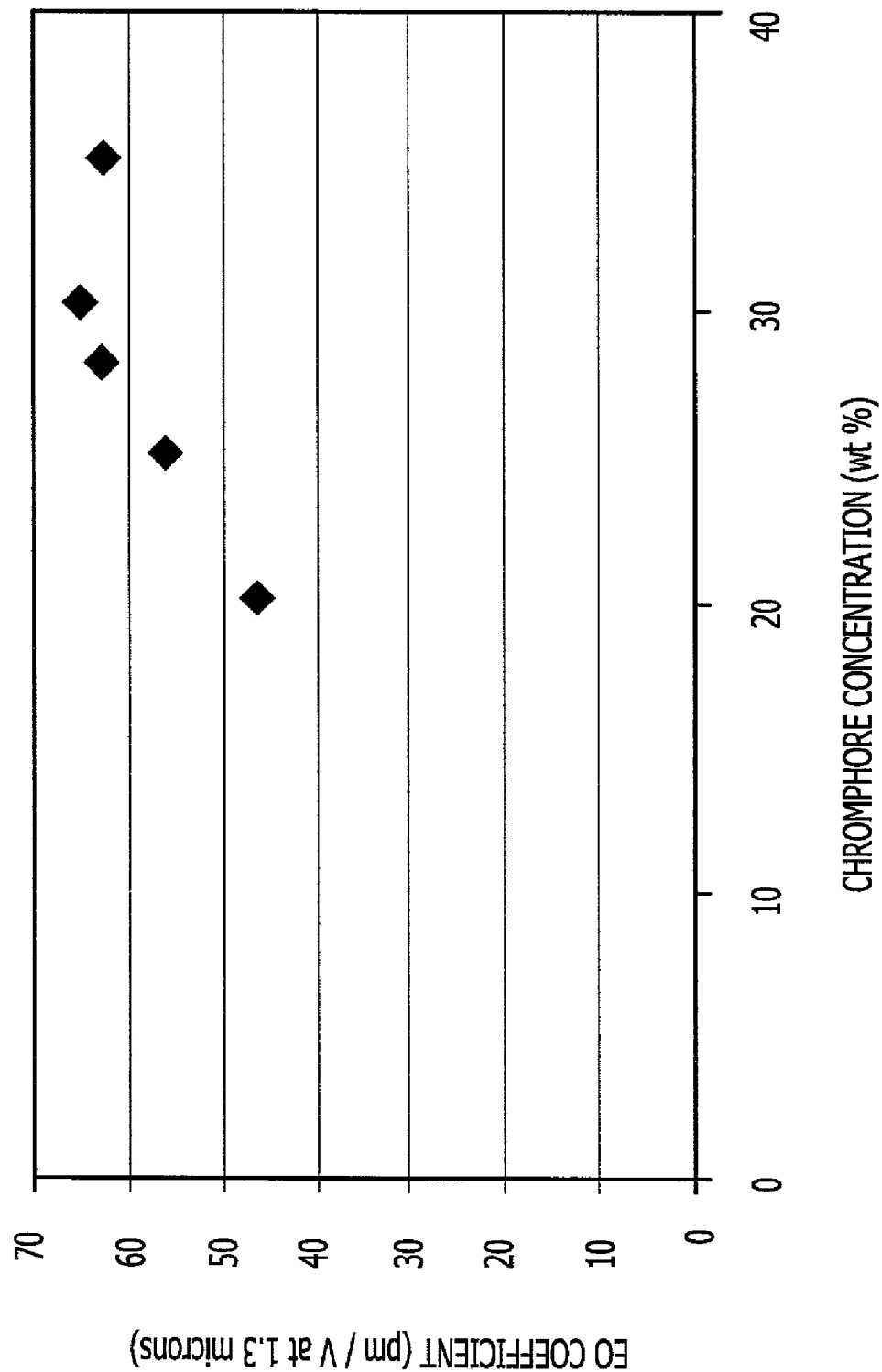
FIG. 18 is a graph illustrating electro-optic coefficient (pm/V at 1.3 microns) as a function of chromophore loading (weight percent) for a representative chromophore of the invention in amorphous polycarbonate.

The electro-optic coefficient (picometers/volt, pm/V, at 1.3 microns), $r_{33}$, as a function of chromophore loading (weight percent) was determined as described above for a corresponding chromophore having a tricyanofuran acceptor in amorphous polycarbonate. The results are illustrated in FIG. 18. Referring to FIG. 18, the greatest electro-optic coefficient (66 pm/V) was measured at 30 weight percent chromophore and electro-optic coefficients of 64 pm/V were achieved for loadings of 28 and 35 weight percent chromophore. Electro-optic coefficients of 47 and 57 pm/V were achieved at 20 and 30 weight percent chromophore, respectively.

Example 5

The Preparation of Representative Trifluoromethylsulfonyl Substituted Acceptors In this example, the preparation of a representative trifluoromethylsulfonyl ($-SO_2CF_3$) substituted acceptors and examples of chromophores that include such accpetors is described. Representative trifluoromethylsulfonyl substituted furans can be prepared from various precursors by reaction with the anion of bis(trifluoromethylsulfonyl)methane. Synthetic schemes for the preparation of three representative acceptors are illustrated in FIGS. 16, 19, and 20.

Referring to FIG. 16, reaction of ethyl bromoacetate with 3-methyl-3-hydroxybutanone provides the cyano substituted cyclopentenoate which, on reaction with the anion of bis(trifluoromethylsulfonyl)methane, provides the illustrated representative trifluoromethylsulfonyl substituted furan.

Referring to FIG. 19, reaction of the anion of bis(trifluoromethylsulfonyl)methane with the cyclopentenoate, prepared by condensation of 3-methyl-3-hydroxybutanone and ethyl cyanoacetate, provides the illustrated representative trifluoromethylsulfonyl substituted furan.

Referring to FIG. 20, reaction of the anion of bis(trifluoromethylsulfonyl)methane with the methyl-1,4-benzoquinone provides the illustrated representative trifluoromethylsulfonyl substituted cyclohexadiene.

The $^1$H NMR spectrum of bis(trifluoromethylsulfonyl)methane exhibits a singlet at δ5.02 in chloroform with TMS reference.

Figure 21:
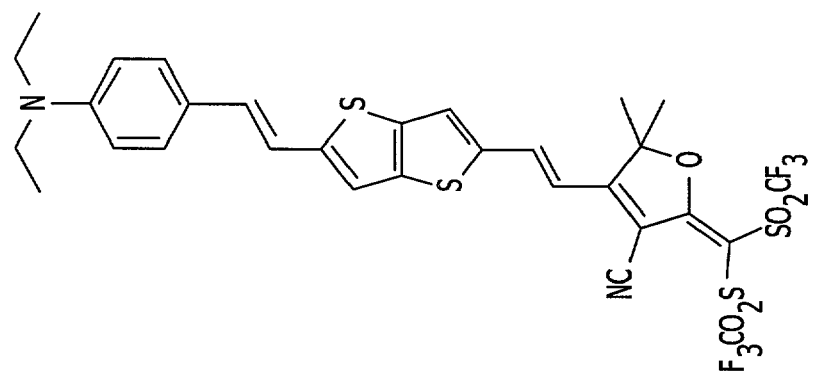
FIG. 21 is an illustration of representative fused dithiophene-bridged chromophores of the invention including trifluoromethylsulfonyl substituted acceptors.
Figure 21:
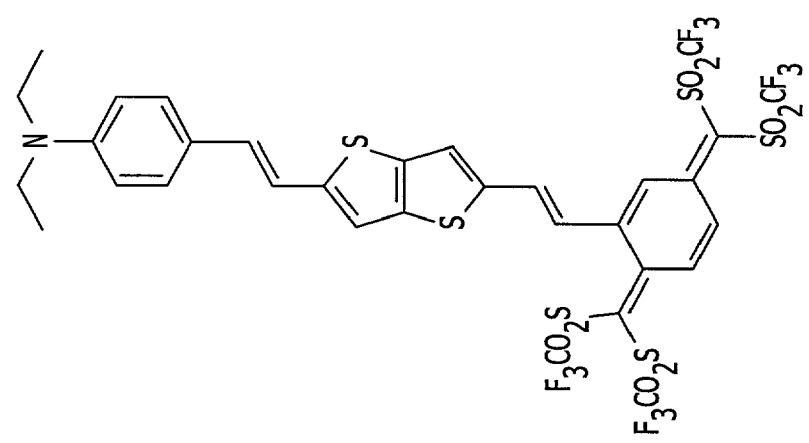
Figure 21:
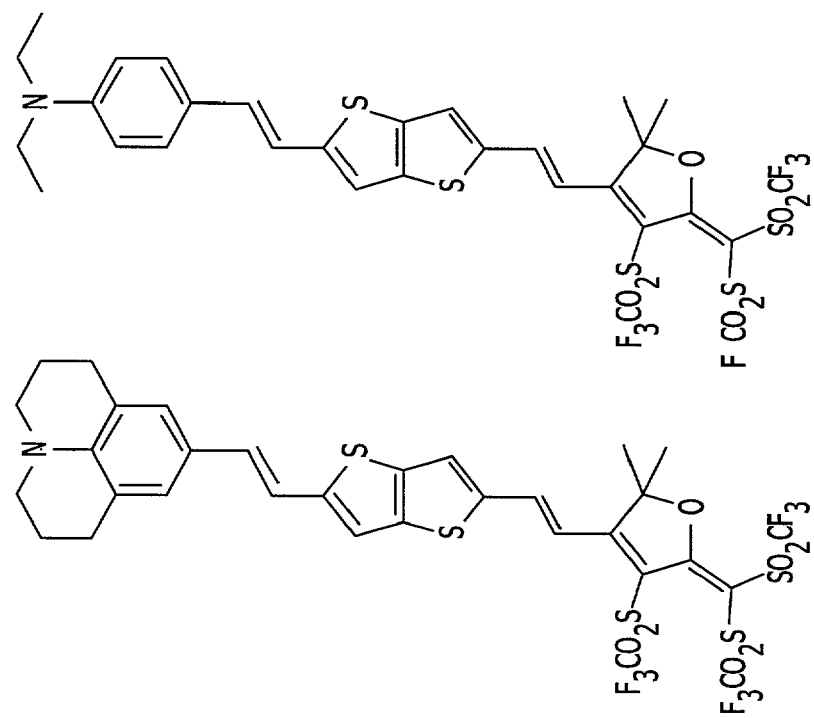

Representative chromophores of the invention that include phenyl amine donors, fused dithiophene—containing bridges, and trifluoromethylsulfonyl substituted acceptors are illustrated in FIG. 21. In general, the chromophores including trifluoromethylsulfonyl substituted acceptors show improved electro-optic activity compared to their trifluoromethyl- and cyano-substituted counterparts. Improvements of a factor of about 1.3 in dipole moment and about 1.5 in molecular hyperpolarizability have been observed.

Example 6

The Preparation and Properties of a Representative Dendrimer Functionalized Chromophore: Amine Donor, Cyanofuran Acceptor, Thiophene-Containing Bridge In this example, the preparation and properties of a representative dendrimer functionalized chromophore of the invention are described. The chromophore includes a phenyl amine donor, a substituted dithiophene-containing bridge (3-methylol substituted thiophene), and a furan acceptor (2-dicyanomethylen-3-cyano-5,5-di-n-butyl-2,4-dihydrofuran). The chromophore includes three phenyl benzyl ether dendrons. The dendrons provide site isolation to the chromophore.

Figure 22:
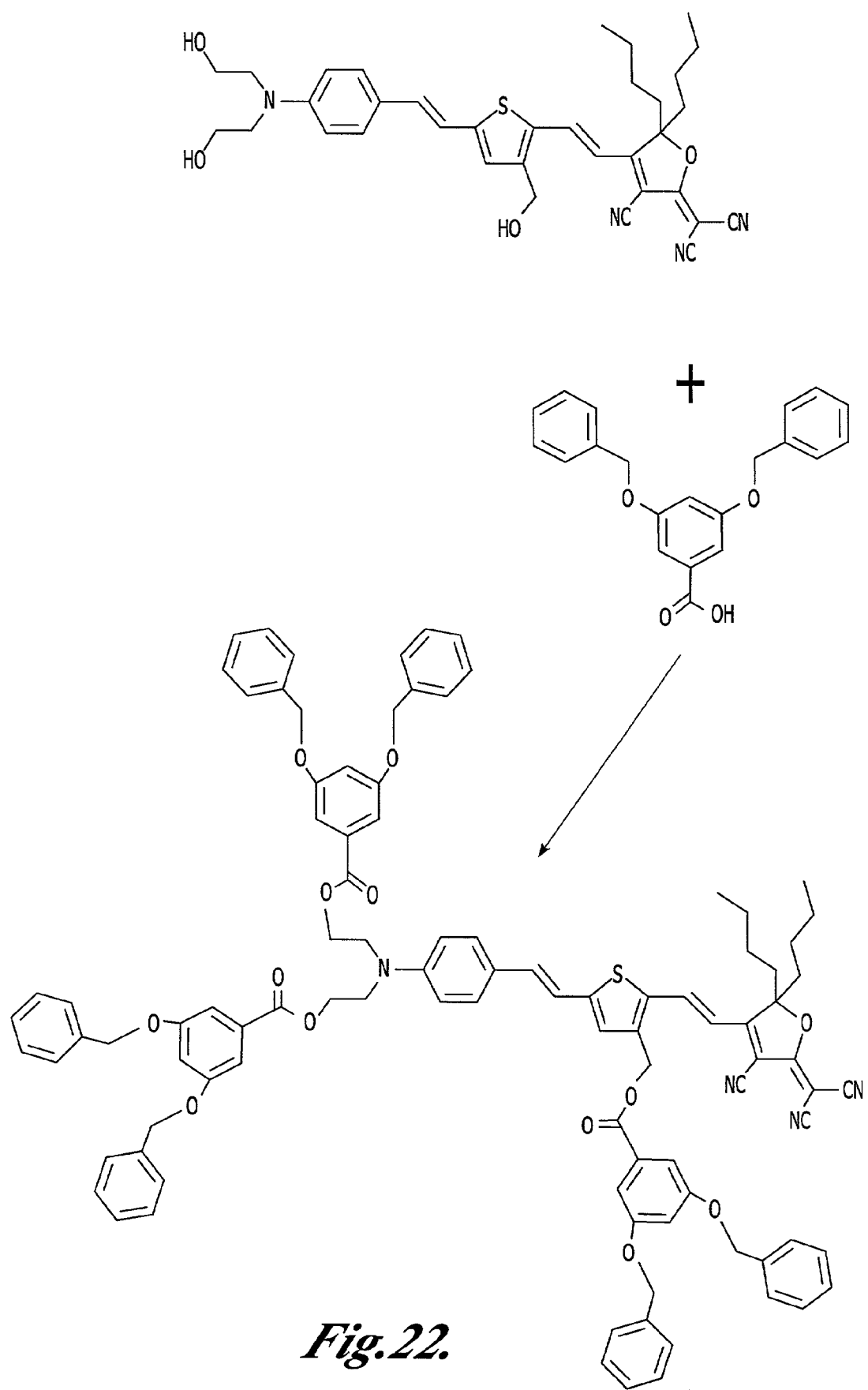
FIG. 22 is a synthetic scheme for the preparation of representative dendrimer functionalized thiophene-bridged chromophore of the invention.

The first generation dendrimer was synthesized as illustrated in FIG. 22. Referring to FIG. 22, the trialcohol (see Dalton et al., Polymer Preprints, 1999, 40, 1, 156) was treated with a phenyl benzyl ether derivative (e.g., carboxylic acid or acid chloride, see Frechet et al., J. Amer. Chem. Soc., 1990, 112, 7638) to provide the dendrimer. The synthetic procedure follows.

To chromophore trialcohol (139 mg, 0.226 mmole) in a 25 mL round bottom flask equipped with a Teflon coated stir bar and a nitrogen purge was added and the mixture stirred for five minutes at room temperature. Dimethylaminopyridine (8.5 mg, 0.07 mmole), diisopropylethylamine (0.24 mL, 1.4 mmole), and the phenyl benzyl ether acid chloride (0.480 mg, 1.36 mmole) were added to the trialcohol solution. The reaction was followed by TLC with 95% dichloromethane/ 5% ethyl acetate as the eluent. After five hours, the reaction had gone to completion, and the THF was removed under reduced pressure. The residue was purified by silica gel column chromatography (0.06–0.2 mm, 70–230 mesh from Lancaster) eluting with 95% dichloromethane/5% ethyl acetate.

The $^1$H NMR spectrum (Bruker 300 MHz, 10% w/w $CDCl_3$) of the purified product show two distinct benzylic peaks centered at 5.05 and 5.10 ppm in a 2:1 ratio. The benzylic protons of the dendrons attached to the donor end of the chromophore are equivalent giving rise to one peak at 5.05 ppm. The benzylic protons from the dendron attached to the thiophene come at 5.10 ppm. The intensity of these peaks to the triplet centered at 0.9 ppm are in the ratio 4:8:6.

The mass spectrum showed only a parent ion at 1620.08 amu.

Figure 23:
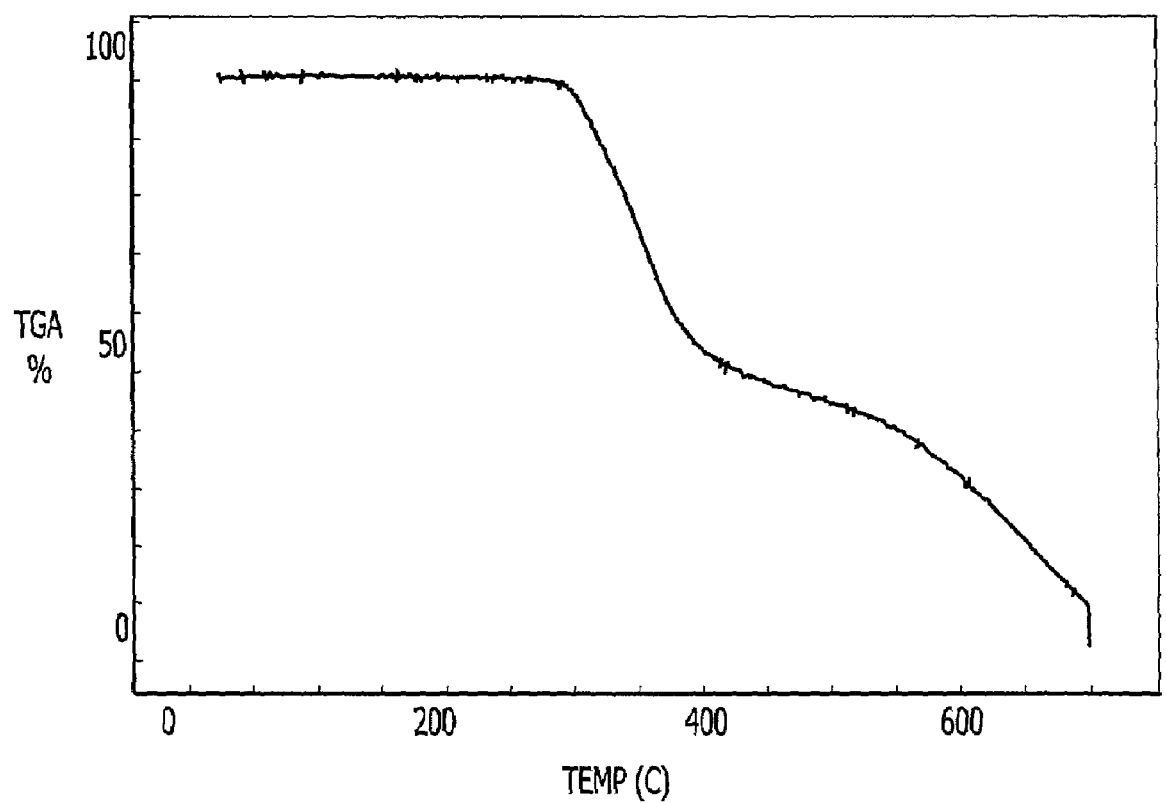
FIG. 23 is the thermogravimetric analysis of the dendrimer functionalized chromophore shown in FIG. 22.

Thermogravimetric analysis, TGA, (Shimadzu TGA-50, 10°/minute from room temperature to 750° C.) of the dendrimer showed that degradation begins at 285° C. By 400° C. approximately 50% of the weight is lost. Between 400° C. and 500° C. approximately 10% if the weight is lost. By 700° C., 10% of the original mass remains. FIG. 23 presents the thermogravimetric analysis.

Figure 24:
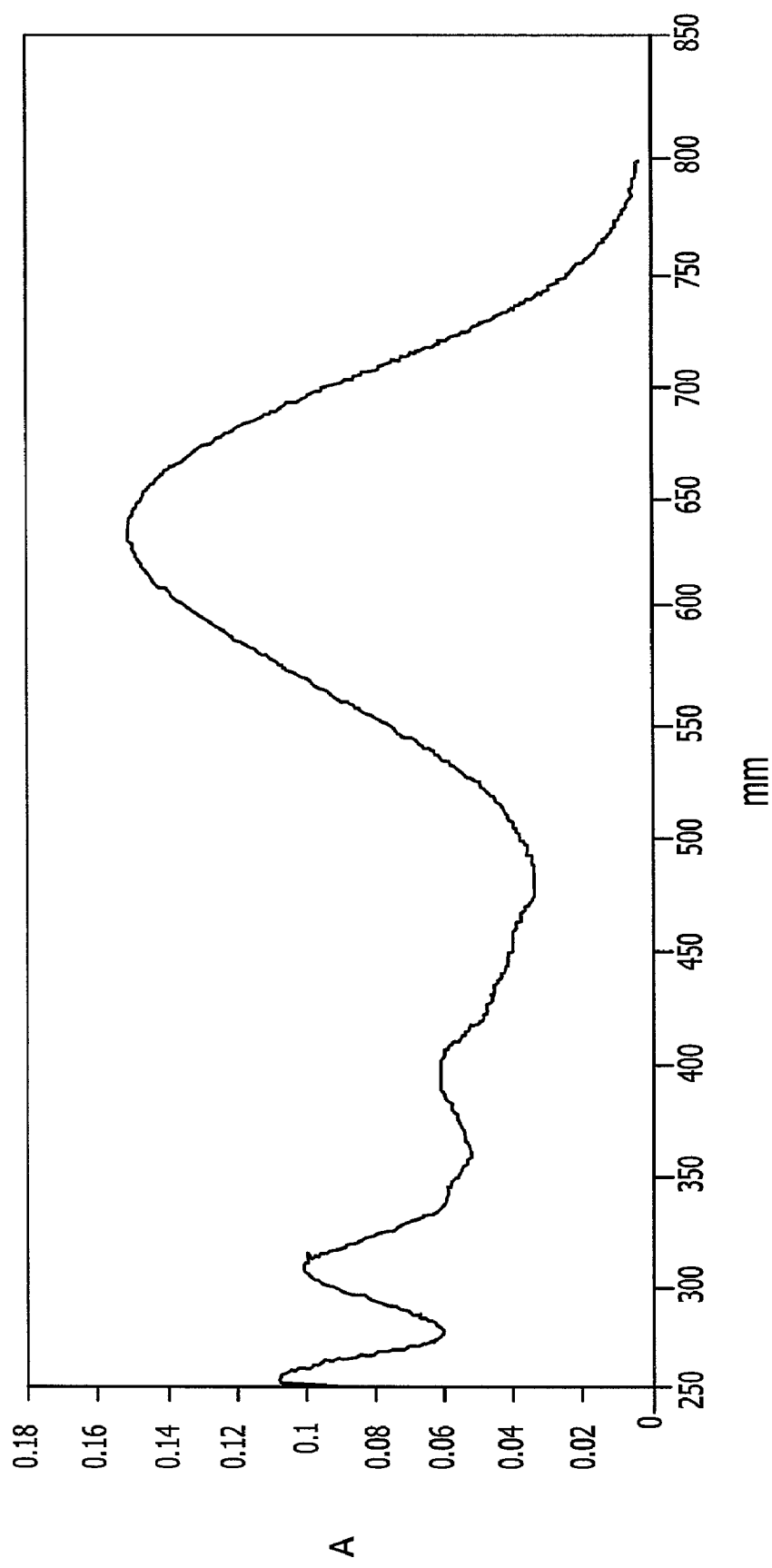
FIG. 24 is the UV-VIS absorption spectrum of the dendrimer functionalized chromophore shown in FIG. 22.

The UV-VIS absorption spectrum (Shimadzu UV-1601) in chloroform shows a charge transfer band at 635 nm. FIG. 24 presents the absorption spectrum.

Figure 25:
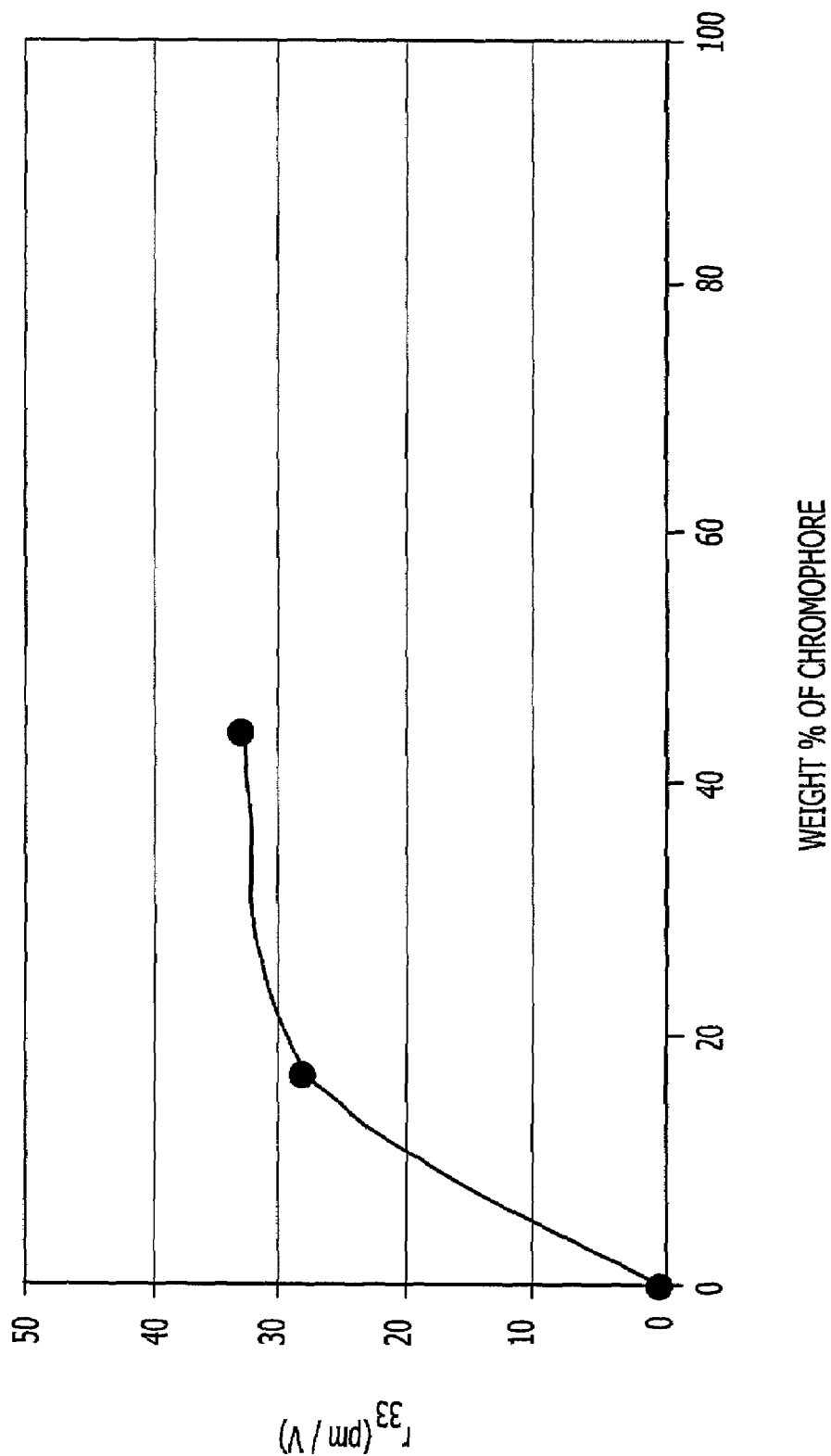
FIG. 25 is a graph illustrating electro-optic coefficient (pm/V at 1.3 microns) as a function of chromophore loading (weight percent) for the dendrimer functionalized chromophore shown in FIG. 22.

The electro-optic coefficient (picometers/volt, pm/V, at 1.3 microns), $r_{33}$, as a function of chromophore loading (weight percent) was determined as described above for this chromophore in amorphous polycarbonate. The results are illustrated in FIG. 25. Referring to FIG. 25, the greatest electro-optic coefficient (about 33 pm/V) was measured at about 44 weight percent chrompohore. The electro-optic coefficient was about 28 pm/V for a loading of about 17 weight percent chromophore.

Example 7

Figure 26:
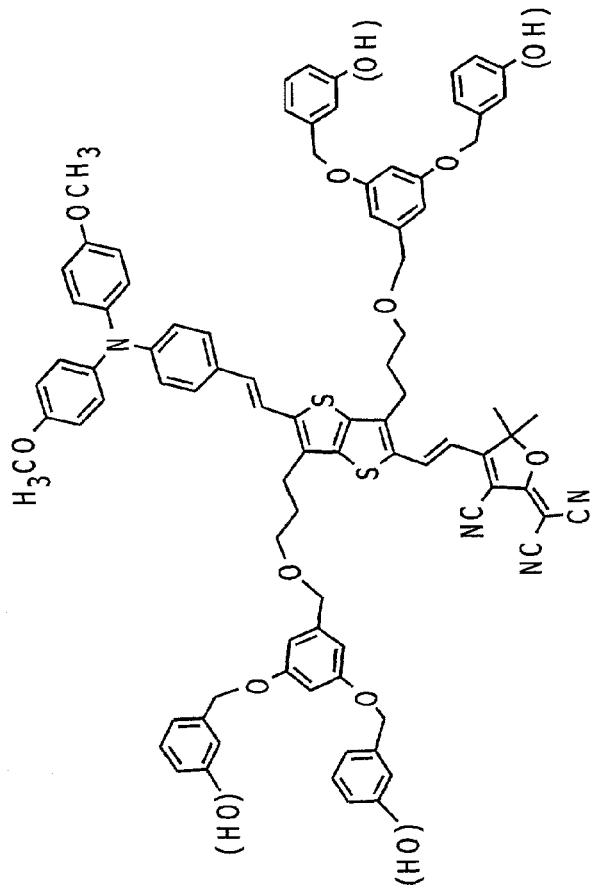
FIG. 26 is an illustration of a representative dendrimer functionalized fused dithiophene-bridged chromophore of the invention.

The Preparation of a Representative Dendrimer Functionalized Chromophore: Amine Donors Cyanofuran Acceptor, Fused Dithiophene-Containing Bridge In this example, the preparation of a representative dendrimer functionalized chromophore of the invention is described. The chromophore includes a triphenyl amine donor, a substituted fused dithiophene-containing bridge, and a furan acceptor (2-dicyanomethylen-3-cyano-5,5-dimethyl-2,4-dihydrofuran). The chromophore includes two phenyl benzyl ether dendrons. As shown in FIG. 26, the dendrons can be substituted (e.g., —OH) for further functionalization.

Figure 27:
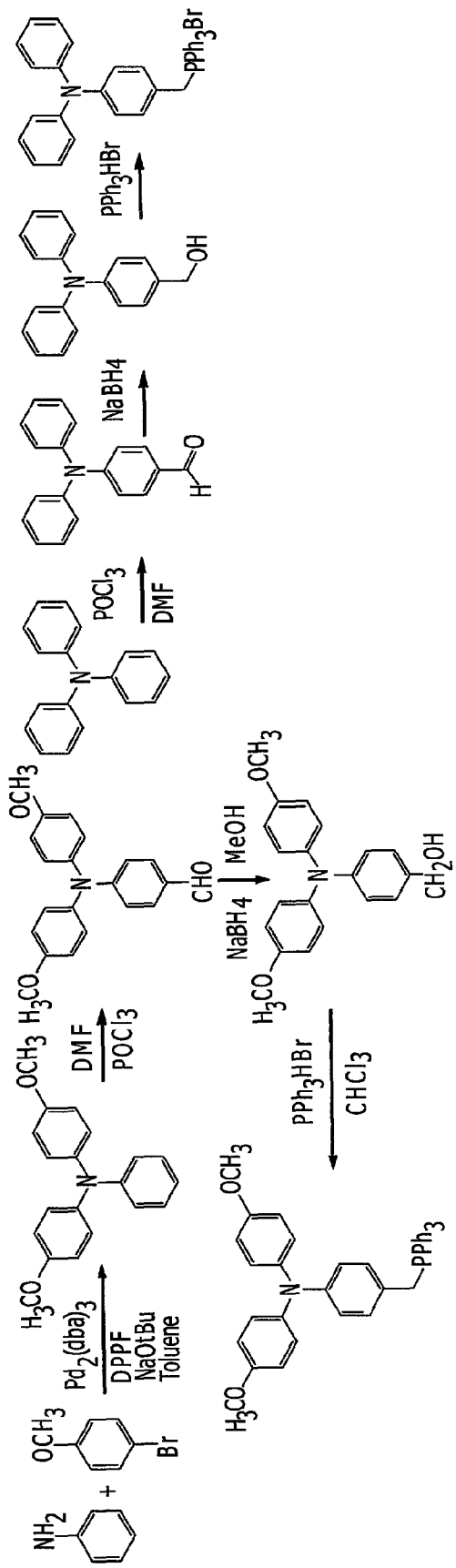
FIG. 27 is a synthetic scheme for the preparation of a triphenyl amine donors useful in the preparation of the chromophores of the invention.

The representative dendrimer functionalized chromophore is illustrated in FIG. 26. The synthetic scheme for the preparation of the donor is illustrated in FIG. 27 and described below.

Preparation of Triphenylamine Wittig Salts for Reaction with Bridge Component Bis(4-methoxyphenyl)phenylamine (1). In a procedure modified from Thayumanavan et al. (Chem Mater., 1997, 9, 3231–3235), to a solution of 4.975 g (5.43 mmol) of tris(dibenzylideneacetone)-dipalladium (0) and 4.519 g (8.15 mmol) of 1,1'-bis(diphenylphosphino)-ferrocene in 680 mL toluene under nitrogen was added 68.46 mL (0.245 mol) of 4-bromoanisole and was allowed to stir for 25 minutes. Then, sodium t-butoxide (59.36 g, 0.618 mol) and aniline (22.5 mL, 0.236 mol) were added to the solution and stirred at 90° C. for approximately 2 weeks. The complete formation of dicoupled product was monitored by thin layer chromatography. The reaction solution was then worked up with several (3×) brine washings, extracted with ether, and dried over $MgSO_4$. A flash column of 5% ethyl acetate/95% hexanes gave a light brown solid. The still crude product was purified on a column with 1% ethyl acetate/99% hexanes mobile phase to afford 20.39 g of white solid. $^1$H NMR ($CDCl_3$): $\delta$3.98 (s, 6H), $\delta$7.01–7.23 (m, 1H), $\delta$7.36 (d, 2H); m/z 305.1 ($M^+$), 290.1 ($M^+$–$CH_3$).

4-[Bis(4-methoxyphenyl)amino]benaldehyde (2). In an addition funnel, 0.34 mL (3.64 mmol) of $POCl_3$ was added dropwise a stirred cooled solution (0° C.) containing 0.76 mL (9.84 mmol) of DMF in a three-neck flask and allowed to stir for 1 hr. The mixture was then allowed to warm to room temperature. A solution of 1 (1.0 g, 3.28 mmol) in 1,2-dichloroethane was then added dropwise. After complete addition, the additional funnel was replaced with a condenser and the solution was heated to 90–95° C. for ~3 hrs. After slight cooling, the solution was added dropwise to a solution of $NaHCO_3$. The crude product was extracted with $CH_2Cl_2$, washed 3× with $NaHCO_3$, and dried over $Na_2SO_4$. The crude product was purified with column chromatography with 20% ethyl acetate/80% hexanes as the mobile phase to reveal 1.19 g of a viscous bright yellow oil. $^1$H NMR ($CDCl_3$): $\delta$3.98 (s, 6H), $\delta$6.92 (d, 4H), $\delta$7.16 (d, 4H), $\delta$7.64 (d, 2H), $\delta$9.75 (s, 1H); m/z 356.1 ($M^+$+Na), 334.1 ($M^+$+H).

{4-[bis(4-methoxyphenyl)amino]phenyl}methan-1-ol (3). To a solution of methanol, 0.68 g (2.04 mmol) of 2 was added and stirred. To a prepared solution of 0.6 g of NaOH in 1.2 mL $H_2O$ was added $NaBH_4$ (0.0386 g, 1.02 mmol) and 10 mL of methanol. The prepared solution was added to the stirred solution of 2 at 0° C. via an addition funnel. The solution was allowed to stir at room temperature overnight. The solution was then worked up with brine washings (3×), extracted with ether, and dried over $MgSO_4$. Removal of solvent revealed 0.67 g of a viscous pale oil. The product is suitable for further reaction without purification. $^1$H NMR ($CDCl_3$): $\delta$4.02 (s, 6H), $\delta$4.81 (d, 2H), $\delta$7.02 (d, 4H), $\delta$7.14 (d, 4H), $\delta$7.26 (d, 2H), $\delta$7.39 (d, 2H); m/z 358.1 ($M^+$+Na), 336.1 ($M^+$+H), 318.1 ($M^+$–$CH_3$).

{4-[Bis-(4-methoxyphenyl)amino]phenyl}(triphenylphosphonium bromide (4). A solution of 3 (1.226 g, 3.65 mmol) and triphenylphosphonium hydrobromide (1.129 g, 3.29 mmol) in ~100 mL of chloroform was placed on an azeotrope distillation apparatus and refluxed to remove water for 2–3 hours. Once cooled to room temperature, the chloroform solution was concentrated via rotary evaporation. The product was precipitated using ether and 2.40 g was isolated by filtration. $^1$H NMR ($CDCl_3$): $\delta$3.78 (s, 6H), $\delta$5.28 (d, 2H), $\delta$6.64 (d, 4H), $\delta$6.78 (d, 4H), $\delta$6.97 (d, 2H), $\delta$7.58–7.82 (m, 15H); m/z 580.2 ($M^+$–Br), 318.2 ($M^+$–$Ph_3Br$).

4-(Diphenylamino)benzaldehyde (2B). $POCl_3$ (4.23 mL, 45.3 mmol) was added dropwise to a stirred solution of fresh DMF (9.45 mL, 122 mmol) on an ice bath (0° C.). Allowed mixture to stir at room temperature for 1 hr. 1A (10 g, 40.8 mmol) in dichloroethane was added dropwise to the mixture. The addition funnel was then replaced with a condenser and the solution was heated to 90–95° C. for 3 hours. The solution was removed from heat, cooled, and poured into a stirring solution of $NaHCO_3$. The crude product was extracted with methylene chloride and washed with $NaHCO_3$. The combined organic extracts were dried over $MgSO_4$. Product was recrystallized in hexanes to reveal 5.90 g (53%) of cream orange solid. $^1$H NMR ($CDCl_3$): $\delta$7.03 (d, 4H), $\delta$7.15–7.20 (m, 4H), $\delta$7.36 (t, 4H), $\delta$7.69 (d, 2H), $\delta$9.82 (s, 1H); m/z 296.1 ($M^+$+Na), 274.1 ($M^+$+H).

[4-(Diphenylamino)phenyl]methan-1-ol (3B). To a solution of 2B (3.637 g, 13.3 mmol) in methanol was added dropwise at 0° C. a solution of $NaBH_4$ added to 3.9 g NaOH dissolved in 7.8 mL $H_2O$. The solution was allowed to stir at room temperature overnight. Water was added and the product was extracted with ether (2×) and washed with brine (2×). The combined ether extracts were dried over $MgSO_4$. The solvent was removed and the product was purified using flash chromatography with a hexanes and then ethyl acetate. The ethyl acetate fraction was collected and the solvent removed to reveal 2.667 g (74%) of a honey yellow crystal solid. $^1$H NMR ($CDCl_3$): $\delta$4.63 (d, 2H), $\delta$6.97–7.06 (m, 6H), $\delta$7.09 (m, 2H), $\delta$7.20–7.28 (m, 6H); m/z 298.1 ($M^+$+Na), 276.1 ($M^+$+H), 258.1 ($M^+$–$H_2O$).

[4-(Diphenylamino)phenyl]triphenylphosphonium bromide (4B). A solution of 3B (3.660 g, 9.66 mmol) and triphenylphosphonium hydrobromide (2.984 g, 8.69 mmol) in ~150 mL of chloroform was placed on an azeotrope distillation apparatus and refluxed to remove water for 3 hours. Once cooled to room temperature, the chloroform solution was concentrated via rotary evaporation. The pure product was precipitated using ether and 5.16 g (89% yield) was isolated by filtration. $^1$H NMR ($CDCl_3$): $\delta$5.40 (d, 2H), $\delta$6.84 (m, 6H), $\delta$7.66–7.70 (m, 8H), $\delta$7.70–7.85 (m, 15H); m/z 520.2 ($M^+$–Br), 258.1 ($M^+$–$PPh_3Br$).

The fused dithiophene bridge component can be prepared and coupled to the donor component by the methods described herein. The dendrimer can be prepared by coupling the dendrons to the functionalized bridge portion of the chromophore by the methods described herein.

Example 8

Figure 28:
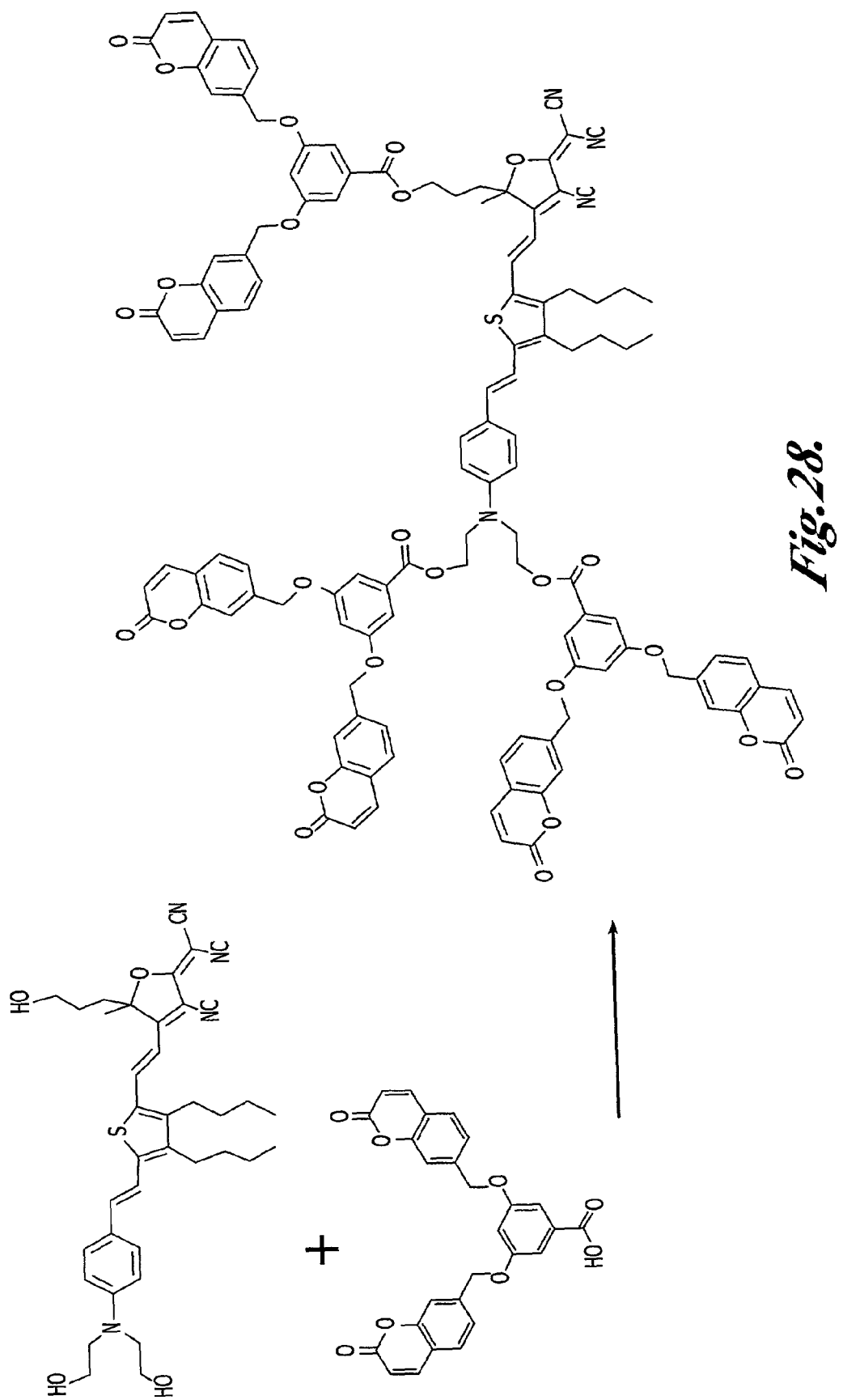
FIG. 28 is a synthetic scheme for the preparation of a representative dendrimer functionalized thiophene-bridged chromophore of the invention.

The Preparation a Representative Dendrimer Functionalized Chromophore: Amine Donor, Cyanofuran Acceptor, Thiophene-Containing Bridge In this example, a representative dendrimer functionalized chromophore of the invention are described. The chromophore includes a phenyl amine donor, a substituted thiophene-containing bridge (3,4-di-n-butyl substituted thiophene), and a furan acceptor (2-dicyanomethylen-3-cyano-5-methyl-5-(propan-3-ol)-2,4-dihydrofuran). The chromophore includes three phenyl benzyl ether dendrons that provide functional groups that are photocrosslinkable. The photocrosslinkable dendrimer functionalized chromophore is illustrated in FIG. 28 and can be prepared by the methods described herein.

Example 9

Figure 33:
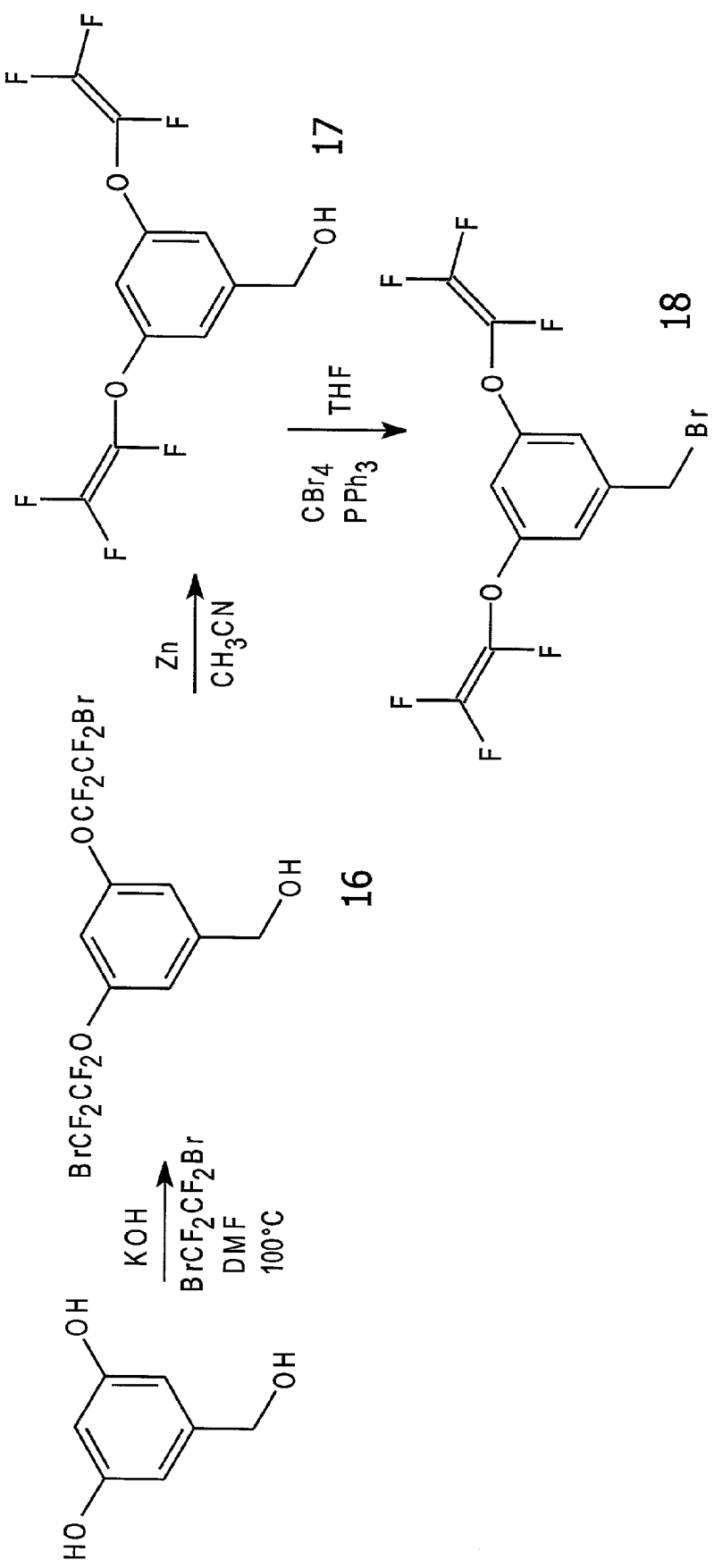
FIG. 33 is a synthetic scheme for the preparation of a dendron useful in the preparation of dendrimer functionalized chromophores of the invention.
Figure 34:
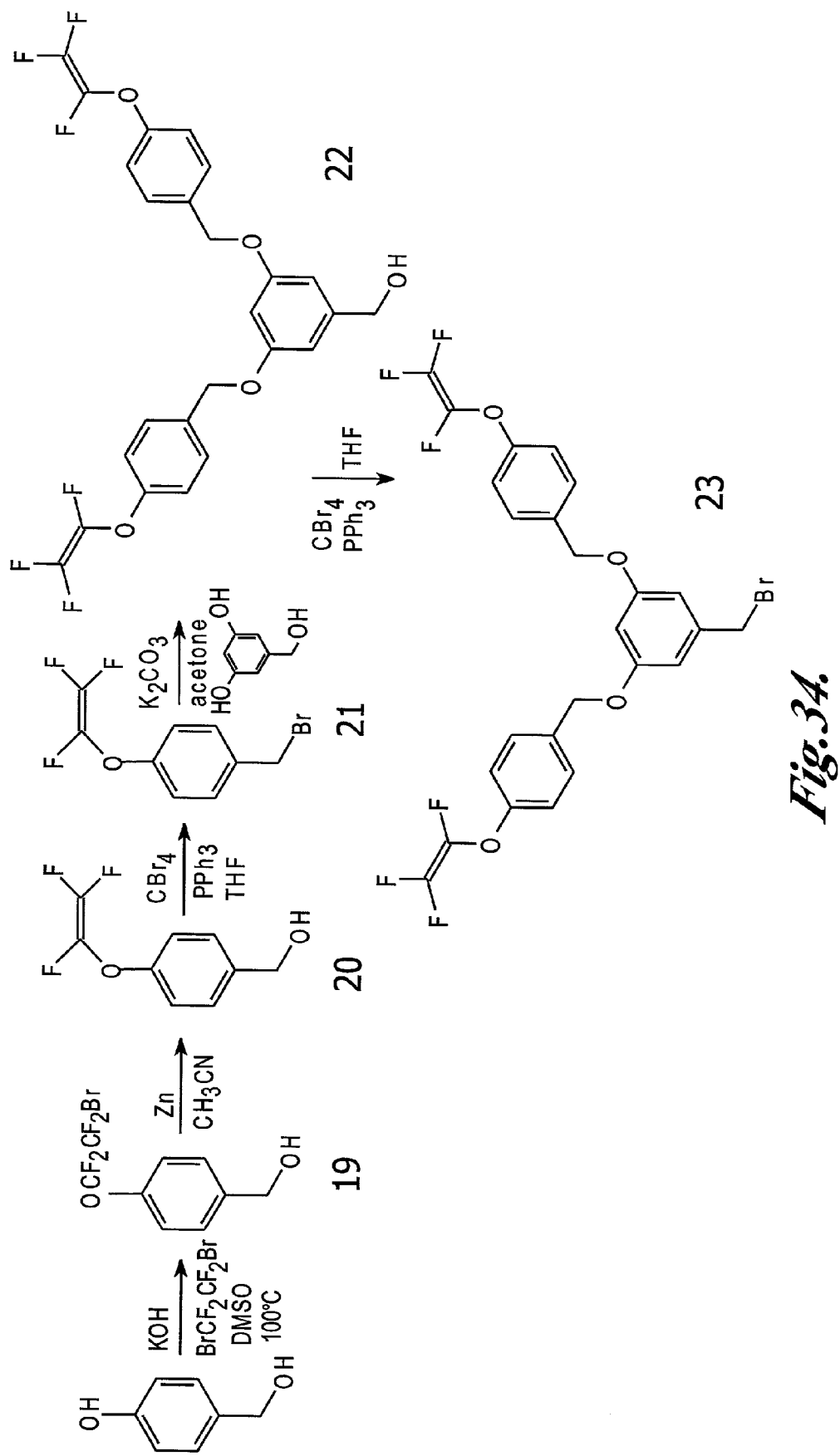
FIG. 34 is a synthetic scheme for the preparation of a dendron useful in the preparation of dendrimer functionalized chromophores of the invention.
Figure 35:
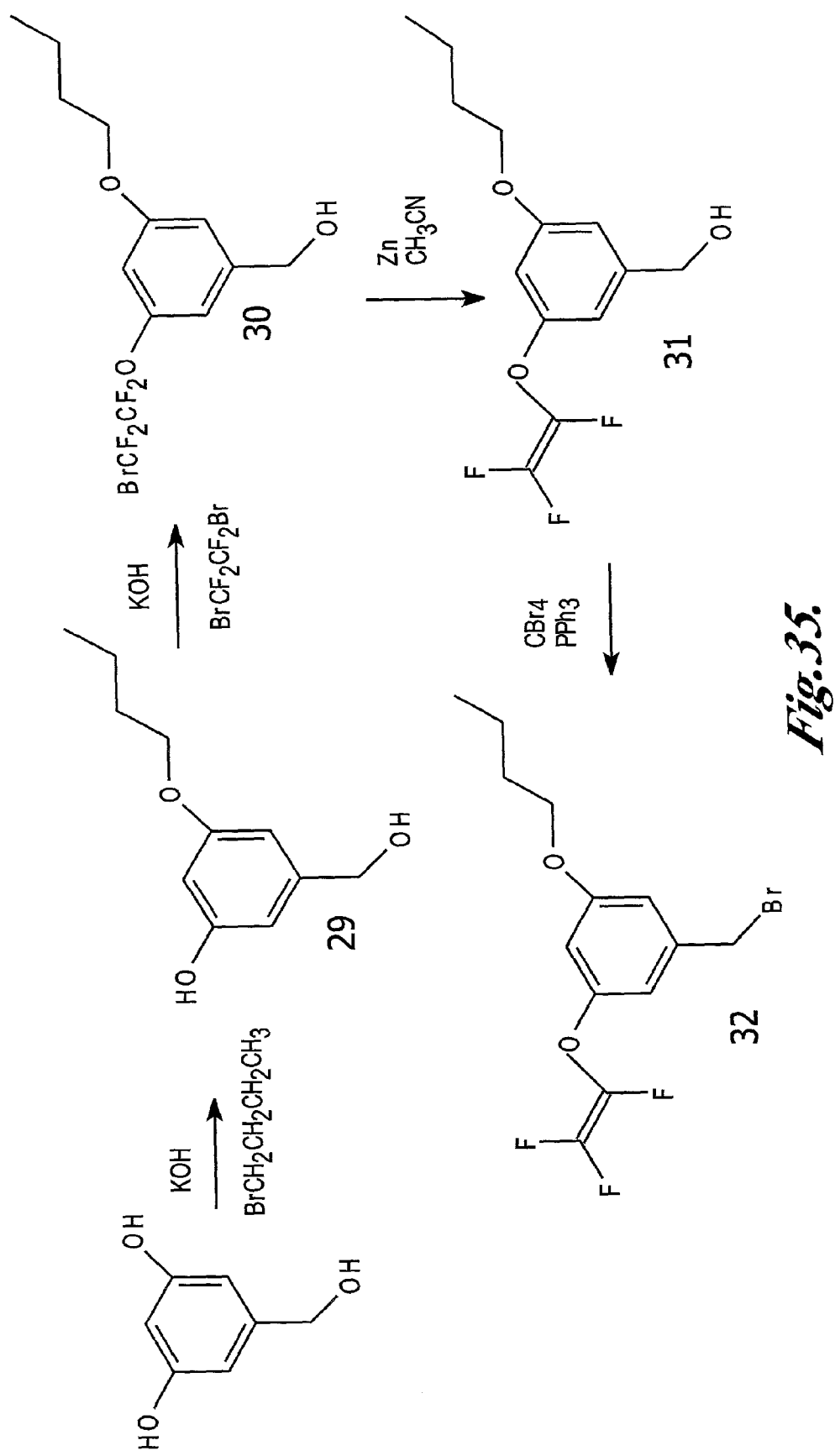
FIG. 35 is a synthetic scheme for the preparation of a dendron useful in the preparation of dendrimer functionalized chromophores of the invention.

The Preparations of Representative Dendrimer Functionalized Chromophores: Amine Donor, Tetracyanobutadiene Acceptor, Thienylvinylene-Containing Bridge In this example, the preparations of representative dendrimer functionalized chromophores of the invention are described. The chromophores include a phenyl amine donor, a substituted thienylvinylene-containing bridge, and a phenyl tetracyanobutadienyl acceptor. Each chromophore includes three dendrons that provide functional groups that are crosslinkable. Each dendron includes a trifluorovinyl ether group. The representative crosslinkable dendrimers are illustrated in FIGS. 29–32. The dendrons useful in preparing the dendrimer functionalized chromophores and their synthetic schemes are illustrated in FIGS. 33–35.

Figure 36:
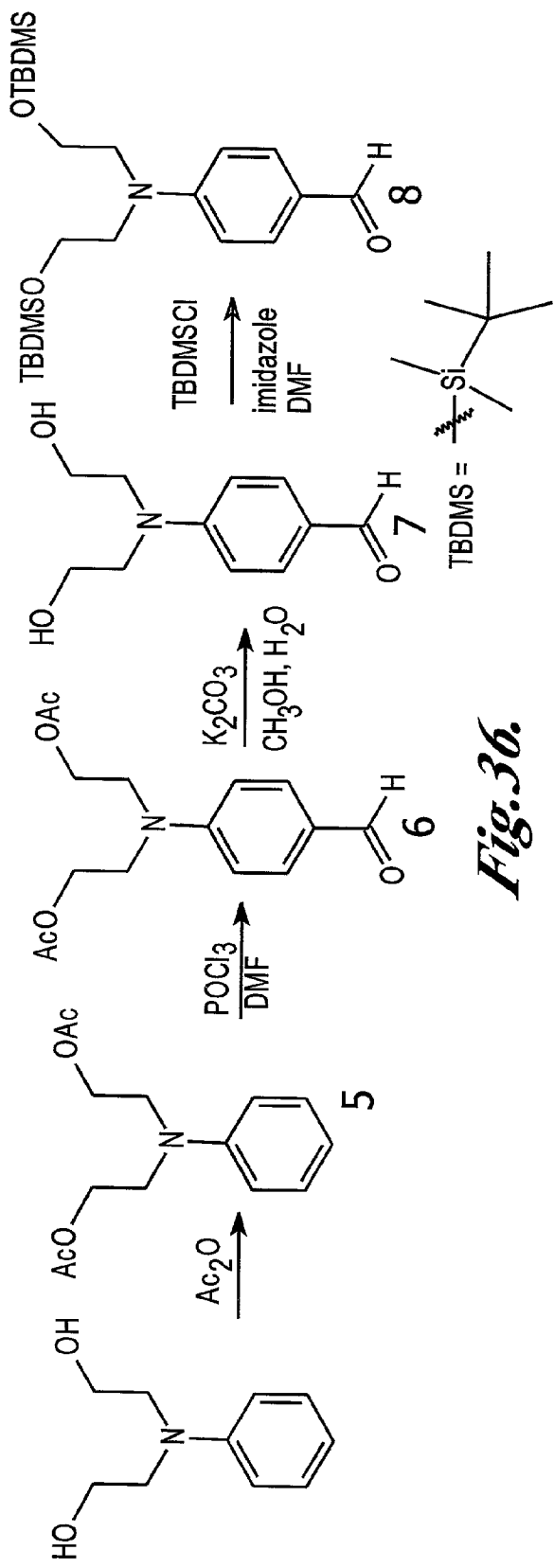
FIG. 36 is a synthetic scheme for the preparation of an amine donor useful in the preparation of dendrimer functionalized chromophores of the invention.
Figure 37:
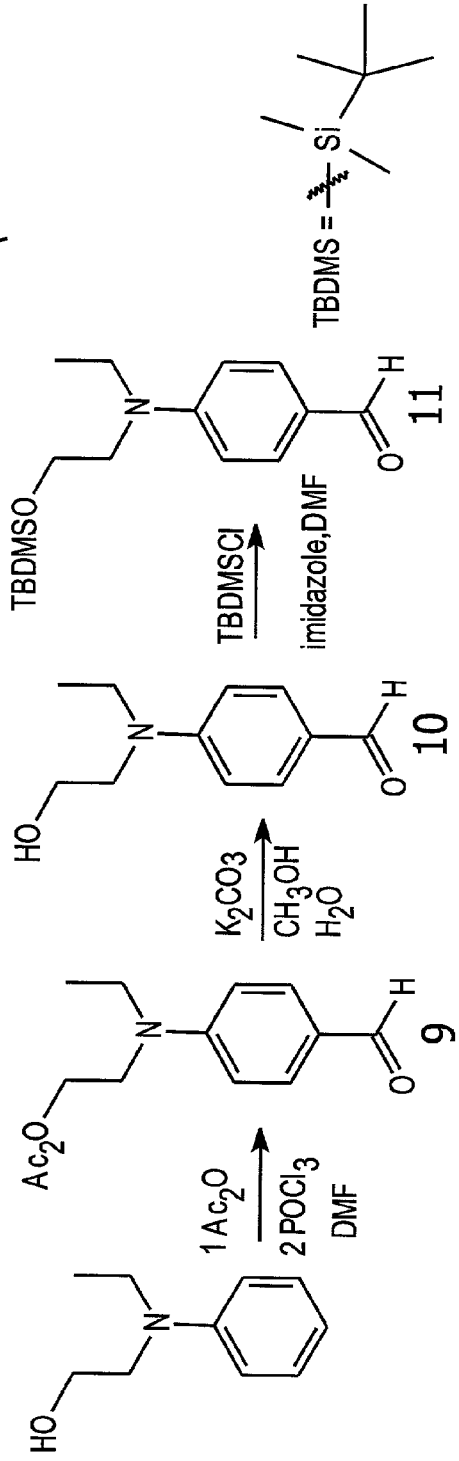
FIG. 37 is a synthetic scheme for the preparation of an amine donor useful in the preparation of dendrimer functionalized chromophores of the invention.

The synthetic schemes for the preparation of donor components of the chromophores are illustrated in FIGS. 36 and 37.

Figure 38:
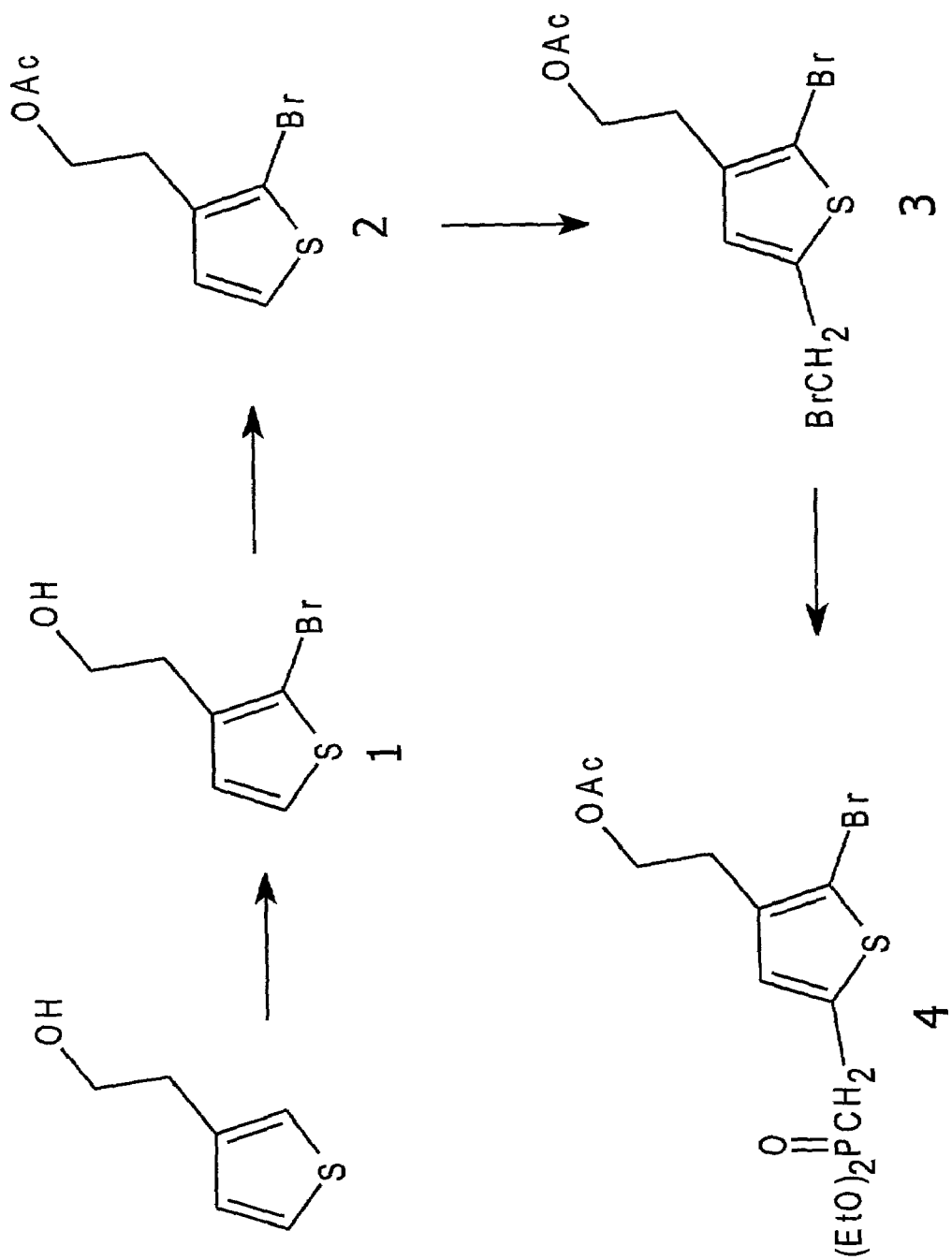
FIG. 38 is a synthetic scheme for the preparation of a thiophene bridge useful in the preparation of chromophores of the invention.

The synthetic scheme for the preparation of the thiophene bridge is illustrated in FIG. 38.

Figure 39:
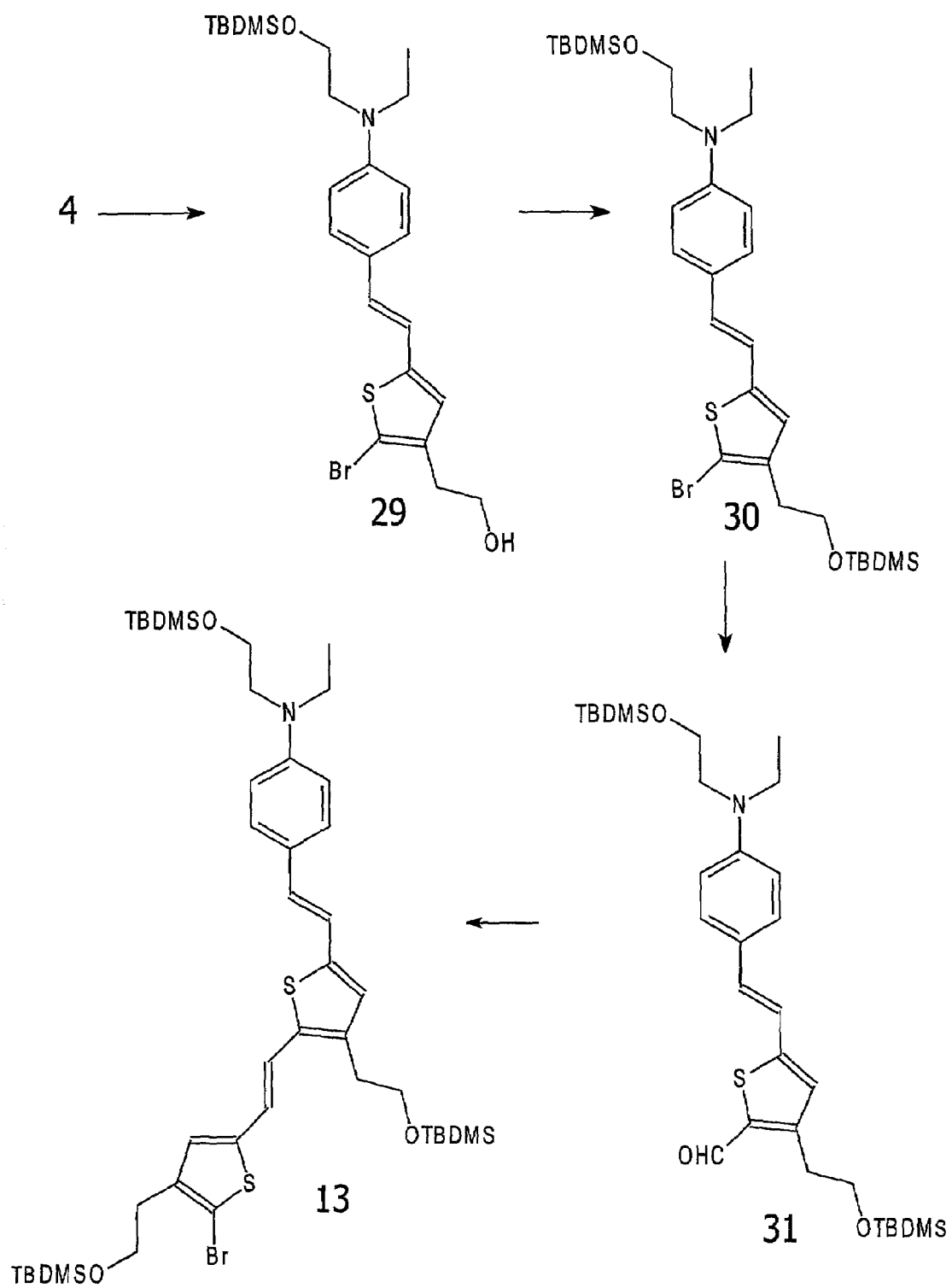
FIG. 39 is a synthetic scheme for the preparation of an amine donor-thiophene bridge useful in the preparation of chromophores of the invention.
Figure 40:
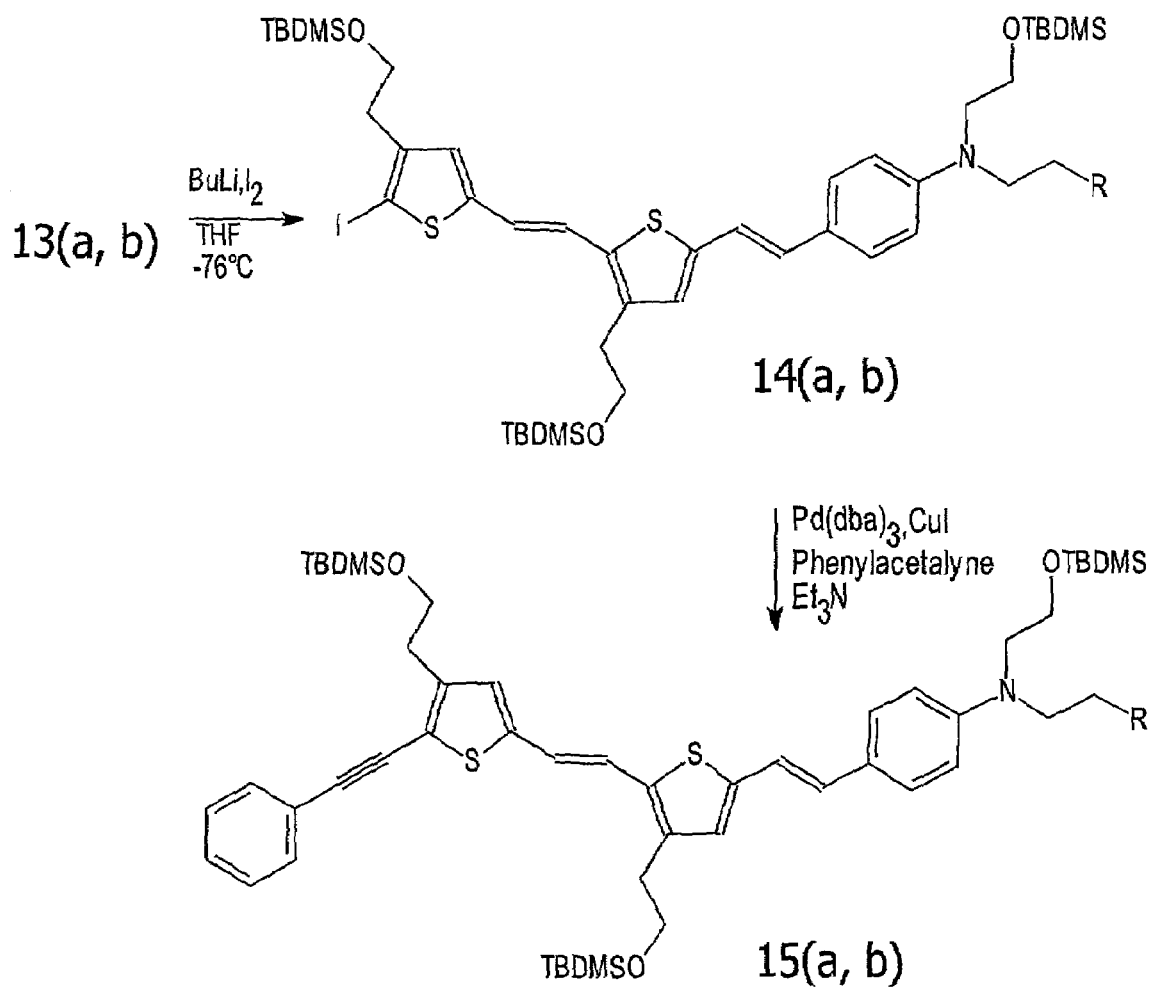
FIG. 40 is a synthetic scheme for the preparation of an amine donor-thiophene bridge useful in the preparation of chromophores of the invention.

The synthetic schemes for the preparation of the donor-thiophene bridge component is illustrated in FIGS. 39 and 40.

Figure 29:
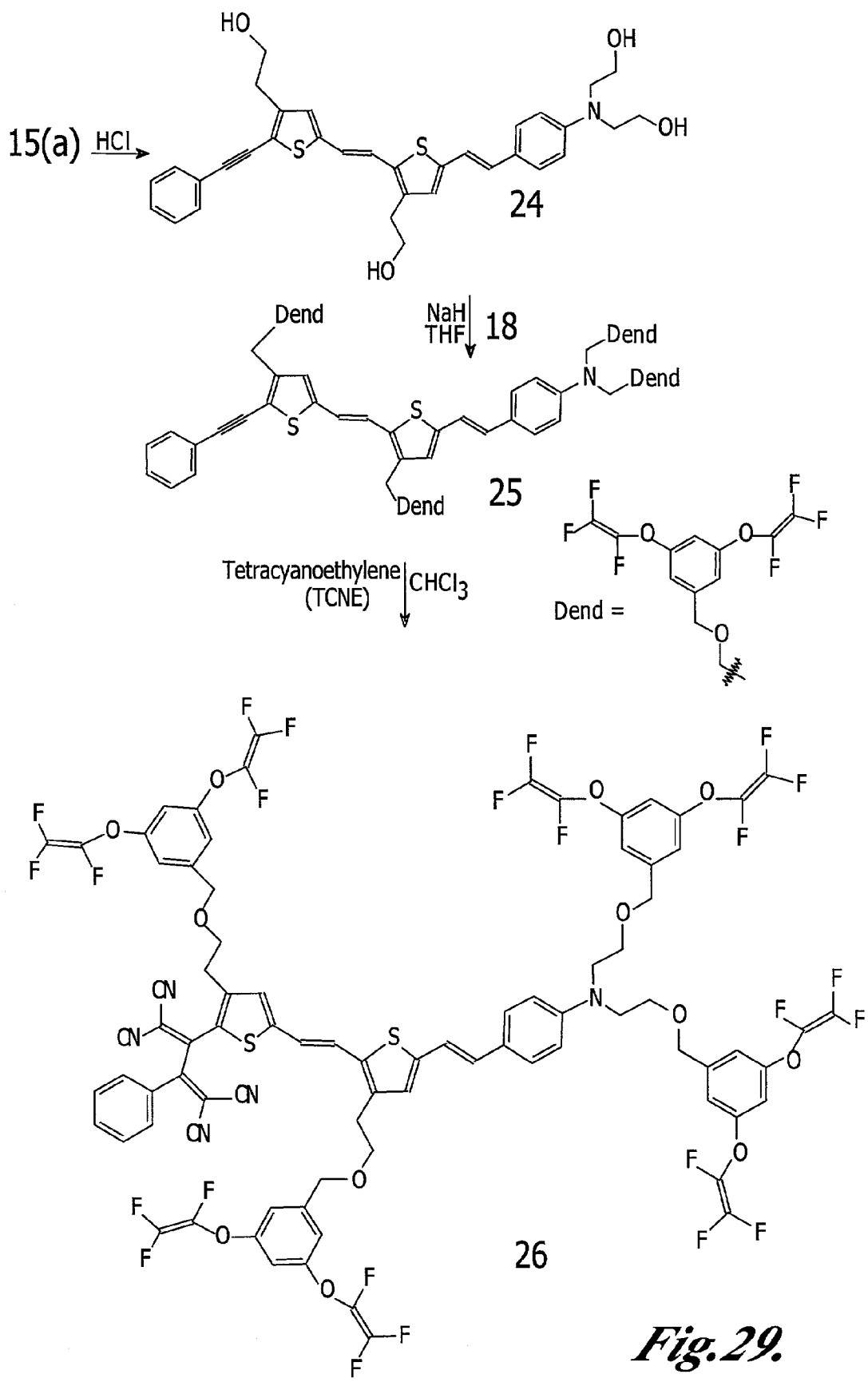
FIG. 29 is a synthetic scheme for the preparation of a representative crosslinkable dendrimer functionalized chromophore of the invention.
Figure 30:
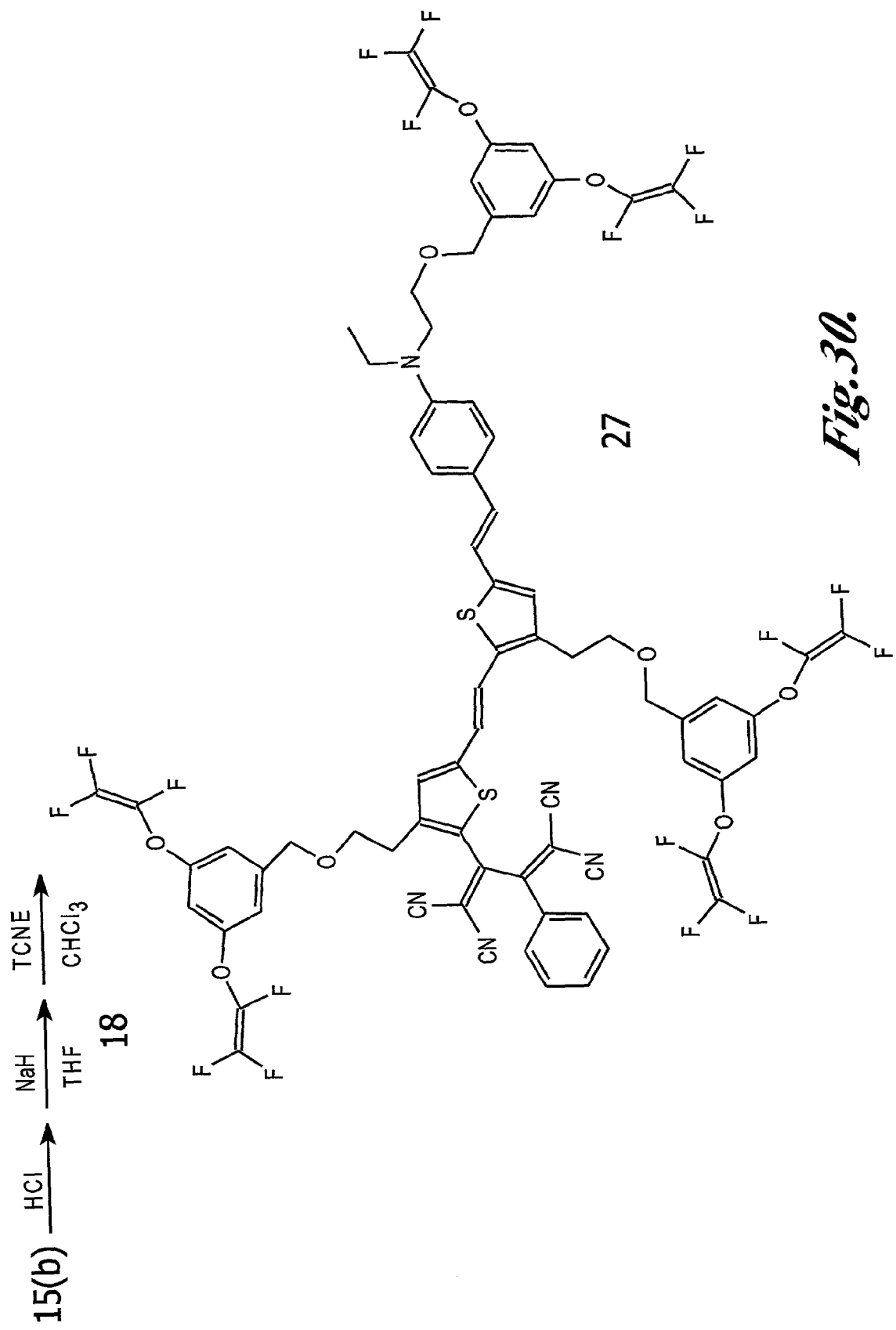
FIG. 30 is a synthetic scheme for the preparation of a representative crosslinkable dendrimer functionalized chromophore of the invention.
Figure 31:
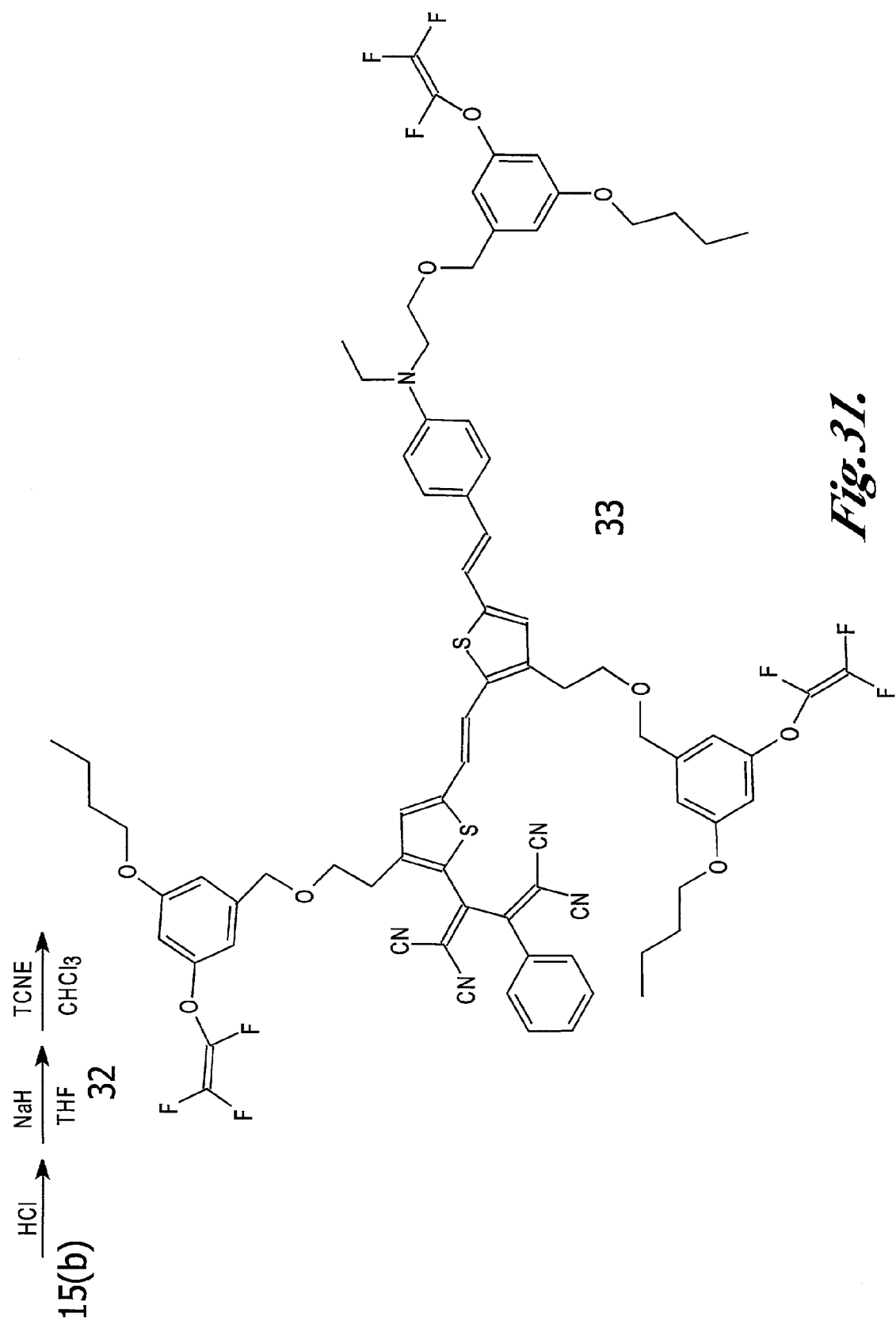
FIG. 31 is a synthetic scheme for the preparation of a representative crosslinkable dendrimer functionalized chromophore of the invention.
Figure 32:
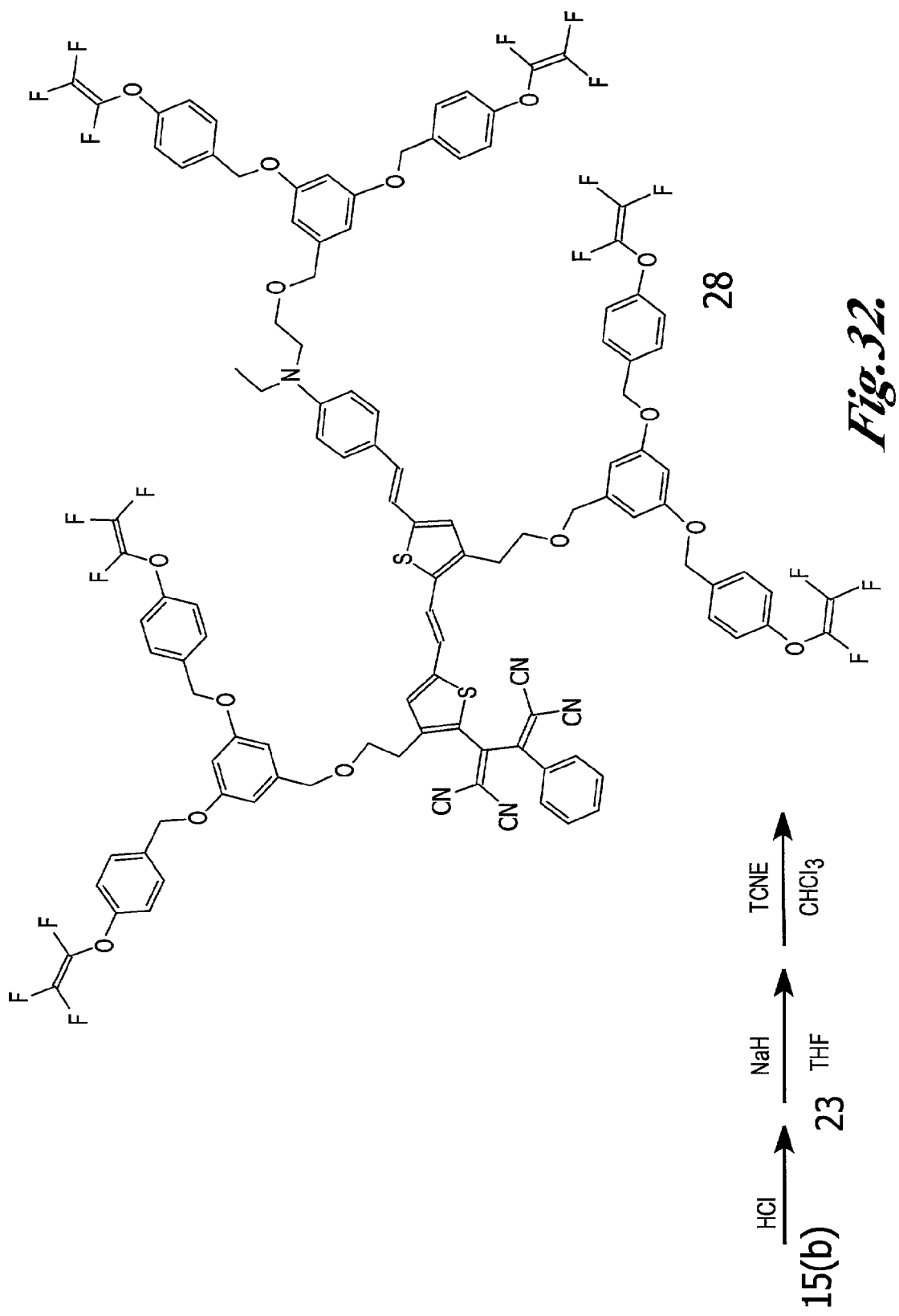
FIG. 32 is a synthetic scheme for the preparation of a representative crosslinkable dendrimer functionalized chromophore of the invention.

The synthetic scheme for the reaction of the chromophore core with the dendrons is illustrated in FIGS. 29–31.

Example 10

Figure 45:
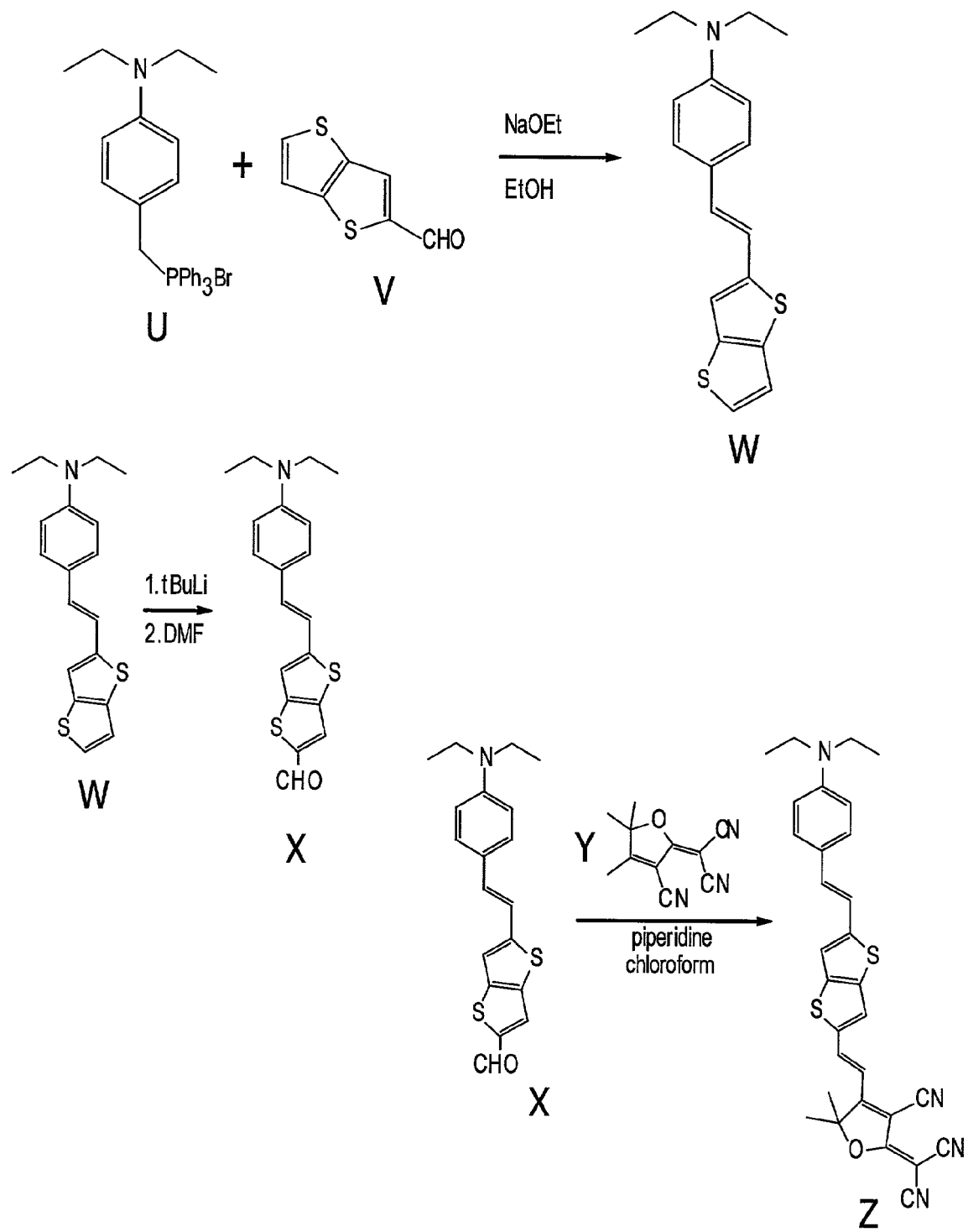
FIG. 45 is a synthetic scheme for the preparation of a representative dithiophene-bridged chromophore of the invention.

The Preparation of a Representative Chromophore: Amine Donor, Dithiophene-Containing Bridge, Furan Acceptor In this example, the preparation of a representative chromophore of the invention is described. The chromophore includes a phenyl amine donor, a fused dithiophene-containing bridge, and a furan acceptor. The overall synthetic scheme is illustrated in FIG. 45. The synthetic schemes follow.

Donor-Bridge W. The Wittig salt donor U (2.264 g, 7.22 mmol) and the monoaldehyde bridge V (1.215 g, 7.22 mmol) were dissolved in 125 mL of ethanol. Sodium ethoxide (0.541 g, 7.94 mmol) was then added and the solution was allowed to reflux overnight under nitrogen purge. The reaction was then cooled and extracted with ether, washed 3× with water and $NH_4Cl$ washings, and dried over sodium sulfate. The crude material was purified via column chromatography using methylene chloride as the mobile phase. The product was recovered and recrystalized from methanol to give yellow crystals. $^1H$ NMR ($CDCl_3$): $\delta1.19$ (t, 3H), $\delta3.39$ (q, 2H), $\delta6.64$ (s, 2H), $\delta6.67$ (s, 2H), $\delta7.11$ (s, 1H), $\delta7.20$ (s, 1H), $\delta7.30$ (d, 2H), $\delta7.37$ (s, 1H). Elemental analysis: $C_{18}H_{19}NS_2$: Calculated; C, 68.96; H, 6.11; N, 4.47; Found; C, 68.67; H, 5.69; N, 4.29.

Compound X. Compound W (0.450 g, 1.43 mmol) was dissolved in dry THF and cooled to −75° C. t-Butyl lithium (3.16 mmol) was added dropwise. The solution was allowed to gradually warm to −45° C. and quenched with dry DMF (2 mL) and react for 2 hours. The crude product was extracted with chloroform, washed with water 3 times, and dried over sodium sulfate. The product was purified via silica gel chromatography with methylene chloride as the mobile phase to reveal red crystals. $^1H$ NMR ($CDCl_3$): $\delta1.20$ (t, 3H), $\delta3.41$ (q, 2H), $\delta7.00$ (d, 4H), $\delta7.15$ (s, 1H), $\delta7.41$ (s, 1H), $\delta7.85$ (s, 1H), $\delta9.92$ (s, 1H).

Chromophore Z. Compound X (2.264 g, 7.22 mmol) and Compound Y (1.215 g, 7.22 mmol) were added to ~100 mL chloroform. After the stirred solution was brought to reflux, ~3 drops of piperidine were added. The reaction was allowed to reflux for 90 min. The reaction mixture was then immediately worked up with extraction with chloroform, washed 3 times with $NH_4Cl$, and dried over sodium sulfate. The crude product was purified via silica gel chromatography with methylene chloride as the mobile phase. The eluted product was recrystallized from methanol several times to yield a metallic green solid. $^1H$ NMR ($CDCl_3$): $\delta1.21$ (t, 3H), $\delta1.56$ (s, 6H), $\delta3.42$ (q, 2H), $\delta6.67$ (d, 4H), $\delta7.37$ (s, 2H), $\delta7.42$ (s, 2H), $\delta7.67$ (s, 1H), $\delta7.82$ (s, 1H). Elemental Analysis: $C_{30}H_{26}N_4OS_2$: Calculated; C, 68.74; H, 5.01; N, 10.72; Found; C, 67.11; H, 4.77; N, 10.59.

Example 11

Figure 46:
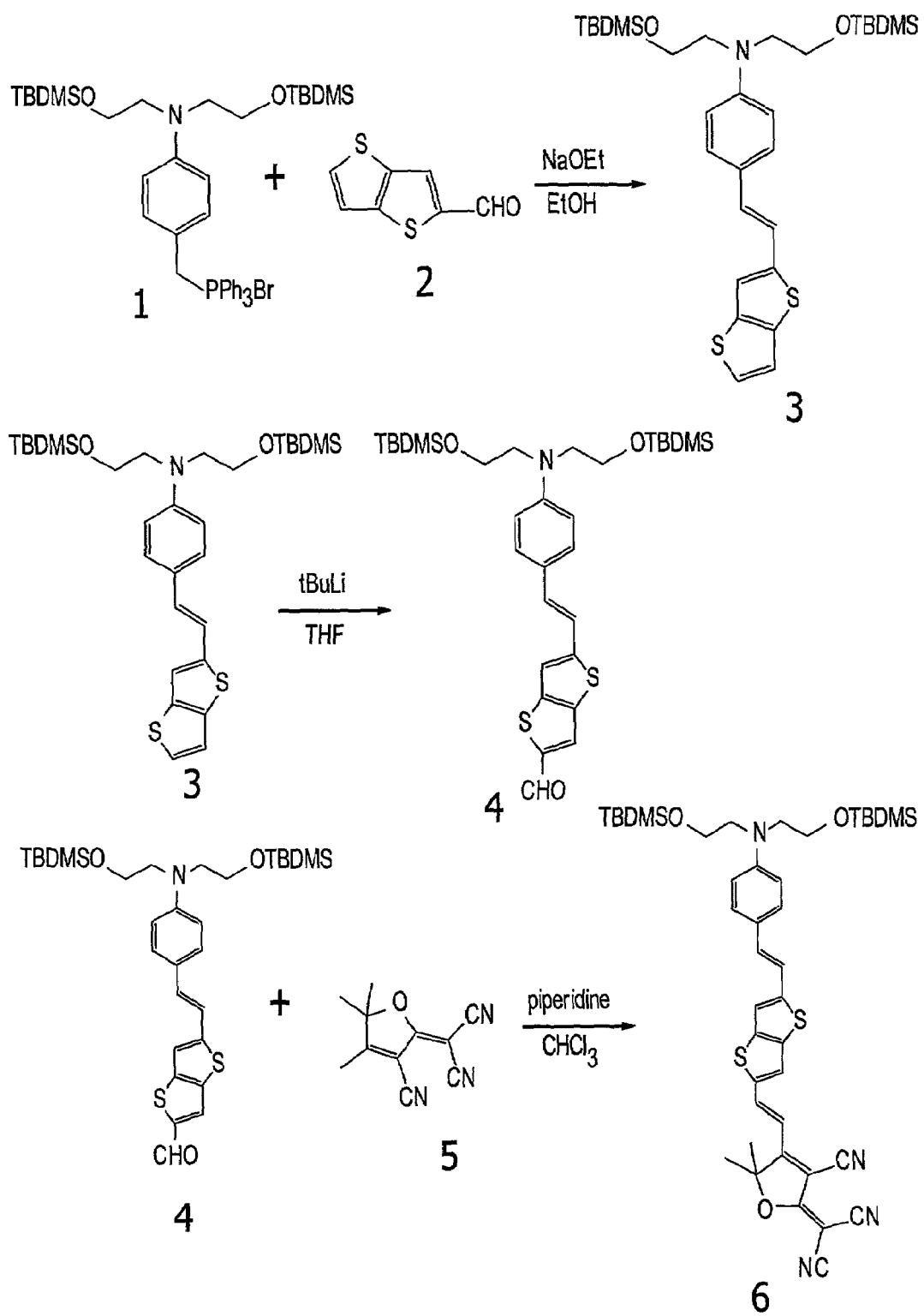
FIG. 46 is a synthetic scheme for the preparation of a representative dithiophene-bridged chromophore of the invention.
Figure 47:
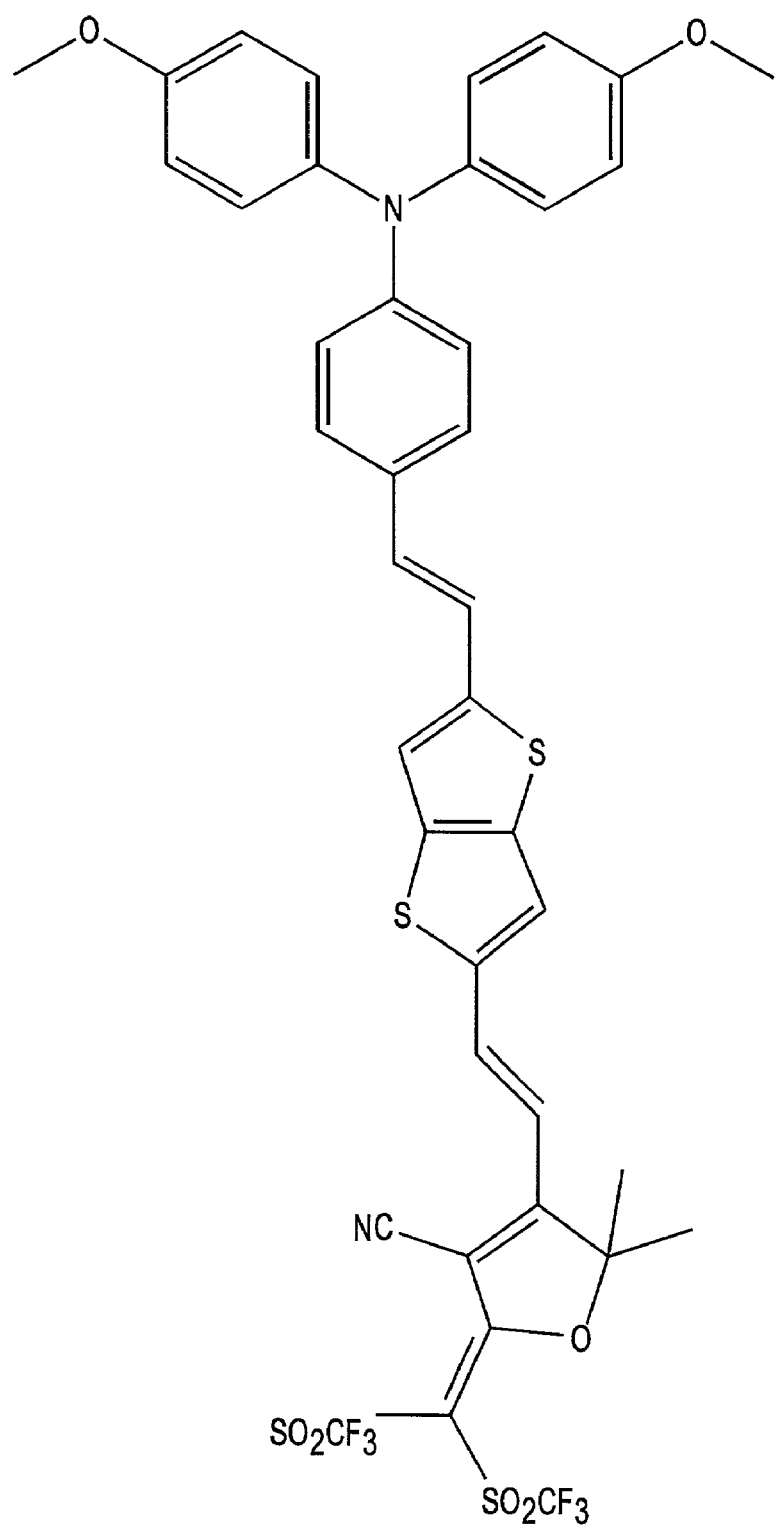
FIG. 47 is an illustration of representative fused dithiophene-bridged chromophore of the invention including a trifluoromethylsulfonyl substituted acceptor.

The Preparation of a Representative Chromophore: Amine Donor, Dithiophene-Containing Bridge, Furan Acceptor In this example, the preparation of a representative chromophore of the invention is described. The chromophore includes a phenyl amine donor, a fused dithiophene-containing bridge, and a furan acceptor. The overall synthetic scheme is illustrated in FIG. 46. The synthetic schemes follow.

Donor-Bridge 3. Compound 1 (6.65 g, 8.69 mmol) and Compound 2 (1.462 g, 8.69 mmol) were dissolved in ethanol under nitrogen purge and a solution of sodium ethoxide (0.65 g, 9.56 mmol) in 50 mL of ethanol was added dropwise into the mixture. The reaction was allowed to stir overnight at reflux. The reaction was worked up by removing ethanol via rotary evaporation. The crude product was dissolved in ether and washed twice with brine and water. The collected ether portions were dried with $MgSO_4$. Flash chromatography on silica with 5% ethyl acetate/95% hexanes (v/v) was used to elute the product. Product recrystalized in $THF/H_2O$ to give 1.2 g of a bright yellow solid. $^1H$ NMR ($d_6$-acetone): $\delta0.05$ (s, 12H), $\delta60.89$ (s, 18H), $\delta3.61$ (t, 2H), $\delta3.84$ (t, 2H), $\delta6.75$ (d, 4H), $\delta6.92$ (s, 1H), $\delta7.20$ (s, 1H), $\delta7.40$ (d, 2H), $\delta7.50$ (s, 1H).

Compound 4. Compound 3 (1.2 g, 2.1 mmol) was dissolved in dry THF, placed under nitrogen and cooled to −75° C. t-Butyl lithium (2.7 mL, 4.6 mmol) was added dropwise to the solution. The reaction mixture was allowed to gradually warm to −20° C. The reaction was quenched with 2 mL of dry DMF and allowed to stir to 2.5 hrs. The crude product was extracted with methylene chloride, washed 3 times with brine, and dried over sodium sulfate. The crude product was purified via column chromatography with 90% hexanes/10% ethyl acetate (v/v) as the mobile phase to reveal 0.375 g of orange colored solid. $^1H$ NMR ($d_6$-acetone): $\delta0.07$ (s, 12H), $\delta0.91$ (s, 18H), $\delta3.64$ (t, 2H), $\delta3.86$ (t, 2H), $\delta6.78$ (d, 4H), $\delta6.96$ (s, 1H), $\delta7.23$ (s, 1H), $\delta7.40$ (d, 2H), $\delta7.50$ (s, 1H), $\delta9.99$ (s, 1H).

Chromophore 6. Compound 4 (0.375 g, 0.62 mmol) and Compound 5 (0.124 g, 0.62 mmol) were added to 25 mL of chloroform. After the stirred solution was brought to reflux, ~3 drops of piperidine were added. The reaction was allowed to reflux for 90 min. The reaction mixture was then immediately worked up with extraction with chloroform, washed 3 times with $NH_4Cl$, and dried over sodium sulfate. The crude product was purified on a silica column chromatography with methylene chloride as the mobile phase. The eluted product was recrystallized from methanol several times to yield 130 mg of a dark metallic green solid. $^1H$ NMR ($d_6$-acetone): $\delta0.05$ (s, 12H), $\delta0.89$ (s, 18H), $\delta1.48$ (s, 6H), $\delta3.21$ (t, 2H), $\delta3.61$ (t, 2H), $\delta6.78$ (d, 4H), $\delta7.02$ (s, 1H), $\delta7.23$(s, 1H), $\delta7.26$ (s, 1H), $\delta7.51$ (s, 1H).

Example 12

Representative Chromophore: Amine Donor, Dithiophene-Containing Bridge, Furan Acceptor In this example, a representative chromophore of the invention is described. The chromophore includes a phenyl amine donor, a fused dithiophene-containing bridge, and a 2-di(trifluoromethylsulfonyl)methylen-3-cyano-5,5-dimethyl-2,4-dihydrofuran acceptor. The chromophore is illustrated in FIG. 47. The chromophore can be prepared by the synthetic procedures described herein.

Example 13

Figure 48:
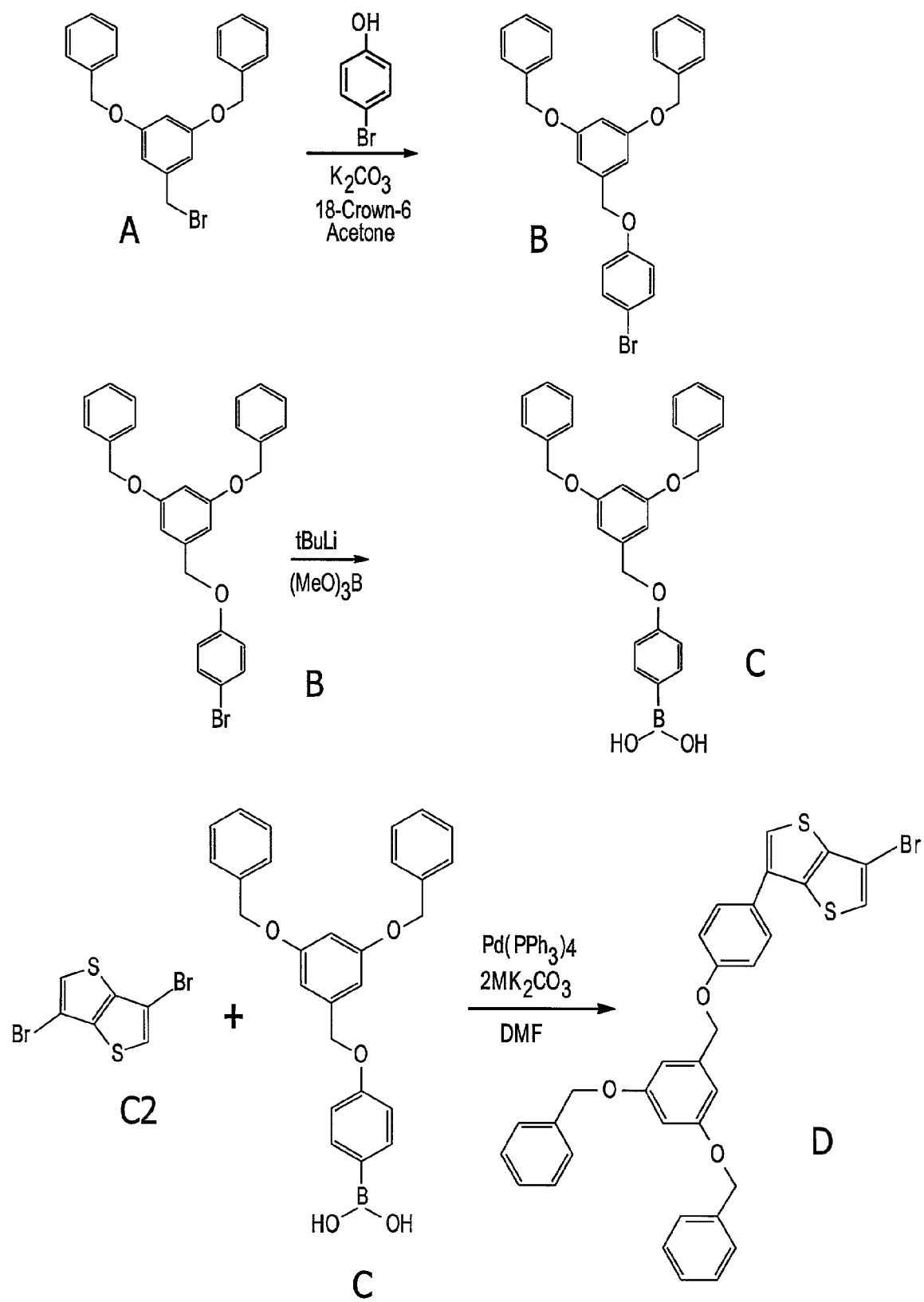
FIG. 48 is a synthetic scheme for the preparation of a representative dendrimer functionalized donor-bridge component useful in the preparation of chromophores of the invention.

The Preparation of Representative Dendrimer Functionalized Donor-Bridge Component In this example, the preparation of a representative dendrimer functionalized donor-bridge component is described. The donor-bridge component includes a phenol donor and a fused dithiophene bridge. The donor includes a phenyl benzyl ether dendron. The overall synthetic scheme is illustrated in FIG. 48. The synthetic schemes follow.

Dendron Preparation

Compound B. Compound A (1.0 g, 2.61 mmol) was prepared according to literature procedures (Hawker, Craig J. and Frechet, J. M. J., J. Am. Chem. Soc. 1990, 112, 7638–7647) and was added to p-bromophenol (0.496 g, 2.87 mmol), 18-crown-6 (0.069 g, 0.261 mmol), and potassium carbonate (0.541 g, 3.91 mmol) in acetone. The reaction mixture was stirred vigorously and heated to reflux for 20 hours. The resulting mixture was rotary evaporated to remove the solvent, extracted with methylene chloride, washed several times with 1M NaOH solution, and dried over sodium sulfate. The crude product was purified via column chromatography to give a white solid. $^1$H NMR (CDCl$_3$): δ4.94 (s, 2H), δ5.09 (s, 4H), δ6.56 (s, 2H), δ6.63 (s, 1H), δ7.33–7.45 (m, 10H). Elemental Analysis: C$_{27}$H$_{23}$BrO$_3$: Calculated: C, 68.22; H, 4.88; N, 0; Found: C, 67.55; H, 4.84; N 0.00.

Compound C. Compound C (8.442 g, 17.8 mmol) was added to dry THF. t-Butyl lithium (31.9 mmol) was added dropwise to the cooled solution at −75° C. The lithiated species was allowed to react under nitrogen for 1 hour. Trimethyl borate (53.27 mmol) was added quickly to the reaction flask via syringe. The reaction mixture was then allowed to gradually warm up to room temperature overnight. The reaction mixture was then extracted with ether, washed 2× with 10% HCl solution, and dried over Na$_2$SO$_4$. Crude product was purified via column chromatography with 50% ethyl acetate/50% hexanes (v/v) as the mobile phase. $^1$H NMR: (CDCl$_3$): δ5.04 (s, 2H), δ5.08 (s, 4H), δ7.32–7.45 (m, 10H), δ7.72 (d, 4H), δ7.85 (s, 2H).

Dendrimer Functionalized Donor-Bridge Preparation

Compound D. Compound C2 (0.290 g, 0.973 mmol), previously prepared from literature procedures (Fuller, L. S., Iddon, B., and Smith, K. A. J. Chem. Soc., Perkin Trans. 1 1997, (22), 3465–3470), and Compound C (1.714 g, 3.89 mmol) was dissolved in dry DMF. The reaction vessel was flushed with nitrogen for 1 hour. To an addition funnel was added 2M K$_2$CO$_3$ (~1 mL) and flushed with N$_2$ for 1 hour. Pd(PPh$_3$)$_4$ was then added to the reaction mixture. The reaction was then heated to 60° C. and the K$_2$CO$_3$ solution was added dropwise. After complete addition, the solution was heated to 80–90° C. overnight. The reaction was worked up by extracting with methylene chloride, washed several times with water washings, and dried with sodium sulfate. Crude product was purified via column chromatography 10%/90% (v/v) ethyl acetate/hexanes as the mobile phase. Elemental analysis revealed that the thienothiophene bridge had been substituted at one bromine position with one dendrimer wedge. Elemental Analysis: C$_{33}$H$_{25}$BrO$_3$S$_2$: Calculated; C, 64.60; H, 4.11; N, 0.00; Found: C, 64.84; H, 4.13; N, 0.04.

While the preferred embodiment of the invention has been illustrated and described, it will be appreciated that various changes can be made therein without departing from the spirit and scope of the invention.

What is claimed is:

1. A dihydrofuran-containing nonlinear optical chromophore having the structure:

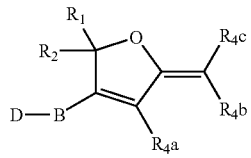

wherein D is a π-electron donor group;
wherein B is a π-electron conjugated bridge group that provides electronic conjugation from the donor group to the dihydrofuran; and
wherein R$_1$ and R$_2$ are alkyl groups, R$_4$a, R$_4$b, and R$_4$c are independently selected from F, CN, CF$_3$, and CF$_3$SO$_2$, provided that R$_4$a, R$_4$b, and R$_4$c are not all CN.

2. The chromophore of claim 1, wherein R$_4$a, R$_4$b, and R$_4$c are independently selected from F, CF$_3$, and CF$_3$SO$_2$.

3. The chromophore of claim 1, wherein R$_4$a is CN, R$_4$b is CN, and R$_4$c is CF$_3$SO$_2$.

4. The chromophore of claim 1, wherein R$_4$a is CF$_3$SO$_2$, R$_4$b is CN, and R$_4$c is CF$_3$SO$_2$.

5. The chromophore of claim 1, wherein R$_4$a, R$_1$b, and R$_4$c are independently selected from CN, CF$_3$, and CF$_3$SO$_2$.

6. The chromophore of claim 1, wherein R$_4$a is F, R$_4$b is CN, and R$_4$c is F.

7. The chromophore of claim 1, wherein R$_4$a is CF$_3$, R$_4$b is CN, and R$_4$c is CF$_3$.

8. The chromophore of claim 1, wherein R$_4$a is CF$_3$SO$_2$, R$_4$b is CF$_3$SO$_2$, and R$_4$c is CF$_3$SO$_2$.

9. The chromophore of claim 1, wherein R$_4$a is CN, R$_4$b is CF$_3$SO$_2$, and R$_4$c is CF$_3$SO$_2$.

10. A compound selected from the group consisting of

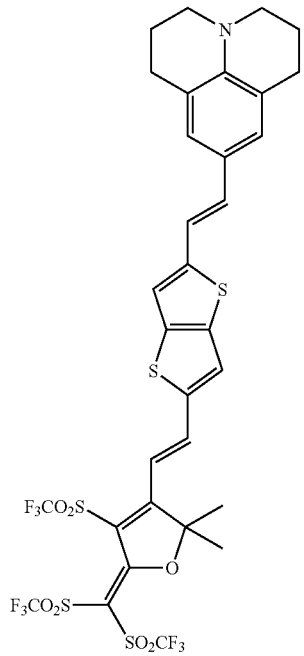

,

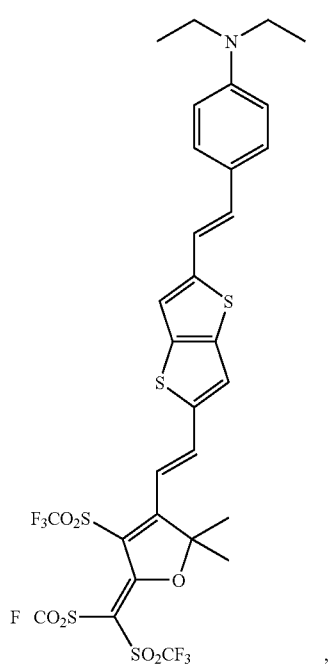
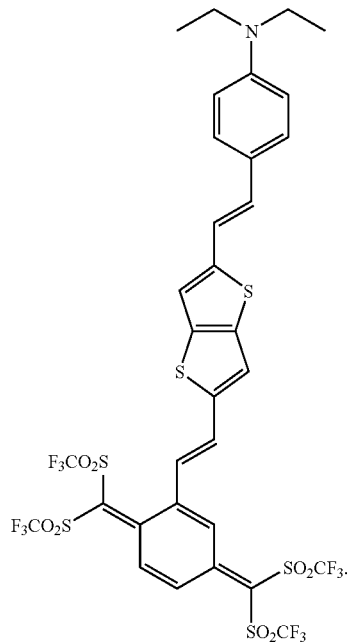
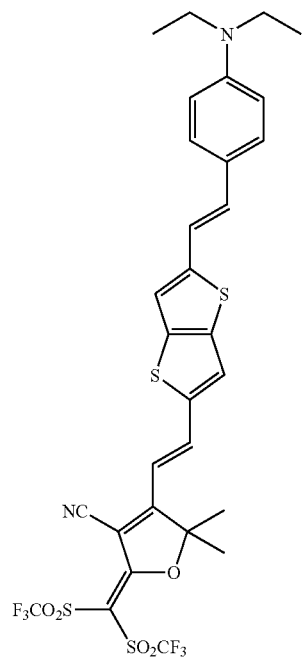
, and
11. A compound having the structure
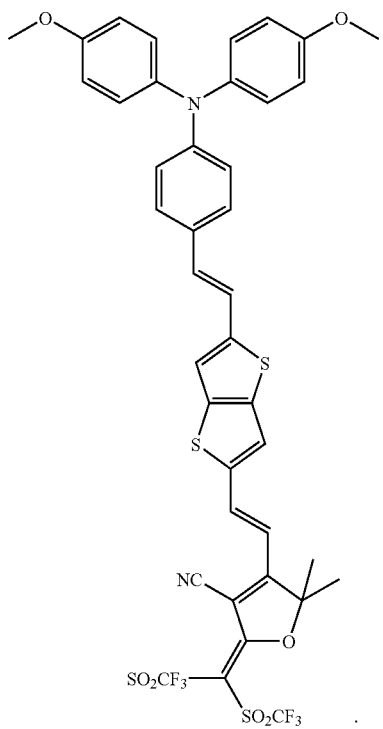

12. A compound having the structure
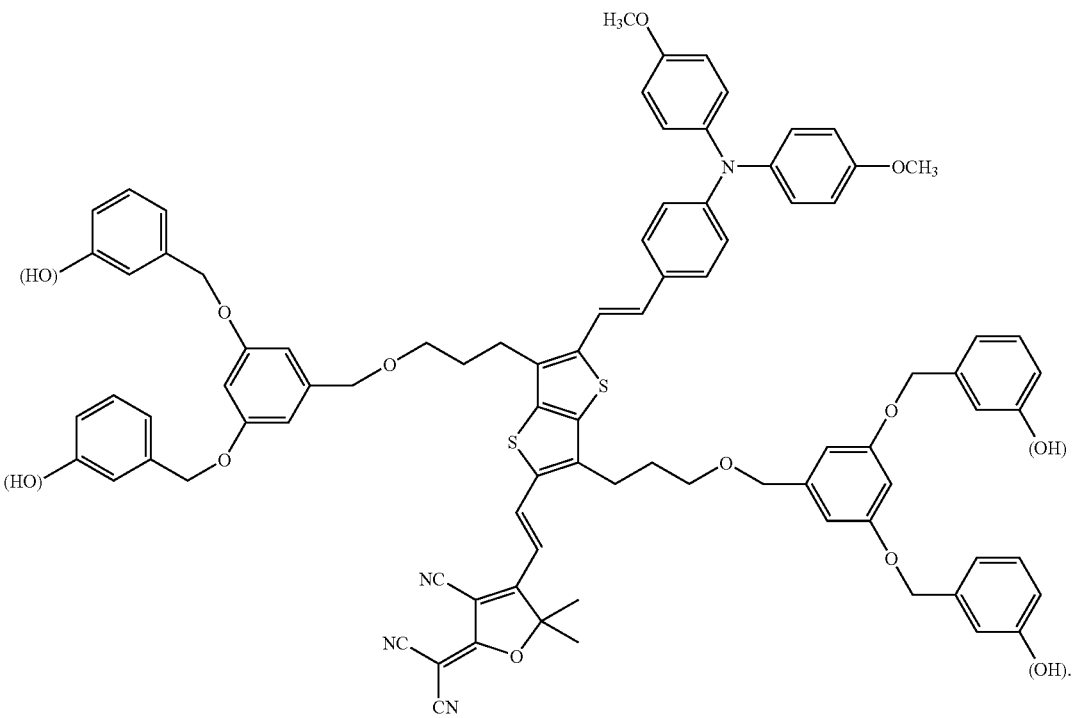
13. A compound having the structure:
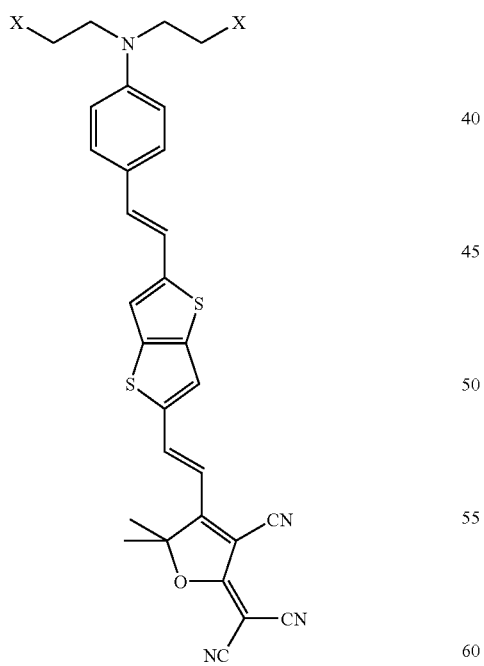
wherein X is hydrogen or t-butyldimethylsiloxy.
* * * * *

UNITED STATES PATENT AND TRADEMARK OFFICE
CERTIFICATE OF CORRECTION

| | |
|---|---|
| PATENT NO. | : 7,029,606 B2 |
| APPLICATION NO. | : 09/912444 |
| DATED | : April 18, 2006 |
| INVENTOR(S) | : L.R. Dalton et al. |

Page 1 of 1

It is certified that error appears in the above-identified patent and that said Letters Patent is hereby corrected as shown below:

| COLUMN | LINE | ERROR |
|---|---|---|
| 32 (Claim 5, | 30 line 1) | "$R_1b$," should read --$R_4b$,-- |

Signed and Sealed this

Fifteenth Day of August, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,029,606 B2 | Page 1 of 1 |
| APPLICATION NO. | : 09/912444 | |
| DATED | : April 18, 2006 | |
| INVENTOR(S) | : L.R. Dalton et al. | |

It is certified that error appears in the above-identified patent and that said Letters Patent is hereby corrected as shown below:

| COLUMN | LINE | ERROR |
|---|---|---|
| 1 | 8 | before "FIELD OF THE INVENTION" insert --STATEMENT OF GOVERNMENT LICENSE RIGHTS     This invention was made with US Government support under grant numbers F49620-99-1-0287 and F49620-00-1-0060 awarded by Air Force Office of Scienific Research (AFOSR/JA). The US Government has certain rights in this invention.-- |

Signed and Sealed this

Fourteenth Day of November, 2006

JON W. DUDAS
*Director of the United States Patent and Trademark Office*